(12) United States Patent
Phipps et al.

(10) Patent No.: US 9,694,050 B2
(45) Date of Patent: Jul. 4, 2017

(54) THY1 (CD90) AS A NOVEL THERAPY TO CONTROL ADIPOSE TISSUE ACCUMULATION

(71) Applicants: Richard P. Phipps, Pittsford, NY (US); Collynn F. Woeller, Webster, NY (US); Steven E. Feldon, Rochester, NY (US)

(72) Inventors: Richard P. Phipps, Pittsford, NY (US); Collynn F. Woeller, Webster, NY (US); Steven E. Feldon, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/437,378

(22) PCT Filed: Oct. 21, 2013

(86) PCT No.: PCT/US2013/065952
§ 371 (c)(1),
(2) Date: Apr. 21, 2015

(87) PCT Pub. No.: WO2014/063155
PCT Pub. Date: Apr. 24, 2014

(65) Prior Publication Data
US 2015/0283205 A1    Oct. 8, 2015

Related U.S. Application Data

(60) Provisional application No. 61/716,558, filed on Oct. 21, 2012.

(51) Int. Cl.
| | |
|---|---|
| A61K 38/16 | (2006.01) |
| A61K 38/00 | (2006.01) |
| A61K 38/17 | (2006.01) |
| C12N 15/113 | (2010.01) |
| A61K 9/00 | (2006.01) |
| C07K 14/705 | (2006.01) |

(52) U.S. Cl.
CPC .......... *A61K 38/177* (2013.01); *A61K 9/0014* (2013.01); *A61K 9/0048* (2013.01); *A61K 38/1774* (2013.01); *C07K 14/70503* (2013.01); *C12N 15/1138* (2013.01); *C12N 2310/113* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 7,470,537 B2 | 12/2008 | Hedrick et al. | |
| 7,842,291 B1 * | 11/2010 | Ruben ................ | C12N 15/1137 424/130.1 |
| 2003/0082152 A1 | 5/2003 | Hedrick et al. | |
| 2004/0266993 A1 | 12/2004 | Evans | |
| 2005/0076396 A1 | 4/2005 | Katz et al. | |
| 2005/0153441 A1 | 7/2005 | Hedrick et al. | |
| 2005/0153442 A1 | 7/2005 | Katz et al. | |
| 2009/0181456 A1 | 7/2009 | Hedrick et al. | |
| 2010/0119609 A1 | 5/2010 | Dobak | |
| 2011/0027879 A1 | 2/2011 | Katz et al. | |
| 2011/0256204 A1 | 10/2011 | Bader | |
| 2012/0015001 A1 | 1/2012 | Phipps et al. | |

FOREIGN PATENT DOCUMENTS

| | | | |
|---|---|---|---|
| WO | WO 98/12207 | * | 3/1998 |
| WO | 99/45951 A2 | | 9/1999 |
| WO | 03/022988 A2 | | 3/2003 |
| WO | 2005/113780 A1 | | 1/2005 |
| WO | 2010/133970 A1 | | 11/2010 |
| WO | 2010135714 A2 | | 11/2010 |
| WO | 2011/119199 A1 | | 9/2011 |

OTHER PUBLICATIONS

Bowie et al, 1990, Science 247:1306-1310.*
Wells, 1990, Biochemistry 29:8509-8517.*
; Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Liao et al., "Cells Isolated from Inflamed Periapical Tissue Express Mesenchymal Stem Cell Markers and Are Highly Osteogenic," J Endod. 37(9):1217-1224 (2011).
Khoo et al., "Evidence for Enhanced Thy-1 (CD90) Expression in Orbital Fibroblasts of Patient with Graves' Ophthalmopathy," Thyroid 18(12):1291-1296 (2008).
Chang et al., "Characterization of Two Populations of Mesenchymal Progenitor Cells in Umbilical Cord Blood," Cell Biol. Int. 30:495-499 (2006).
Gagnon et al., "Thy-1 Expression During 3T3-L1 Adipogenesis," Horm. Metab. Res. 36(10):728-31 (2004).
Smith et al., "Orbital Fibroblast Heterogeneity May Determine the Clinical Presentation of Thyroid-Associated Ophthalmopathy," J. Clin. Endocrinol. Metab. 87(1):385-392 (2002).
Koumas et al., "Thy-1 Expression in Human Fibroblast Subsets Defines Myofibroblastic of Lipofibroblastic Phenotypes," Am. J. Pathology 163(4):1291-1300 (2003).

(Continued)

*Primary Examiner* — Shulamith H Shafer
(74) *Attorney, Agent, or Firm* — LeClairRyan, a Professional Corporation

(57) ABSTRACT

The present invention relates to methods of treating a condition involving excessive adipogenesis. This method relates to selecting a subject having a condition involving excessive adipogenesis and administering to the selected subject a composition comprising a Thy1 protein or polypeptide fragment thereof, or an agent that enhances Thy1 expression, under conditions effective to treat the condition. The present invention also relates to isolated nucleic acid molecules encoding a Thy1 protein or the fragment thereof and pharmaceutical formulations including such a protein or fragment thereof or an agent that enhances Thy1 expression and a pharmaceutically acceptable carrier. The present invention also relates to methods of inhibiting adipogenesis and/or decreasing adipocyte size, as well as methods of screening a candidate compound for its ability to influence adipogenesis.

10 Claims, 18 Drawing Sheets

(56) References Cited

OTHER PUBLICATIONS

Koo et al., "Fyn Inhibition by Cycloalkane-Fused 1, 2-Dithiole-3-thiones Enhances Antioxidant Capacity and Protects Mitochondria from Oxidative Injury," Molecular Pharmacology 82(1):27-36 (2012).
Lehmann et al., "Novel Anti-Adipogenic Activity Produced by Human Fibroblasts," Am J Physiol Cell Physiol 299: C672-C681 (2010).
Trajkovski et al., "MicroRNAs 103 and 107 Regulate Insulin Sensitivity," Nature 474(7353):649-653 (2011).
International Search Report and Written Opinion for corresponding application No. PCT/US2013/065952 mailed Mar. 4, 2014.
International Preliminary Report on Patentability for corresponding International Application No. PCT/US2013/065952 (Apr. 21, 2015) (13 pages).
Extended European Search Report for corresponding European Paten Application No. 13847469.7, 11 pages (dated Apr. 15, 2016).
Devasahayam et al., "The Glycan Processing and Site Occupancy of Recombinant Thy-1 is Markedly Affected by the Presence of a Glycosylphosphatidylinositol Anchor," Glycobiology 9(12):1381-1387 (1999).
Varisco et al., "Thy-1 Signals Through PPARYy to Promote Lipofibroblast Differentiation in the Developing Lung," Am. J. Respir. Cell. Mol. Biol. 46(6)765-772 (2012).
Chen et al., "Krox20 Stimulates Adipogenesis Via C/EBPβ-dependent and -independent Mechanisms," Cell Metab. 1:93-106 (2005).
Woeller et al., "Thy1 (CD90) Controls Adipogenesis by Regulating Activity of the Src Family Kinase, Fyn," The FASEB J. 29:920-931 (2015).
Moreno-Navarette et al., "Adipocyte Differentiation," in 2 Adipose Tissue Biology 17-38 (Symonds, M.E ed., 2012).
Li et al., "Adipogenic Potential of Adipose Stem Cell Subpopulations," NIH Public Access Author Manuscript, 18 pages (available in PMC Sep. 17, 2014), published in final edited form as Plast. Reconstr. Surg. 128(3):663-672 (2011).
Examination Report for European Patent Application No. 13847469.7 (Feb. 1, 2017).

* cited by examiner

```
         10         20         30         40         50         60
QKVTSLTACLV DQSLRLDCR HENTSSSPIQ YEFSLTRETK KRVLFGTVGV PEHTYRSRCN 70         80         90        100        110
FTSKYNMKVL YLSAFTSKDE GTYTCALHHS GHSPPISSQN VTVLRDKLVK C
```

Number of amino acids: 111     Molecular weight: 12553.2     Theoretical pI: 9.16

Ac-QKVTSLTACLVDQSLRLD
Molecular weight:                 2032.35 g/mol
Extinction coefficient:            0 $M^{-1}cm^{-1}$
Iso-electric point:                pH 3.88
Net charge at pH 7:            -1
Estimated solubility:            Good water solubility.
N-terminal glutamine forms cyclic pyroglutamate under acidic conditions and is unstable. This can be prevented by acetylation (Ac-).

CRHENTSSSPIQYEFSLTRE
Molecular weight:                 2384.57 g/mol
Extinction coefficient:            1280 $M^{-1}cm^{-1}$
Iso-electric point:                pH 5.4
Net charge at pH 7:            -1
Estimated solubility:            Good water solubility.

TKKHVLFGTVGVPEHTYRSRTNFTS
Molecular weight:                 2863.23 g/mol
Extinction coefficient:            1280 $M^{-1}cm^{-1}$
Iso-electric point:                pH 10.69
Net charge at pH 7:            3.2
Estimated solubility:            Good water solubility.

KYNMKVLYLSAFTSKDEGTYT
Molecular weight:                 2459.8 g/mol
Extinction coefficient:            3840 $M^{-1}cm^{-1}$
Iso-electric point:                pH 9.32
Net charge at pH 7:            1
Estimated solubility:            Good water solubility.

CALHHSGHSPPISSQNVTVLRDKLVK
Molecular weight:                 2824.26 g/mol
Extinction coefficient:            0 $M^{-1}cm^{-1}$
Iso-electric point:                pH 9.9
Net charge at pH 7:            2.2
Estimated solubility:            Good water solubility.

FIG. 2B

THY1 (CD90) AS A NOVEL THERAPY TO CONTROL ADIPOSE TISSUE ACCUMULATION

This application is a national stage application under 35 U.S.C. 371 of PCT Application No. PCT/US2013/065952, filed Oct. 21, 2013, which claims the priority benefit of U.S. Provisional Patent Application Ser. No. 61/716,558, filed Oct. 21, 2012, each of which is hereby incorporated by reference in its entirety.

This invention was made with government support under grant number RO1 EY017123 awarded by the National Institutes of Health National Eye Institute. The government has certain rights in this invention.

FIELD OF THE INVENTION

The present invention relates to regulation of adipogenesis, in particular methods of treating conditions involving excess adipogenesis, inhibiting adipogenesis and/or decreasing adipocyte size, as well as methods for screening compounds that moderate adipogenesis, and pharmaceutical formulations for carrying out the treatments of the present invention.

BACKGROUND OF THE INVENTION

Obesity has risen dramatically over the last 30 years. In the US alone, 60 million people are defined as clinically obese. Juonala, et al., "Childhood Adiposity, Adult Adiposity, and Cardiovascular Risk Factors," *N Engl J Med* 365 (20):1876-85 (2011). Especially concerning is the almost epidemic rate of childhood obesity. Ludwig, D. S., "Childhood Obesity—the Shape of Things to Come," *N Engl J Med* 357(23):2325-7 (2007). Obesity can cause or contribute to many health problems such as type-2 diabetes, cardiovascular disease, asthma, and cancer. Of further importance is the fact that many human tissues can become fatty and lose function as a consequence of disease or insult. Examples of this include liver cirrhosis from infection or excess alcohol consumption. Others include conversion of healthy red bone marrow to fatty yellow marrow by mesenchymal stem cells as a consequence of age and also of osteoporosis. Current medications, most small molecules, target appetite, nutrient and food absorption, and increasing metabolism. These drugs have undesirable side effects. In addition, surgical methods are invasive and have associated risks of infection and tissue damage. Hormone or soluble peptide therapeutics for obesity are severely lacking and there is a great need for new therapeutics to control excess fat deposition.

While no single factor appears to be responsible for the dangerous rise in obesity rates, several focal points are ascribed to being causal: genetics, behavior, food intake, stress and lack of exercise. One factor now beginning to be uncovered is early life exposures (The Barker Theory on the developmental origins of health and disease) to environmental contaminants that appear to "reprogram" human physiology. Trosko et al., "Factors to Consider in the Use of Stem Cells for Pharmaceutic Drug Development and for Chemical Safety Assessment," *Toxicology* 270(1):18-34 (2010). Environmental compounds termed obesogens have been identified that disrupt the endocrine system and cause increased adipogenesis in both in vitro and in vivo models. Janesick, et al., "Endocrine Disrupting Chemicals and the Developmental Programming of Adipogenesis and Obesity," *Birth Defects Res C Embryo Today* 93(1):34-50 (2011); Grun et al., "Environmental Obesogens: Organotins and Endocrine Disruption Via Nuclear Receptor Signaling," *Endocrinology* 147(6 Suppl):550-5 (2006). Recently tributlytin (TBT) and tetrabromobisphenol-A (TBBPA) have been reported to increase adipogenesis at least in part by serving as ligands for the transcription factor peroxisome proliferator activated receptor gamma (PPARγ). Other compounds reported to increase obesity rates such as bisphenol A (BPA) and dichlorodiphenyl-dichloroethylene (DDE), the major metabolite of the pesticide DDT, do not appear to be ligands of PPARγ suggesting that obesogens may have additional effects on adipogenesis and multipotent stem cell function. Grun et al., "Environmental Obesogens: Organotins and Endocrine Disruption Via Nuclear Receptor Signaling," *Endocrinology* 147(6 Suppl):550-5 (2006); Janesick et al., "Obesogens, Stem Cells and the Developmental Programming of Obesity," *Int J Androl* 35(3):437-48 (2012). Thus, a major knowledge gap is how obesogens act as environmental signals to alter the fate of MSCs by increasing differentiation into the adipocyte lineage. While obesogens are currently defined by their ability to increase adipogenesis, they also influence MSC and whole organism fate long after exposure and additionally may influence several generations of offspring. Developmental exposure to obesogens (in utero or neonatal) may have a profound effect on MSC fate, adipogenesis, and obesity throughout life. Epidemiological studies have provided evidence that early and prenatal exposure to environmental factors including BPA and DDE influence the adult risk of developing cancer and obesity. Boekelheide et al., "Predicting Later-Life Outcomes of Early-Life Exposures," *Environ Health Perspect* 120(10):1353-61 (2012). Given the dire rise in obesity, studies on obesogen exposure are urgently needed.

Another condition involving adipogenesis is thyroid eye disease (TED). TED is a disfiguring and sight-threatening autoimmune disease that involves inflammation of the orbit. TED has perplexed clinicians and scientists for decades. The increased scarring, especially of the extraocular muscles, and hyaluronan deposition along with substantial fat accumulation leads to protrusion of the eye (exophthalmos) and optic nerve compression. Bahn, R. S., "Graves' Ophthalmopathy," *N Engl J Med* 362(8):726-38 (2010); Kuriyan et al., "The Eye and Thyroid Disease," *Curr Opin Ophthalmol* 19(6):499-506 (2008). Why TED is manifested in nearly half of patients with Graves' hyperthyroidism, and with differing levels of severity or progression, remains unclear and are intriguing research questions requiring active investigation. To date, there is no effective treatment to prevent the destructive increase in orbital tissue. Bahn, R. S., "Graves' Ophthalmopathy," *N Engl J Med* 362(8):726-38 (2010). Furthermore, beyond supportive treatment and surgical procedures such as lid reconstruction, alleviation of muscle restriction, and orbital decompression, there is no reliable method to reverse or improve the debilitating outcomes of TED.

The present invention is directed to overcoming these and other deficiencies in the art.

SUMMARY OF THE INVENTION

A first aspect of the present invention relates to a method of treating a condition involving excessive adipogenesis. This method relates to selecting a subject having a condition involving excessive adipogenesis and administering to the selected subject a composition comprising a Thy1 protein or polypeptide fragment thereof, or an agent that enhances Thy1 expression, under conditions effective to treat the condition.

A second aspect of the present invention relates to an isolated nucleic acid molecule encoding a Thy1 protein or the fragment thereof according to the present invention.

A third aspect of the present invention relates to a pharmaceutical formulation. The formulation includes a Thy1 protein or polypeptide fragment thereof, or an agent that enhances Thy1 expression and a pharmaceutically acceptable carrier.

A fourth aspect of the present invention relates to a method of inhibiting adipogenesis and/or decreasing adipocyte size. This method includes providing a Thy1 protein or polypeptide fragment thereof, or an agent that enhances Thy1 expression; and contacting an adipocyte or adipocyte precursor with the Thy1 protein or polypeptide fragment thereof, or agent that enhances Thy1 expression thereby inhibiting adipogenesis and/or decreasing adipocyte size.

A fifth aspect of the present invention is directed to a method of screening a candidate compound for its ability to influence adipogenesis. This method includes contacting a cell capable of expressing Thy1 with a candidate compound; measuring the presence of or the amount of Thy1 expressed by the contacted cell, where a change in the level of Thy1 relative to the level of Thy1 in the cell in the absence of said candidate compound indicates that the candidate compound influences adipogenesis.

Thy1 (or Thy-1, also termed CD90) is an N-glycosylated, glycophosphatidylinositol (GPI)-anchored membrane protein that was originally identified as a surface marker on mouse T cells and thymocytes. Thy1 is a surface marker of unknown function that is expressed on some stem cells and some fibroblasts. While Thy1 was discovered more than 35 years ago, its molecular function remains a mystery. The inventors of the present application have discovered that Thy1 is more than a surface marker; rather, it can control the fate of cells by preventing adipogenesis. Among other things, it was found that soluble Thy1 can prevent human and mouse preadipocytes and primary human stem cells from becoming fat cells when given a proadipogenic cocktail containing a proliferator activated receptor gamma (PPARγ or PPARgamma) ligand. Similarly, deliberate genetic over-expression of Thy1 has the same effect, preventing cells from becoming adipocytes. As described in the Examples herein, several experiments support a direct role for Thy1 in preventing adipogenesis, including, inter alia, (1) depletion of Thy1 using Thy1 siRNA greatly enhances human stem cell adipogenesis; (2) introduction of Thy1 into an in vitro model of adipogenesis (mouse 3T3-L1 preadipocyte cells) dramatically reduces adipocyte formation; (3) introduction of Thy1 into stem cells or preadipocytes dramatically reduces expression of a PPARγ-dependent reporter gene; (4) over-expression of Thy1 in human stem cells inhibits adipogenesis; and (5) soluble recombinant Thy1 blunts human stem cell adipogenesis. These data indicate that Thy1 impairs adipogenesis and is an important for regulating PPARγ and adipogenesis.

As also described in the Examples herein, it was discovered that Thy1 can be regulated post-transcriptionally by a microRNA (miR-103 and miR-130). Interestingly, miR-103 is upregulated in obesity (Trajkovski et al., "MicroRNAs 103 and 107 Regulate Insulin Sensitivity," *Nature* 474 (7353):649-53 (2011), which is hereby incorporated by reference in its entirety), suggesting a further link regarding Thy1 expression, obesogens, and obesity. Furthermore, BPA, TBBPA, and TBT alter global gene expression and genomic methylation patterns of stem cells. While regulation of Thy1 expression in neuronal cells has been studied, the mechanisms whereby Thy1 expression is regulated in MSCs is almost completely unknown. Recent reports indicate that Thy1 expression can be regulated at the epigenetic level by methylation of the Thy1 promoter region (Sanders et al., "Epigenetic Regulation of Thy-1 by Histone Deacetylase Inhibitor in Rat Lung Fibroblasts," *Am J Respir Cell Mol Biol* 45(1):16-23 (2011), which is hereby incorporated by reference in its entirety). As described in more detail below, the inventors found that Thy1 expression is reduced in MSCs treated with the obesogens TBBPA, BADGE, and TBT. This experimental data provides surprising evidence that environmental obesogens reduce Thy1 expression in stem cells to increase adipogenesis at the expense of losing formation of other key effector cells such as osteocytes and myofibroblasts.

Further, the Examples described herein demonstrate that TED Thy1 negative (Thy1$^-$) orbital adipocytes produce more inflammatory cytokines and chemokines than non-orbital adipocytes when provoked by inflammatory mediators, and Thy1 regulates fibroblast fate in the orbit.

The present invention therefore provides surprising and significant advances in the regulation of adipogenesis and, inter alia, the treatment of conditions associated with excess adipogenesis (e.g., TED, obesity, and related metabolic disorders), which are major health problems requiring new therapeutic options.

BRIEF DESCRIPTION OF THE DRAWINGS

FIG. 1A is a schematic illustrating the Thy1 protein, showing major domain regions and glycosylation sites where Thy1 protein can be mutated/truncated according to the present invention. Phospholipase-C (PLC) can cleave the GPI-anchor creating a soluble Thy1. FIGS. 1B and 1C show the predicted structure of mature human Thy1 (FIG. 1B) and the predicted structure of mature human Thy1 protein with no glycosylation (FIG. 1C).

FIGS. 2A and 2B show sequences of Thy1 and fragments thereof according to the present invention. FIG. 2A shows a sequence alignment of human Thy1 (SEQ ID NO:1) and orthologs of human Thy1, including dog (SEQ ID NO: 2), cat (SEQ ID NO: 3), pig (SEQ ID NO: 4), mouse (SEQ ID NO: 5), rat (SEQ ID NO: 6), chicken (SEQ ID NO: 7), zebrafish (SEQ ID NO: 8), and *Xenopus* (SEQ ID NO: 9) Thy1. A consensus sequence of the aligned orthologs (SEQ ID NO: 10) is also shown. FIG. 2B shows a mature human Thy1 sequence (SEQ ID NO:1 without the signal sequence), as well as Thy1 polypeptide fragments according to the present invention, including Ac-QKVTSLTACLVDQSL-RLD (SEQ ID NO:11); CRHEN*TSSSPIQYEFSLTRE (SEQ ID NO:12); TKKHVLFGTVGVPEHTYRSRTN*FTS (SEQ ID NO:13); KYNMKVLYLSAFTSKDEGTYT (SEQ ID NO: 14); CALHHSGHSPPISSQN*VTVLRDKLVKC (SEQ ID NO: 15).

FIG. 3A is a graph of flow cytometric analysis showing expression of Thy1 in Thy1 lentivirus (LV)-treated but not control cells. FIGS. 3B and 3C are images of Oil-red-O staining that show abundant lipid droplet formation in control cells, but not in Thy1+ cells. FIG. 3D is a bar graph of results showing that lipid content was diminished by 80% in 3T3-L1 Thy1 cells compared to control. (*=p<0.01, Student's T test). FIG. 3E shows results of western blot analysis of Thy1, FABP4, and β-tubulin on adipogenic day 5. As shown, FABP4 expression was inhibited by Thy1 expression. FIG. 3F is a graph of results of adipogenesis measured via fluorescence using AdipoRed staining and shows that Thy1 over-expression significantly inhibits adipogenesis. FIG. 3G is a graph of results of PPARγ activity measured via a peroxisome proliferator response element (PPRE)-driven luciferase assay, demonstrating that Thy1 inhibits PPARγ activity.

As shown in FIG. 4A, all cocktails containing obesogens induced FABP4. The same samples as in FIG. 4A were used to measure Thy1 mRNA levels by qPCR and the results shown in FIG. 4B. As shown in FIG. 4B, obesogens and control cocktail decreased Thy1 mRNA levels. Thy1 and FABP4 levels were normalized to TBP mRNA levels (control gene). hMSCs were also treated with vehicle (DMSO), 20 uM TBBPA, or 10 uM rosiglitazone for 72 hrs, harvested and stained with a fluorescent anti-Thy1 antibody for analysis of Thy1 by flow cytometry. The results of flow cytometric analysis are shown in FIG. 4C and demonstrated that the surface expression of Thy1 is decreased by treatment with either TBBPA (solid black line) or rosiglitazone (dotted line) compared to vehicle treated cells (gray shade).

FIG. 5B is a bar graph showing the mean fluorescent intensity (MFI) of Thy1 surface expression from FIG. 5A. The same samples as in FIG. 5A were used to measure Thy1 mRNA levels by qPCR. Thy1 mRNA levels were normalized to TBP mRNA levels (control gene). These results shown in FIG. 5C demonstrate that Thy1 expression is reduced by miR-103.

FIG. 6A is a bar graph showing the results of flow cytometric analysis. In particular, Mean Fluorescent Intensity (MFI) shows a dramatic reduction in Thy1 surface expression in TBBPA (5 μM) exposed samples (*p<0.05, error bars represent S.D.). FIG. 6B shows the results of western blotting, demonstrating a reduction in Thy1 after treatment with the obesogens, TBBPA and TBT (concentrations in figure). FIG. 6C is a bar graph showing quantitation of Thy1 levels from FIG. 6B (Thy1 levels were normalized to β-tubulin levels).

FIG. 7A shows a model of thyroid eye disease development and outcomes. FIG. 7B is a diagram illustrating that activated T cells and mast cells produce pro-adipogenic prostaglandins resulting in TED adipogenesis only in the Thy1-orbital fibroblast subset.

FIG. 9A is a bar graph showing Thy1 mRNA relative expression levels after treatment of orbital fibroblasts with Thy1 siRNA. The results shown in FIG. 9A show that treatment of orbital fibroblasts with Thy1 siRNA reduces Thy1 mRNA expression to about 5% of control siRNA-treated samples. FIG. 9B is a graph showing the results of flow cytometry analysis of Thy1 surface expression of cells as in FIG. 9A. These results demonstrate that Thy1 siRNA dramatically reduces Thy1 surface expression. FIG. 9C shows the results of an AdipoRed assay measuring lipid accumulation in fibroblasts treated as in FIG. 9A. These results demonstrate that Thy1 siRNA-treated samples accumulate significantly more lipid than control. (Mean+Std. Error. **p<0.01 by Student's t-test.)

As shown in FIG. 10A, orbital stromal fibroblasts express Thy1, while orbital adipocytes do not. FIG. 10B shows results of Thy1 mRNA analysis by real-time PCR, demonstrating that adipocyte Thy1 mRNA levels from orbit, eyelid, and visceral fat were less than 5% of stromal fibroblast samples. FIG. 10C shows results of analysis of orbital adipocyte and orbital scar tissue samples by western blot. As shown in FIG. 10C, Thy1 protein is not detectable in human orbit fat. (*=p<0.01) These data demonstrated that Thy1 is not expressed in human adipocytes from orbit, eyelid or visceral fat tissue.

FIG. 11A shows results of Oil-red-O staining. These results show lipid accumulation of 3T3-L1 throughout experiment. FIG. 11B shows results of Thy1, fatty acid binding protein 4 (FABP4), and adipose-differentiation related protein (ADRP) mRNA analysis by real-time PCR. As shown, Thy1 mRNA levels decreased rapidly upon administration of adipogenic medium and were below 10% of control levels by Day 5. FIG. 11C shows results of western blot analysis of Thy1, FABP4, and b-tubulin (loading control). As shown, Thy1 levels were undetectable by Day 8. These data demonstrated that Thy1 expression is lost during adipogenesis of 3T3-L1 preadipocytes.

FIG. 12A shows the results of western blot analysis, which demonstrates that Thy1 expression was reduced by Thy1 siRNA to less than 20% of control treated cells. Cell images were captured to show the presence of lipid droplets in fibroblasts treated with adipogenic medium and are shown in FIG. 12B. Visual inspection revealed significantly more adipocytes in Thy1 siRNA treated cells compared to control. FIGS. 12C and 12D shown the results of western blot analysis of FABP4 and β-tubulin (loading control) levels. FABP4 expression was increased by 80% in cells treated with adipogenic medium and Thy1 siRNA compared to control. FABP4 mRNA and 18S rRNA (normalization control) levels were measured by RT-qPCR and the results shown in FIG.

12E. As shown, FABP4 mRNA levels were increased by 2.4 fold in cells treated with the adipogenic medium and Thy1 siRNA compared to the corresponding control. Lipid accumulation from cells treated as above were measured using the AdipoRed assay and the results shown in FIG. 12F. As shown, lipid accumulation was increased by 60% in cells treated with the adipogenic medium and Thy1 siRNA compared to control. Experiments were performed in at least three different human fibroblast strains and results are from a representative strain repeated in triplicate. (*=p<0.01, Student's T test).

Figures 13A, 13B, 13C:
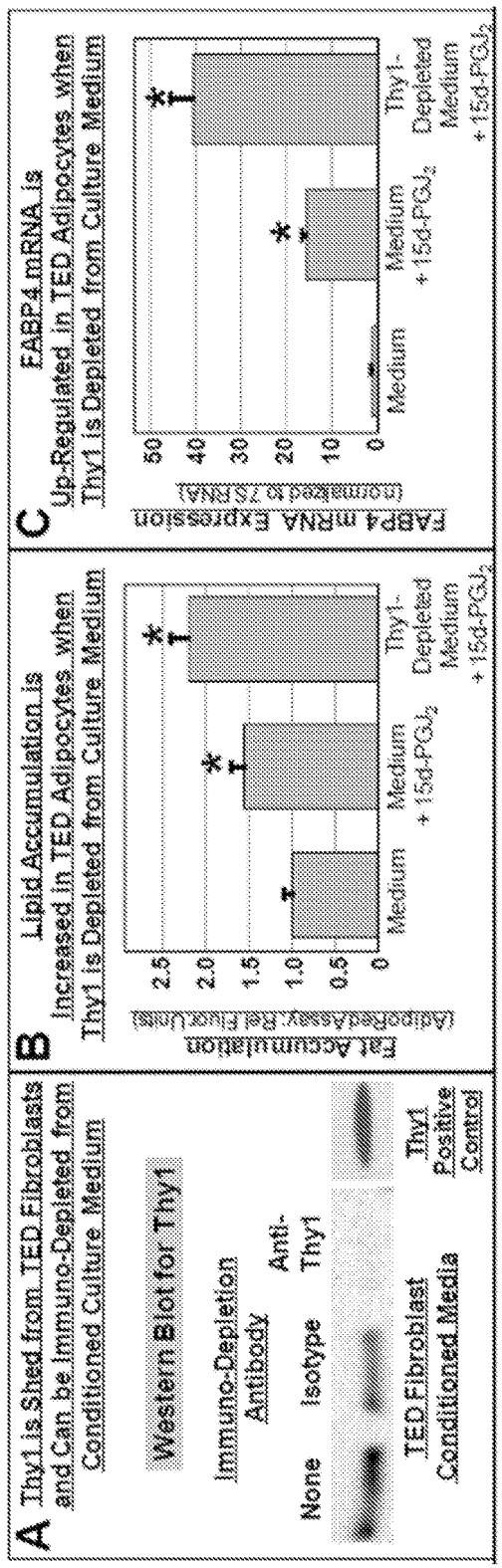

FIGS. 13A-13C show experimental results demonstrating that depletion of soluble Thy1 from culture medium increases adipogenesis and FABP4 expression in TED adipocytes. FIG. 13A shows the results of western blot analysis demonstrating soluble Thy1 present in Thy1+ orbital fibroblast conditioned medium can be depleted by incubation with a specific anti-Thy1 antibody but not an isotype control antibody. TED cell extract serves as a positive control. FIG. 13B is a bar graph of results of AdipoRed analysis of TED adipocytes cultured in Thy1-depleted conditioned medium showing enhanced adipogenesis. FIG. 13C is a bar graph of results showing that FABP4 mRNA expression is also remarkably increased when Thy1 is depleted from conditioned media. (*p<0.01 by Student's t-test.)

Figures 14A, 14B, 14C:
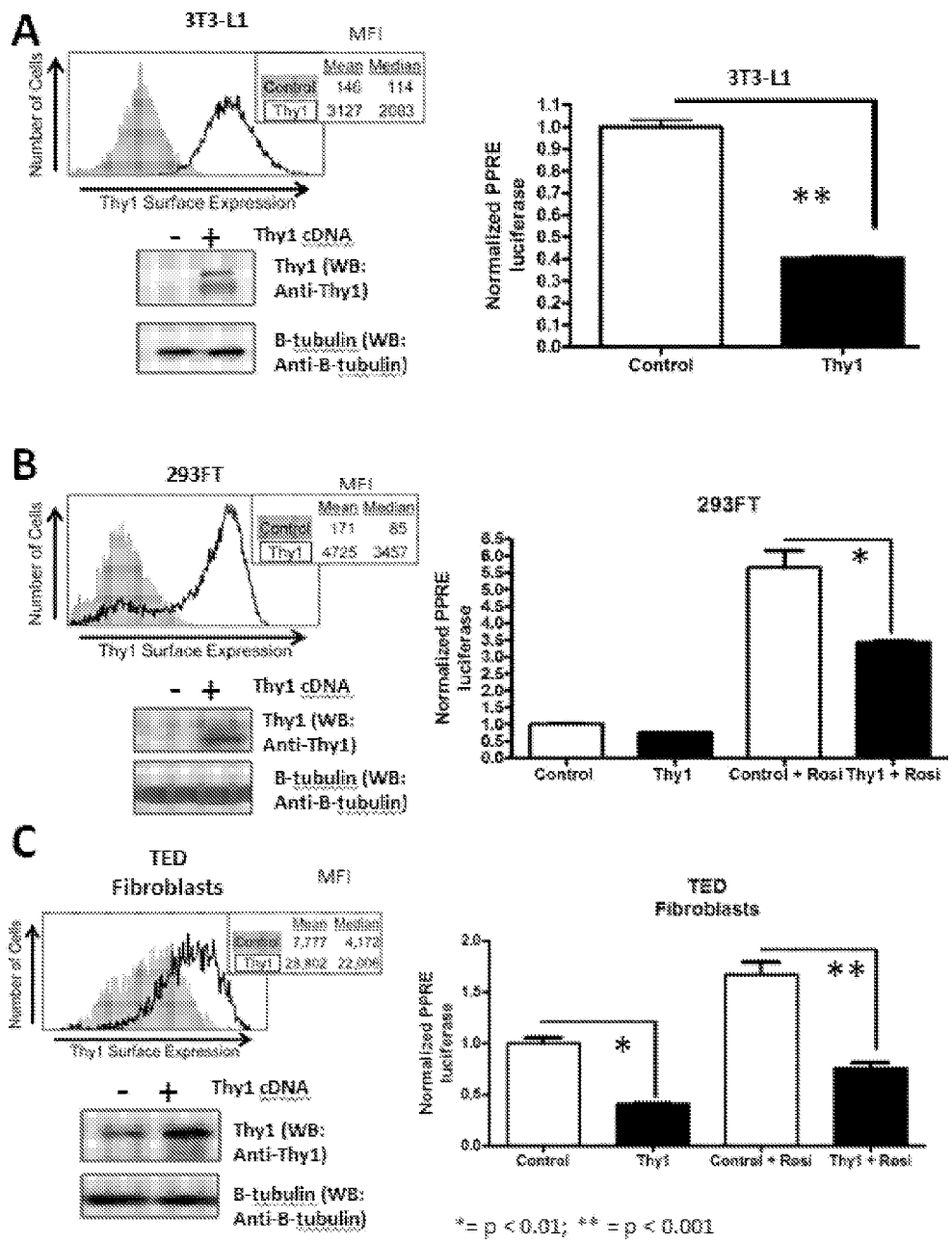

FIGS. 14A-14C show the results of experiments demonstrating that Thy1 expression inhibits activity of the master adipogenic regulator, PPARγ. The activity of the key adipogenic transcription factor, PPARγ was measured in various cells type using a PPARγ response element (PPRE×3)-luciferase reporter. In the cell types tested, Thy1 expression reduced PPARγ activity. Thy1 cDNA or a control plasmid along with the PPRE×3-luc and control SV40-renilla reporter plasmids were introduced into 3T3-L1 cells via electroporation. Expression of Thy1 was confirmed by western blot and flow cytometry. Introduction of Thy1 reduces PPARγ activity by approximately 60% compared to control 3T3-L1 cells, as shown in FIG. 14A. HEK293FT cells were treated as in FIG. 14A with the addition a plasmid encoding PPARγ (pcDNA3.1-PPARγ). HEK293FT cells were then treated with vehicle (DMSO) or 100 nM of a synthetic PPARγ ligand, rosiglitazone (rosi). In both treatments, Thy1 expression reduces PPARγ activity. (*=p<0.01, Student's T test), as shown in FIG. 14B. Human pre-adipocyte fibroblasts were treated as in FIG. 14A and then treated with DMSO or 100 nM rosi. Thy1 expression reduces the activity of PPARγ, as shown in FIG. 14C. Results are from experiments repeated in triplicate and represented as normalized average luciferase activity+standard error. (*=p<0.01 and **=p<0.001, Student's T test).

Figures 15A, 15B:
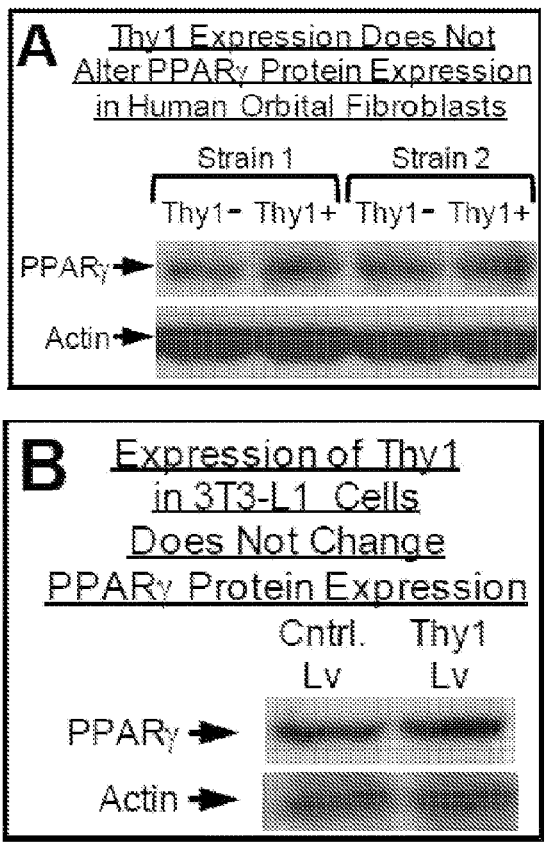

FIGS. 15A and 15B show experimental results of western blot analysis demonstrating that Thy1 expression does not affect PPARγ protein levels. Orbital fibroblasts from two individual human donors were separated into Thy1⁻ and Thy1+ subsets. Cells were harvested and analyzed by western blotting for PPARγ and actin (loading control). FIG. 15A shows results that demonstrate there is not a significant difference in PPARγ protein levels in either subset. In addition, 3T3-L1 cells were transduced with control or human Thy1− encoding lentiviral (Lv) particles. After 48 hours, cells were harvested and analyzed as in FIG. 15A and the results shown in FIG. 15B. As shown in FIG. 15B, introduction of human Thy1 does not significantly affect PPARγ expression.

Figure 16:
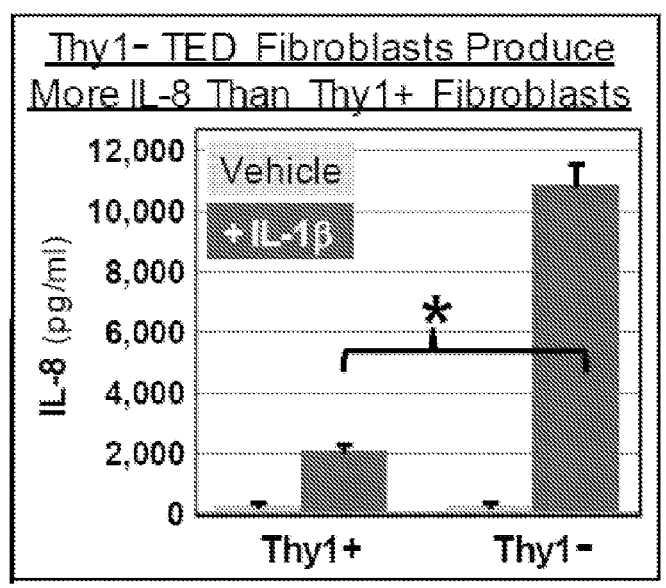

FIG. 16 is a bar graph of experimental results demonstrating that Thy1⁻ TED fibroblasts produce more IL-8 than Thy1+ fibroblasts. Graves' orbital fibroblasts were isolated from tissue following decompression surgery and then sorted by FACS to Thy1+ and Thy1⁻ subsets. The Thy1⁻ orbital fibroblasts produced 6-fold more IL-8 than Thy1+ fibroblasts following culture with IL-1β treatment (10 ng/ml). (Mean+Std. Error. *p<0.01 by Student's t-test.)

Figures 17A, 17B:
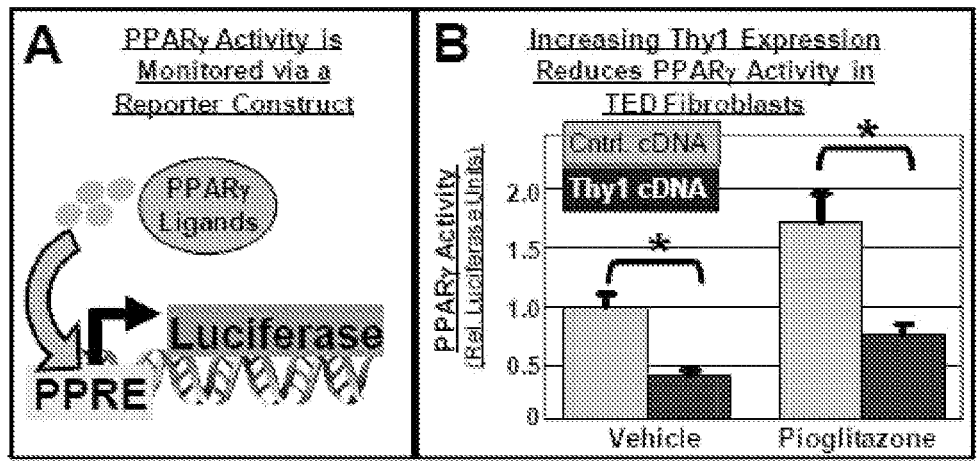

FIGS. 17A and 17B show a schematic diagram of a PPARγ activity-dependent luciferase reporter (FIG. 17A) and a bar graph of experimental results demonstrating that PPARγ transcriptional activity is decreased in cells expressing Thy1 cDNA (FIG. 17B). In particular, Thy1 cDNA was introduced into cells containing a PPRE-luciferase reporter and a control Renilla reporter. Cells were treated with vehicle or a synthetic PPARγ ligand, pioglitazone (15d-PGJ2 gave similar results). PPRE-luciferase activity was normalized to Renilla activity. In both treatments, Thy1 expression reduced PPARγ activity. (Mean+s.d. *p<0.01 by Student's t-test.) The results are shown in FIG. 17B and demonstrate that introduction of Thy1 cDNA reduces PPARγ activity.

Figures 18A, 18B:
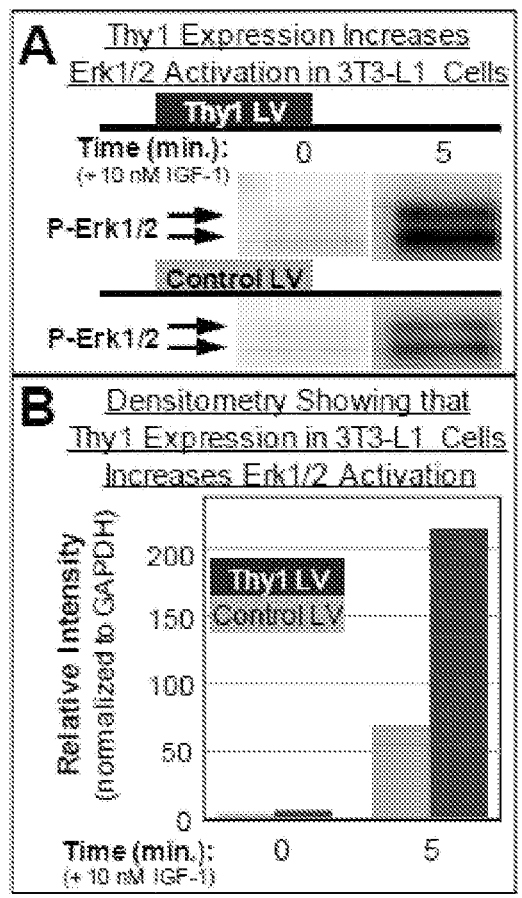

FIGS. 18A and 18B show experimental results demonstrating that Erk 1/2 activity is enhanced in cells expressing Thy1. 3T3-L1 cells infected with a control or Thy1-expressing lentivirus (LV) were treated with 10 nM insulin-like growth factor (IGF)-1 for 0, 5, or 10 minutes. Cells were treated as described, then whole cell lysates were harvested and analyzed by western blot for phospho-Erk1/2 and GAPDH expression (FIG. 18A). Western blot images were analyzed by densitometry and phospho-Erk1/2 levels were normalized to GAPDH to adjust for total protein variations (FIG. 18B). Densitometric analysis shows a tremendous up-regulation of phosphorylated Erk1/2 when Thy1 is overexpressed.

Figures 19A, 19B:
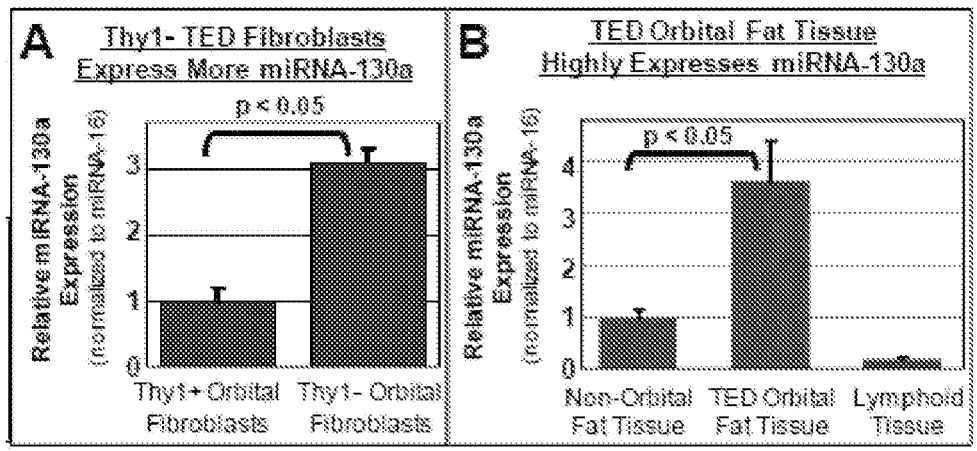

FIGS. 19A and 19B show experimental results demonstrating that miRNA-130a is highly expressed by Thy1⁻ fibroblasts compared to Thy1+ fibroblasts (FIG. 19A), and there is more miRNA-130a expression in orbital fat tissue compared to other fat tissues or to a non-fat lymphoid tissue (FIG. 19B). (p<0.05 by Student's t-test.)

Figures 20A, 20B:
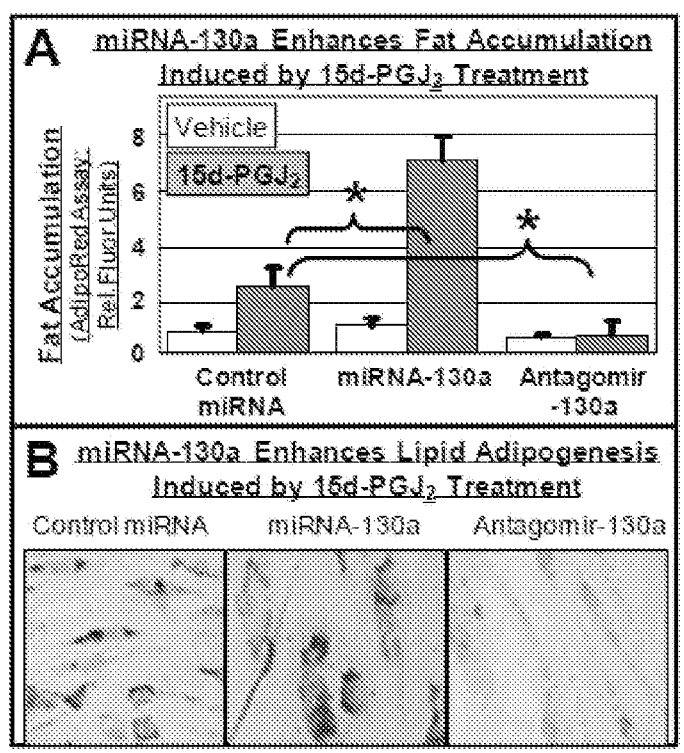

FIGS. 20A and 20B show experimental results demonstrating that miRNA-130a is essential for adipogenesis of TED orbital fibroblasts. FIG. 20A is a bar graph showing results of an AdipoRed assay measuring lipid accumulation in fibroblasts exposed to vehicle or 15d-PGJ2 and treated with control, miRNA-130a, or antagomir-130a (a miRNA inhibitor). As shown by oil red O staining in FIG. 20B, treatment of orbital fibroblasts with ectopic miRNA-130a greatly enhances adipogenesis, while treatment with antagomir-130a inhibits adipogenesis. (*p<0.05 by Student's t-test.)

Figures 21A, 21B, 21C:
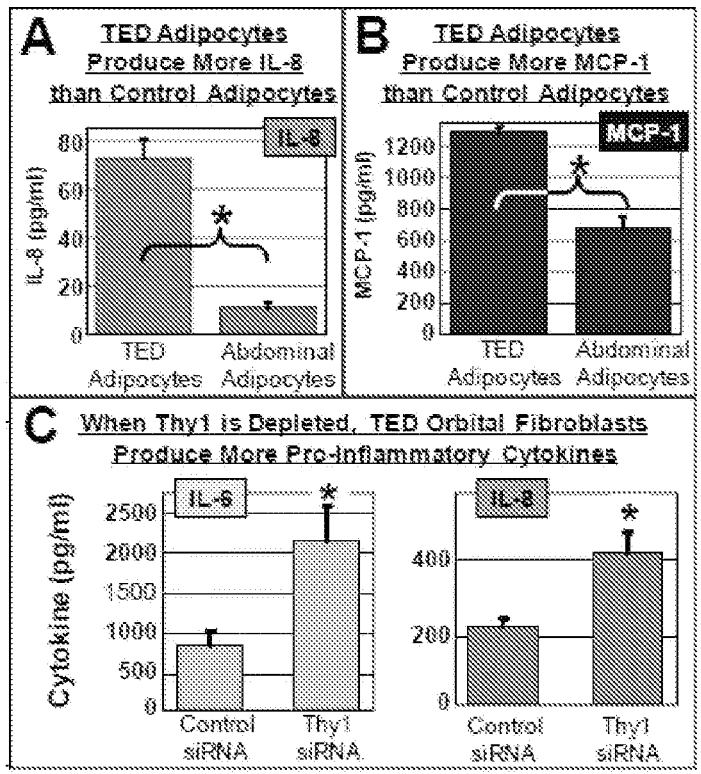

FIGS. 21A-21C are bar graphs of experimental results demonstrating that TED orbital adipocytes (a heterogeneous mix of Thy1+ and Thy1⁻) produce more inflammatory cytokines than abdominal adipocytes, indicating the unique and pathologic phenotype of TED adipocytes. Compared to abdominal adipocytes, TED adipocytes release significantly more IL-8 (FIG. 21A) and MCP-1 (FIG. 21B). Thy1 depletion increases inflammatory cytokine production from TED fibroblasts. Following transfection with a Thy1 siRNA to deplete Thy1 protein expression, IL-6 and IL-8 production increases (FIG. 21C). (Mean+Std. Error. *p<0.01 by Student's t-test.)

Figure 22:
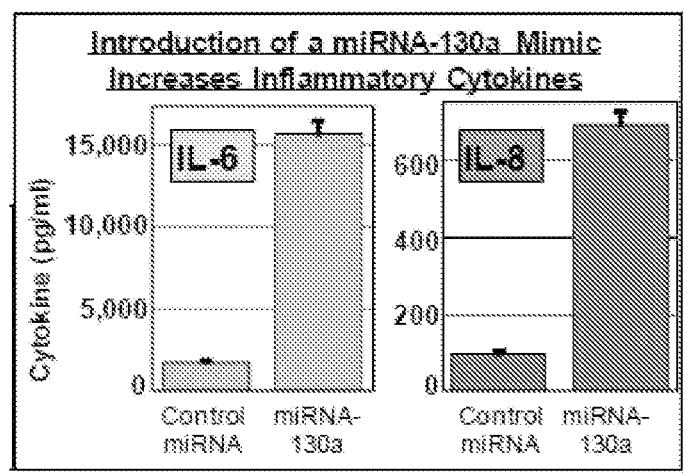

FIG. 22 is a bar graph of experimental results demonstrating that introduction of an exogenous miRNA-130a mimic, which greatly increases the expression of miRNA-130a, in TED adipocytes increases inflammatory cytokine levels. Either a control or a miRNA-130a mimic was introduced into TED adipocytes. Culture media was harvested and analyzed for IL-6 and IL-8 content, which showed increased production of the pro-inflammatory mediators when the miRNA-130a mimic was present. (Mean+Std. Dev.)

Figures 23A, 23B, 23C:
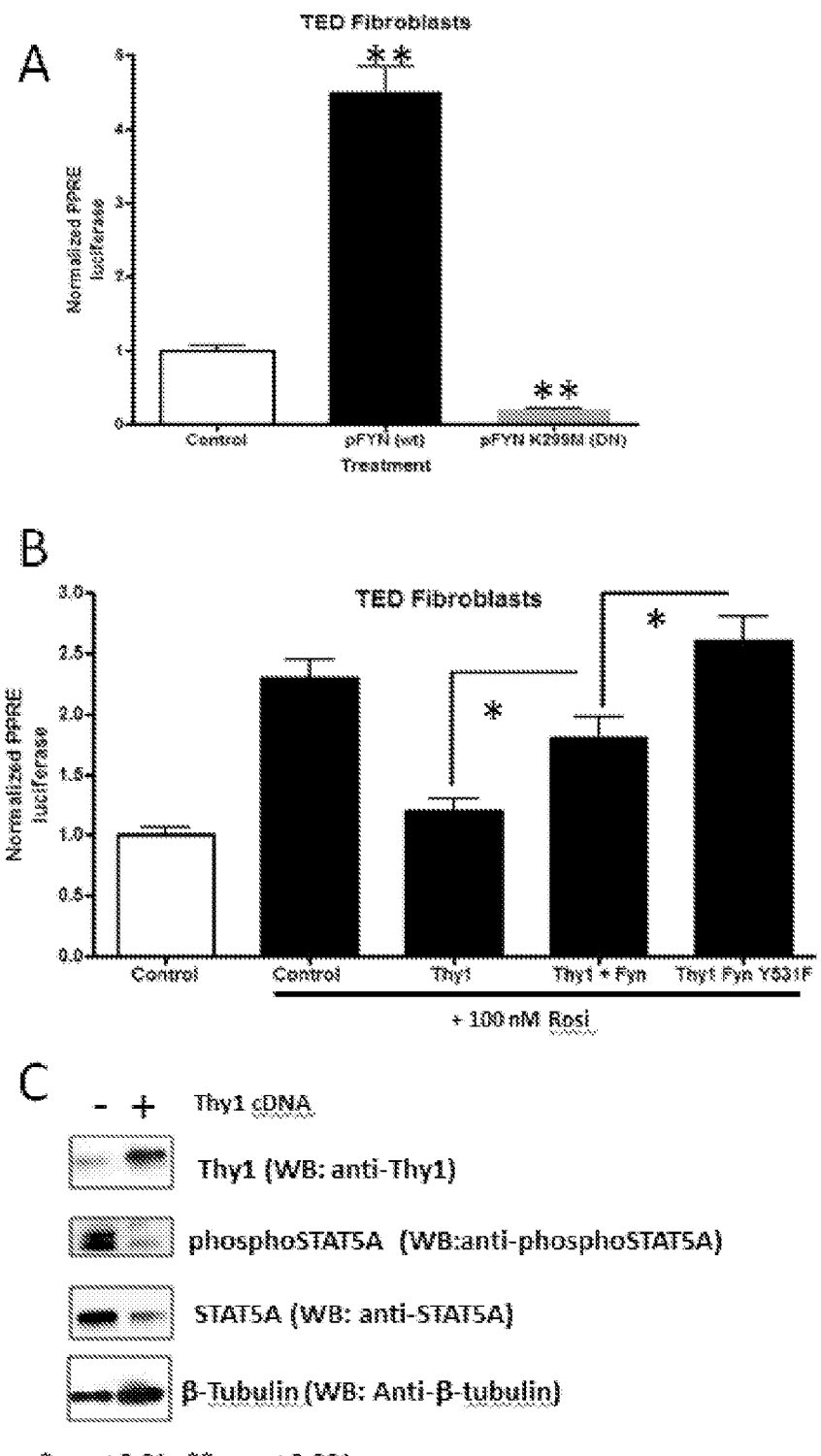

FIGS. 23A-23C show experimental results demonstrating that Thy1 regulates the activity of PPARγ through Fyn in human pre-adipocyte fibroblasts. The PPREx3-luc and control SV40-renilla reporter plasmids were introduced into human pre-adipocyte fibroblasts along with a control plasmid (pXL6) or plasmids that express either wild-type Fyn (pRK5-Fyn) or a kinase dead, dominant negative Fyn (pRK5-Fyn K299M). As shown in FIG. 23A, ectopic expression of Fyn results in a 4.5 fold increase in PPARγ transcriptional activity. Expression of dominant negative Fyn results in a greater than 70% reduction in PPARγ transcriptional activity. In FIG. 23B, in addition to the reporter constructs, the following expression plasmids were introduced: pXL6-empty control (columns 1 and 2), pXL6-hThy1 (column 3), pRK5-Fyn (column 4), and a constitutively active Fyn mutant reporter plasmid, pRK5-Fyn Y531F (column 5). As shown in FIG. 23B, Thy1 expression reduced PPARγ activity by 50% (column 2 vs 3) while introduction of wild-type Fyn restored approximately 40% of control PPARγ activity (column 2 vs 4). Introduction of Fyn-Y531F increased PPARγ activity to over 100% of control (column 2 vs 5). Experiments were performed in at least two different strains and results are from a representative strain repeated in triplicate. FIG. 23C shows results demonstrating that Thy1 expression inhibits Fyn mediated phosphorylation of STAT5. In particular, western blotting shows that Thy1 expression reduces phospho-STAT5 levels, demonstrating an inhibition of Fyn activity. These data demonstrate that Thy1 regulates the activity of PPARγ through Fyn in human pre-adipocyte fibroblasts.

Figures 24A, 24B, 24C, 24D, 24E:
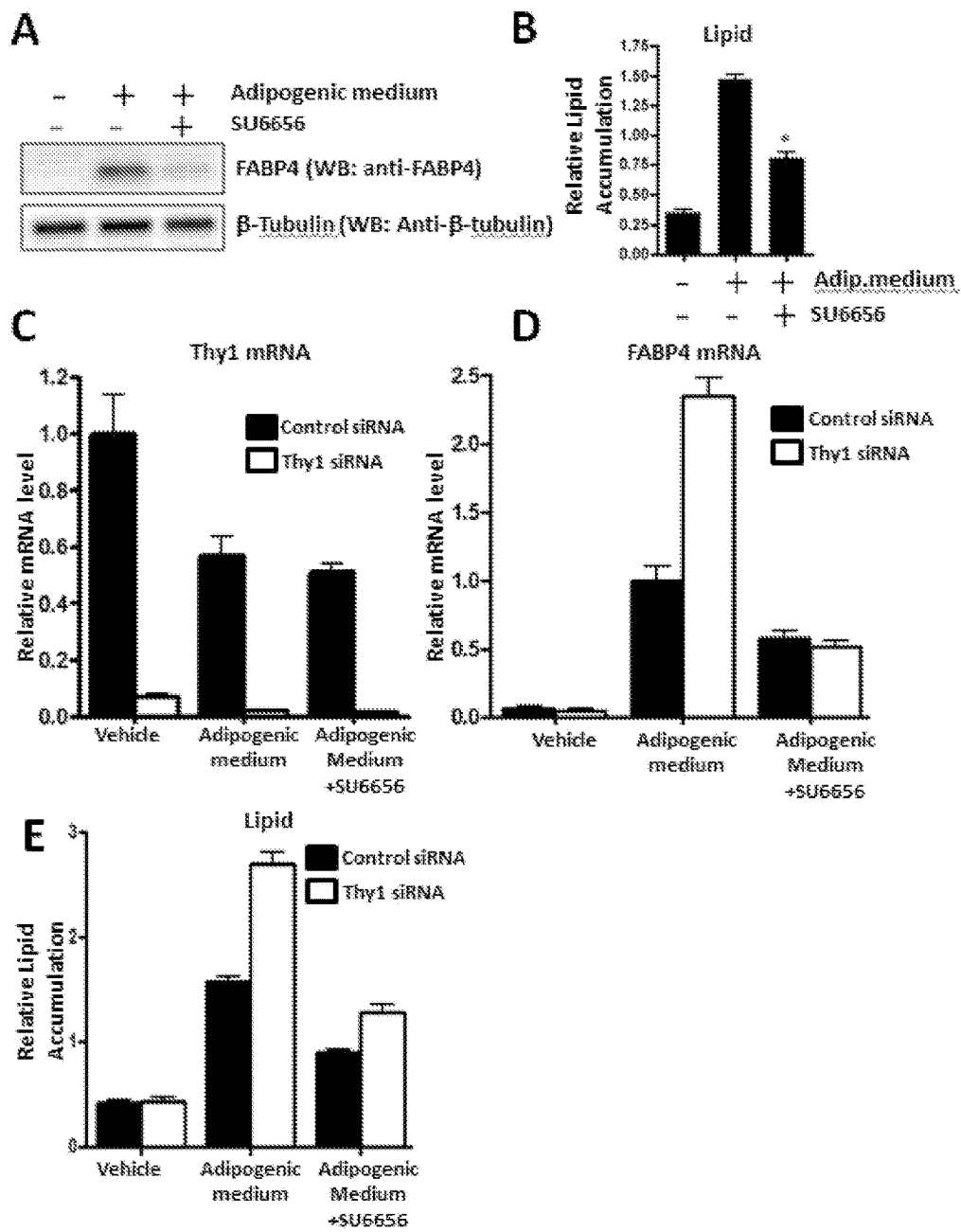

FIGS. 24A-24E show experimental results demonstrating that Thy1 regulates adipogenesis by inhibiting the activity of Fyn. Human primary pre-adipocyte fibroblasts were induced to differentiate into adipocytes with or without SU6656, a selective Fyn inhibitor. FIG. 24A shows the results of western blot analysis demonstrating that SU6656 decreases FABP4 protein expression to 30% of control. FIG. 24B shows results demonstrating that SU6656 decreased lipid accumulation to 55% of control. FIGS. 24C-24E show results of an experiment in which Thy1 specific or control siRNA were introduced into fibroblasts followed by adipocyte induction with or without SU6656. FABP4 mRNA expression (FIG. 24D) and lipid accumulation (FIG. 24E) were increased in cells treated with Thy1 siRNA. SU6656 treatment ablated the adipogenic effect of Thy1 siRNA. These data demonstrate that Thy1 regulates adipogenesis by inhibiting the activity of Fyn.

DETAILED DESCRIPTION OF THE INVENTION

Figure 1A:
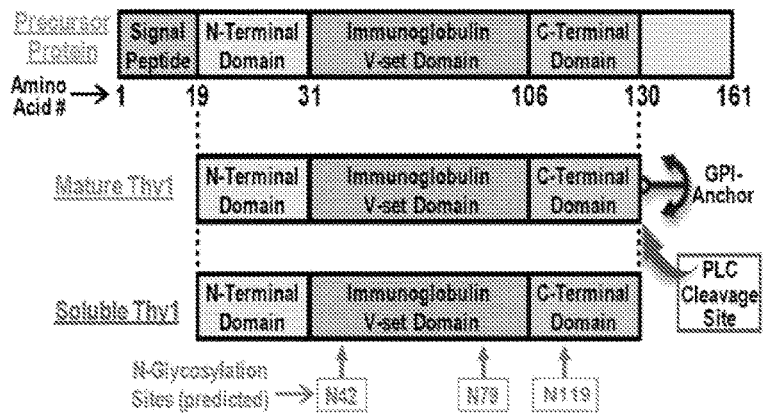
FIGS. 1A-1C are schematic diagrams showing Thy1 protein.
Figure 1B:
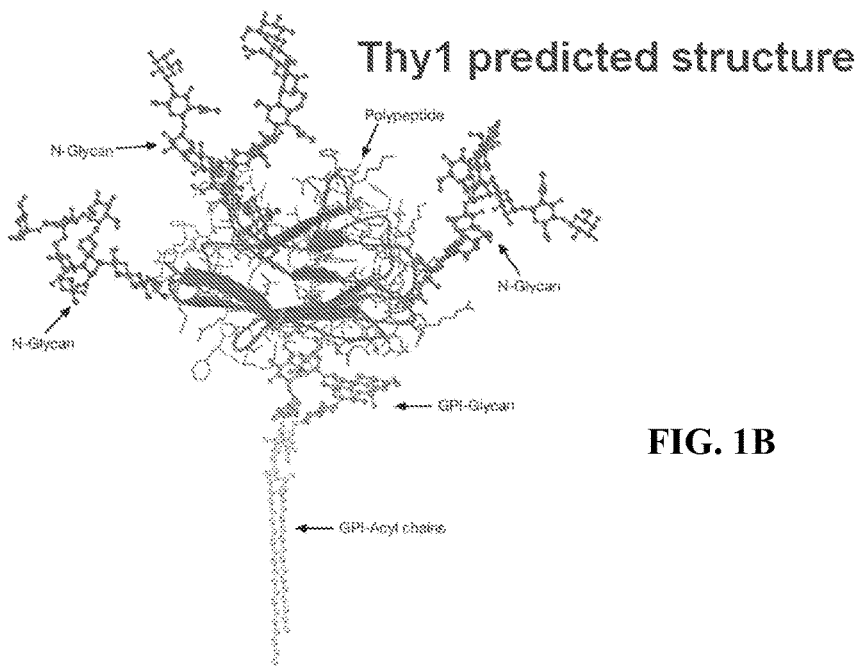
Figure 1C:
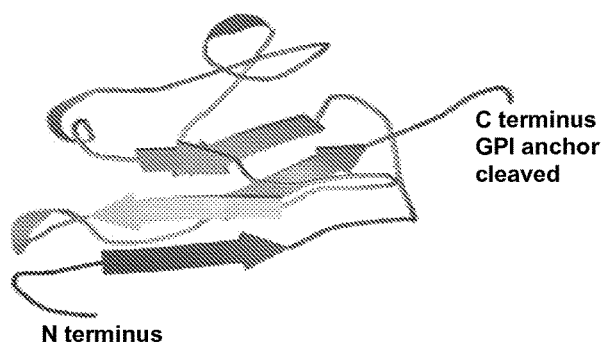

Thy1 (or Thy-1, also termed CD90) is an N-glycosylated, glycophosphatidylinositol (GPI)-anchored membrane protein and is a 25-37 kDa member of the Ig supergene family. The domain architecture of Thy1 is shown in FIG. 1A and predicted structure of Thy1 is shown in FIGS. 1B and 1C. The inventors of the present application have pioneered the classification of fibroblast subsets based on expression of the cell surface marker, Thy1. Phipps et al., "Characterization of Two Major Populations of Lung Fibroblasts: Distinguishing Morphology and Discordant Display of Thy1 and Class II MHC," *Am J Respir Cell Mol Biol* 1(1):65-74 (1989), which is hereby incorporated by reference in its entirety. Thy1 resides on the surface of some fibroblasts, myofibroblasts, and stem cells. Baglole et al., "More Than Structural Cells, Fibroblasts Create and Orchestrate the Tumor Microenvironment," *Immunol Invest* 35(3-4):297-325 (2006); Bradley et al., "Roles and Regulation of Thy1, a Context-Dependent Modulator of Cell Phenotype," *Biofactors* 35(3):258-65 (2009); and Pei et al., "Thy-1 Distinguishes Human Corneal Fibroblasts and Myofibroblasts from Keratocytes," *Exp Eye Res* 79(5):705-12 (2004), each of which is hereby incorporated by reference in its entirety. Only Thy1 negative (Thy1−) fibroblasts have adipogenic potential. Koumas et al., "Thy-1 Expression in Human Fibroblast Subsets Defines Myofibroblastic or Lipofibroblastic Phenotypes," *Am J Pathol* 163(4):1291-300 (2003) and Koumas et al., "Fibroblast Subsets in the Human Orbit: Thy-1+ and Thy-1− Subpopulations Exhibit Distinct Phenotypes," *Eur J Immunol* 32(2):477-85 (2002), each of which is hereby incorporated by reference in its entirety. Thy1 positive (Thy1+) cells are more prone to form myofibroblasts and deposit ECM material, such as collagen. Guo et al., "Mast Cell-Derived Prostaglandin D2 Controls Hyaluronan Synthesis in Human Orbital Fibroblasts Via Dp1 Activation: Implications for Thyroid Eye Disease," *J Biol Chem* 285 (21):15794-804 (2010) and Koumas et al., "Thy-1 Expression in Human Fibroblast Subsets Defines Myofibroblastic or Lipofibroblastic Phenotypes," *Am J Pathol* 163(4):1291-300 (2003), each of which is hereby incorporated by reference in its entirety. The inventors of the present invention have now discovered that Thy1 controls the fate of progenitor cells to prevent adipogenesis and that Thy1 protein or polypeptide fragments thereof can be administered to halt and reverse adipogenesis, thereby treating associated disorders. Further, other agents that can enhance native Thy1 expression can also be administered to halt and reverse adipogenesis via Thy1, thereby treating the associated disorder.

Accordingly, one aspect of the present invention relates to a method of treating a condition involving excessive adipogenesis. This method relates to selecting a subject having a condition involving excessive adipogenesis and administering to the selected subject a composition comprising a Thy1 protein or polypeptide fragment thereof, or an agent that enhances Thy1 expression, under conditions effective to treat the condition.

The above-identified therapeutic treatments can also be used in combination with one or more current therapies, which will be known to those of ordinary skill in the art based on the particular condition(s) to be treated.

The patients to be treated in accordance with the present invention can have varying degrees of severity of the condition. Consequently, it is expected that the degree of symptom control can constitute preventing further development of symptoms or a reduction in the severity of symptoms.

The Thy1 protein or polypeptide fragment thereof may be derived from a mammal. For example, the Thy1 protein may be derived from human Thy1 or a rodent Thy1.

In one embodiment, the Thy1 protein comprises or consists of the amino acid sequence of SEQ ID NO:1 (GENBANK Accession No. AAA61180, which is hereby incorporated by reference in its entirety), as follows:

(SEQ ID NO: 1)
MNLAISIALL LTVLQVSRGQ KVTSLTACLV DQSLRLDCRH

ENTSSSPIQY EFSLTRETKK HVLFGTVGVP EHTYRSRTNF

-continued

```
TSKYHMKVLY LSAFTSKDEG TYTCALHHSG HSPPISSQNV

TVLRDKLVKC EGISLLAQNT SWLLLLLLSL SLLQATDFMS

L
```

In another embodiment, the Thy1 protein may be an ortholog of human Thy1. Suitable orthologs include, but are not limited to, dog, cat, pig, mouse, rat, chicken, zebrafish, or *Xenopus* Thy1 (see FIG. 2A; SEQ ID NOs: 2-9, respectively). The Thy1 protein or polypeptide fragment thereof may be derived from a consensus sequence such as one comprising or consisting of SEQ ID NO:10 shown in FIG. 2 or SEQ ID NO: 32 (– represents a gap), as follows:

```
MNP[A/T/V/F]ISIALLLTVLQVARGQKVTSLTACLV[D/N/G/K/R]

QS[-/N/P][-/K]LRLDCRHEN[T/A/S/N/K]T[S/T/N/K/D]

[-/D/K][S/L/N/D/K]PIQYEFSLTREKKKHVI[F/Y/L/S/Q/G]

GTVGVP[-/T/F][-/P/F]RHTYRSR[T/V/A/]N[F/L/V/P]TS

[K/Q/D/H/T][Y/P/R/K/D]NIKVLYLSGFTTKDEG

[T/M/I/D/V/N/L]YTCEL[H/R/Q/K/F]LSG[H/Q/A/D/S]

[S/P/T/N/Y/L]P[-/P/I/T/S/M/G/I][-/I/T/S/N]

SSKNITVLRDKLVKC
```

In certain embodiments according to the present invention, the Thy1 protein of the present invention includes a polypeptide sequence that has at least 70%, at least 75%, at least 80%, at least 85%, at least 90%, at least 95%, at least 97%, or at least 99% amino acid sequence identity to the amino acid sequence of SEQ ID NO:1.

The present invention also includes Thy1 polypeptide fragments. The term "fragment" when used herein with respect to a given polypeptide sequence, refers to a contiguous stretch of amino acids of the given polypeptide's sequence that is shorter than the given polypeptide's full-length sequence. A portion of a given polypeptide may be defined by its first position and its final position, in which the first and final positions each correspond to a position in the sequence of the given full-length polypeptide. The sequence position corresponding to the first position is situated N-terminal to the sequence position corresponding to the final position. The sequence of the fragment is the contiguous amino acid sequence or stretch of amino acids in the given polypeptide that begins at the sequence position corresponding to the first position and ending at the sequence position corresponding to the final position. A portion may also be defined by reference to a position in the given polypeptide sequence and a length of residues relative to the referenced position, whereby the sequence of the portion is a contiguous amino acid sequence in the given full-length polypeptide that has the defined length and that is located in the given polypeptide in reference to the defined position.

The Thy1 polypeptide or fragment thereof can also be present as part of a fusion protein. For instance, the Thy1 polypeptide or fragment thereof the may be fused to a protein partner that confers a longer half-life to the protein upon in vivo administration. Suitable fusion partners include, without limitation, immunoglobulins (e.g., the Fc portion of an IgG), human serum albumin (HSA) (linked directly or by addition of the albumin binding domain of streptococcal protein G), fetuin, or a fragment of any of these. The Thy1 polypeptide or fragment thereof may also be fused to a macromolecule other than protein that confers a longer half-life to the protein upon in vivo administration.

Suitable macromolecules include, without limitation, polyethylene glycols (PEGs). Methods of conjugating proteins or peptides to polymers to enhance stability for therapeutic administration are described in U.S. Pat. No. 5,681,811 to Ekwuribe, which is hereby incorporated by reference in its entirety. Nucleic acid conjugates are described in U.S. Pat. No. 6,528,631 to Cook et al., U.S. Pat. No. 6,335,434 to Guzaev et al., U.S. Pat. No. 6,235,886 to Manoharan et al., U.S. Pat. No. 6,153,737 to Manoharan et al., U.S. Pat. No. 5,214,136 to Lin et al., or U.S. Pat. No. 5,138,045 to Cook et al., which are hereby incorporated by reference in their entirety. The fusion protein may optionally contain two or more of the Thy1 polypeptides or fragments thereof.

The Thy1 polypeptide fragments may be derived from an amino acid sequence of a mammalian Thy1 polypeptide. Thy1 polypeptide fragments may be derived from an amino acid sequence of a human Thy1 polypeptide. The Thy1 polypeptide fragments may be derived from the amino acid sequence of Thy1, as described above (e.g., SEQ ID NO:1). Thy1 polypeptide fragments may be derived from an amino acid sequence of an ortholog of human Thy1 polypeptide. As noted above, suitable orthologs include, but are not limited to, dog, cat, pig, mouse, rat, chicken, zebrafish, or *Xenopus* Thy1 (see FIG. 2A; SEQ ID NOs: 2-9, respectively). The Thy1 polypeptide fragments may be derived from a consensus sequence such as a sequence comprising or consisting of SEQ ID NO: 10 shown in FIG. 2 or SEQ ID NO: 32 described above. Thy1 polypeptide fragments derived from an ortholog of human Thy1 or consensus sequence include fragments corresponding to the fragments of human Thy1 (SEQ ID NO:1) described herein. Corresponding portions or fragments may be determined by, for example, sequence analysis and structural analysis.

In certain embodiments according to the present invention, the polypeptide fragment of Thy1 protein of the present invention includes a polypeptide sequence that has at least 70%, at least 75%, at least 80%, at least 85%, at least 90%, at least 95%, at least 97%, or at least 99% amino acid sequence identity to the amino acid sequence of SEQ ID NO:1.

Figure 2A:
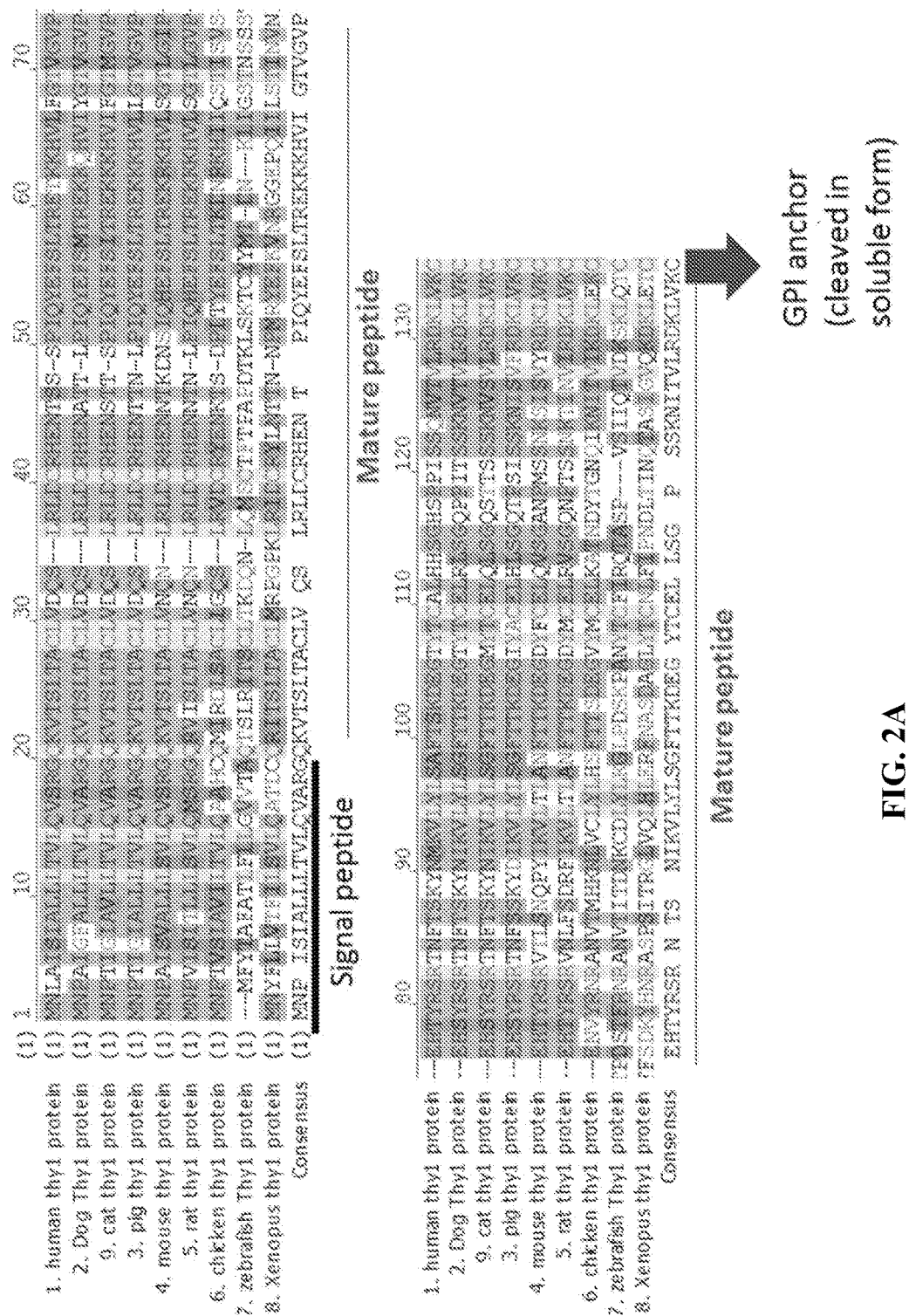

In one embodiment, the polypeptide fragment is derived from the mature peptide (i.e., the portion of the peptide without the signal sequence) (see FIG. 2A). In one embodiment, the Thy1 polypeptide fragment comprises or consists of the amino acid sequence corresponding to amino acids 20-130 of SEQ ID NO:1. In one embodiment, the polypeptide fragment of Thy1 protein of the present invention includes a polypeptide sequence that has at least 70%, at least 75%, at least 80%, at least 85%, at least 90%, at least 95%, at least 97%, or at least 99% amino acid sequence identity to the amino acid sequence corresponding to amino acids 20-130 of SEQ ID NO:1.

In one embodiment, the Thy1 polypeptide or fragment thereof is a soluble Thy1 polypeptide. Exemplary Thy1 polypeptides or fragments thereof are those in which the GPI anchor is absent (e.g., by synthesis without the GPI anchor or by removal (e.g., cleavage)). The Thy1 polypeptide or fragment thereof may also be modified to improve stability (e.g., by acetylation).

The Thy1 protein or polypeptide fragment thereof in accordance with the present invention may also comprise one or more additions, substitutions, or deletions compared to a Thy1 protein having the amino acid sequence of SEQ ID NO:1. In one embodiment, the Thy1 protein or Thy1 polypeptide fragment may include one or more additions, substitutions or deletions at amino acid positions corresponding to N-glycosylation sites or other amino acid positions corresponding to post-translational modification. In one embodiment, the Thy1 protein or polypeptide fragment thereof comprises one or more additions, substitutions, or deletions at amino acid residues corresponding to amino acid residues 42, 79, and/or 119 of SEQ ID NO: 1.

In addition, portions of the N- or C-terminal regions may be deleted or the immunoglobulin domain (Thy1 has a single variable region like domain and hence is part of the immunoglobulin gene superfamily) may be disrupted (see FIG. 1A). FIG. 1A is a schematic of Thy1 protein architecture, showing major domain regions and glycosylation sites where Thy1 protein will be mutated/truncated to produce Thy1 polypeptides or fragments thereof in accordance with the present invention. Furthermore, phospholipase-C (PLC) can cleave the GPI-anchor creating a soluble Thy1.

In one embodiment, the Thy1 polypeptide fragment comprises or consists of the amino acid sequence of any of SEQ ID NOs: 11-15 (see FIG. 2B) (*=N glycosylation site; Ac=Acetylated), as follows:

```
                                            (SEQ ID NO: 11)
Ac-QKVTSLTACLVDQSLRLD;

(SEQ ID NO: 12)
CRHEN*TSSSPIQYEFSLTRE;

(SEQ ID NO: 13)
TKKHVLFGTVGVPEHTYRSRTN*FTS;

(SEQ ID NO: 14)
KYNMKVLYLSAFTSKDEGTYT;

(SEQ ID NO: 15)
CALHHSGHSPPISSQN*VTVLRDKLVKC.
```

In one embodiment the peptides are not glycosylated at the N glycosylation sites (*).

In one embodiment, the Thy1 protein having one or more additions, substitutions or deletions, or the Thy1 polypeptide fragment retains the biological function of native Thy1. Such biological function includes, without limitation, the ability to inhibit PPAR-gamma activity, promote ERK signaling, and inhibition of Fyn activity in multipotent stromal cells. Persons of ordinary skill in the art will readily appreciate from the description herein how one would test for retention of such function. Accordingly, instead of or in addition to those methods of treatment described herein that are carried out by use of a Thy1 protein or polypeptide fragment thereof, or an agent that enhances Thy1 expression (or a composition or formulation including such a protein or polypeptide fragment thereof or such an agent), the present invention also encompasses use of a compound that directly or indirectly inhibits Fyn. In addition to the Thy1 protein or polypeptide fragment thereof described herein, other known Fyn inhibitors may also be used (e.g., 1-Naphthyl PP1 (ChemCruz™ Biochemicals) and those described in Koo et al., "Fyn Inhibition by Cycloalkane-Fused 1,2-Dithiole-3-thiones Enhances Antioxidant Capacity and Protects Mitochondria from Oxidative Injury," *Mol Pharmacol* 82:27-36 (2012), which is hereby incorporated by reference in its entirety.)

In one embodiment according to the present invention, the Thy1 protein or polypeptide fragment thereof includes one or more additions, substitutions, or deletions that optimize or enhance the biological function of decreasing adipogenesis and/or reducing adipocyte size as compared to the function of native Thy1 protein. In one embodiment, this is carried out by iterative rounds of mutagenesis and screening or selection for the desired function of decreasing adipogenesis and/or reducing adipocyte size.

Proteins or polypeptides according to the present invention may be isolated proteins or polypeptides. Accordingly, another aspect of the present invention relates to an isolated nucleic acid molecule encoding a Thy1 protein or the fragment thereof according to the present invention.

The isolated proteins or polypeptides of the present invention may be prepared for use in accordance with the methods of the present invention using standard methods of synthesis known in the art, including solid phase peptide synthesis (Fmoc or Boc strategies) or solution phase peptide synthesis. Alternatively, peptides of the present invention may be prepared using recombinant expression systems described in more detail below.

Accordingly, it will be understood that Thy1 protein or the fragment thereof according to the present invention may be derived from a nucleotide sequence that encodes a Thy1 protein. For example, in one embodiment, the nucleotide sequence is the nucleotide sequence that encodes human Thy1. In one embodiment, the nucleotide sequence is derived from the following nucleotide sequence (GenBank Accession No. M11749.1, which is hereby incorporated by reference in its entirety) (coding portion in bold text):

```
                                                              (SEQ ID NO: 16)
  1  ggatccagga ctgagatccc agaaccatga acctggccat cagcatcgct ctcctgctaa 61  caggtacccg gcatgggca ggactggggc tccaggcgcc ctggcttcct tccctccaga 121  gaagcagctt ctccctcaca gtctcagaaa agcgcaggtg acaaagagag ggctcttttt 181  catcctgaag tcagccgatc caccgcgctg atattctgac ggcctgaggt ggttttttgga 241  aacacagttt gctgagccct ccttcacact attgaactag aatccccaac tgagaaccca 301  ggaaccagca tcaactccct aagatctcct gtccttgaaa cacattgata ggatccaagg 361  ctcaagcaga gtggggaggg aggctggggt ctgcaaagga gaagtgggat ccctggggtg 421  gggaaaggca ctcagagagc agacccccggt cccctcccta gccaggccca tctctccact 481  tcaggtgggt gggaggcccc tgtgccgcag gcccctccag tttgaaggag gcactgctgg 541  tgccagtctt gcaggtctcc cgagggcaga aggtgaccag cctaacggcc tgcctagtgg 601  accagagcct tcgtctggac tgccgccatg agaataccag cagttcaccc atccagtacg 661  agttcagcct gacccgtgag acaaagaagc acgtgctctt tggcactgtg ggggtgcctg 721  agcacacata ccgctcccga accaacttca ccagcaaata ccacatgaag gtcctctact 781  tatccgcctt cactagcaag gacgagggca cctacacgtg tgcactccac cactctggcc
```

-continued

```
 841 attccccacc catctcctcc cagaacgtca cagtgctcag aggtgagaca agccctaac
 901 aaggtcaagt gagctgggag agccaggctc ggggacagca ggcagttccc ttggctggac
 961 tagagaggag aatagcccca taacgctctc accctctccc aactgctgcc tggtcaactg
1021 gggaaccatt gccttcggtg tgaatggggt gaagagctca gggccagaca ggcagagcag
1081 tgtggttcca ccagaactgt gggcaaggcc tttggcccct aatcttcctt ctcccagcgg
1141 gaaacaggga tgacaccacc tccctcagcc agttttcttg tcatgatgtt tagtaaggtt
1201 ttcataagat gatatgtgtg caagagatca gtaatctgca aatgggaaag atggctggtt
1261 ctgtgagacc aggctgttcc tggtcccagc taagacattg cagtacccac ctcccaaagg
1321 gagtacaccc ttgctttggg cctgtgcctg cctgagtcct gatccgtctt ccttcctacc
1381 ctgcccccgg cccccttctc tttctgcaga caaactggtc aagtgtgagg gcatcagcct
1441 gctggctcag aacacctcgt ggctgctgct gctcctgctg tccctctccc tcctccaggc
1501 cacggatttc atgtccctgt gactggtggg gcccatggag gagacaggaa gcctcaagtt
1561 ccagtgcaga gatcctactt ctctgagtca gctgaccccc tcccccaat ccctcaaacc
1621 ttgaggagaa gtggggaccc caccctcat caggagttcc agtgctgcat gcgattatct
1681 acccacgtcc acgcggccac ctcaccctct ccgcacacct ctggctgtct ttttgtactt
1741 tttgttccag agctgcttct gtctggttta tttaggtttt atccttcctt ttctttgaga
1801 gttcgtgaag agggaagcca ggattgggga cctgatggag agtgagagca tgtgaggggt
1861 agtgggatgg tggggtacca gccactggag gggtcatcct tgcccatcgg gaccagaaac
1921 ctgggagaga cttggatgag gagtggttgg gctgtgctgg gcctagcacg gacatggtct
1981 gtcctgacag cactcctcgg caggcatggc tggtgcctga agacccccaga tgtgagggca
2041 ccaccaagaa tttgtggcct accttgtgag ggagagaact gaggatctcc agcattctca
2101 gccacaacca aaaaaaaata aaagggcag ccctccttac cactgtggaa gtccctcaga
2161 ggccttgggg catgacccag tgaagatgca ggtttgacca ggaaagcagc gctagtggag
2221 ggttggagaa ggaggtaaag gatgagggtt catcatccct ccctgcctaa ggaagctaaa
2281 agcatggccc tgctgcccct ccctgcctcc acccacagtg gagagggcta caaaggagga
2341 caagaccctc tcaggctgtc ccaagctccc aagagcttcc agagctctga cccacagcct
2401 ccaagtcagg tggggtggag tcccagagct gcacagggtt tggcccaagt ttctaaggga
2461 ggcacttcct cccctcgccc atcagtgcca gcccctgctg gctggtgcct gagcccctca
2521 gacagccccc tgccccgcag gcctgccttc tcaggactt ctgcggggcc tgaggcaagc
2581 catggagtga gacccaggag ccggacactt ctcaggaaat ggcttttccc aaccccagc
2641 ccccaccgg tggttcttcc tgttctgtga ctgtgtatag tgccaccaca gcttatgcca
2701 tctcattgag gacaaagaaa actgcacaat aaaaccaagc ctctggaatc tgtcctcgtg
2761 tccacctggc cttcgctcct ccagcagtgc ctgcctgccc ccgctt
```

In one embodiment, the nucleotide sequence is derived from the following nucleotide sequence (GenBank Accession No. BC065559, which is hereby incorporated by reference in its entirety):

(SEQ ID NO: 17)
```
atgaacctgg ccatcagcat cgctctcctg ctaacagtct
tgcaggtctc ccgagggcag aaggtgacca gcctaacggc
ctgcctagtg gaccagagcc ttcgtctgga ctgccgccat
gagaatacca gcagttcacc catccagtac gagttcagcc
tgacccgtga gacaaagaag cacgtgctct ttggcactgt
gggggtgcct gagcacacat accgctcccg aaccaacttc
accagcaaat acaacatgaa ggtcctctac ttatccgcct
tcactagcaa ggacgagggc acctacacgt gtgcactcca
```

-continued

```
ccactctggc cattccccac ccatctcctc ccagaacgtc acagtgctca gagacaaact ggtcaagtgt gagggcatca gcctgctggc tcagaacacc tcgtggctgc tgctgctcct gctctccctc tccctcctcc aggccacgga tttcatgtcc ctgtga
```

In another embodiment of the present invention, the Thy1 protein or the fragment thereof is derived from a nucleotide sequence that encodes an ortholog of human Thy1. Suitable orthologs include, but are not limited to, dog, cat, pig, mouse, rat, chicken zebrafish, or *Xenopus* Thy1 (see FIG. 2A). Nucleotide sequences encoding these orthologs are also available from GenBank.

The present invention also relates to agents that enhance Thy1 expression. Such an agent comprises any suitable agent that enhances Thy1 expression in a cell capable of expressing Thy1. In one embodiment, the agent is a small molecule. In another embodiment, the agent comprises an expression vector for expressing Thy1 protein, a polypeptide fragment thereof, or a polypeptide that is capable of enhancing expression of Thy1 by a cell.

Accordingly, one embodiment of the present invention relates to an agent that enhances Thy1 expression comprises a vector, where the vector comprises a nucleic acid construct comprising a nucleic acid molecule encoding a Thy1 protein or polypeptide fragment thereof; a 5' DNA promoter sequence; and a 3' terminator sequence, wherein the nucleic acid molecule, the promoter, and the terminator are operatively coupled to permit transcription of the nucleic acid molecule.

MicroRNAs ("miRNA" or "miR") are endogenous, small RNAs that regulate genes by suppressing target mRNA translation or increasing target mRNA degradation. New studies link expression of certain miRNAs with a number of diseases.

In one embodiment of the present invention, the agent that enhances Thy1 expression comprises a polypeptide or other small molecule suitable to inhibit a target miRNA that interrupts expression of Thy1. In one embodiment, the target miRNA is miRNA-103, miRNA-107, miR-125a, miR-125b, miR-150, and/or miRNA-130a. In one embodiment, the target miRNA is miRNA-103 and/or miRNA-107. In one embodiment, the inhibitor is an antagomir, also known as an anti-miR, or blockmir. Antagomirs are designed to inhibit the activity of a particular microRNA using an antisense oligonucleotide directed to the microRNA, whereas blockmirs are steric antisense blockers that bind to specific microRNA binding sites in target RNAs to prevent microRNA binding to the same site. The miRNA binding site may be present in the 3' UTR region of the Thy1 mRNA of, for example, SEQ ID NO: 16 above. In one embodiment, the miRNA binding site is (or corresponds to) positions 1523-2806 of SEQ ID NO: 16. The inhibitor of these miRNA can take the form of the inhibitor described in U.S. Patent Application Publ. Nos. 20120245219 to Khvorova et al., 20110245481 to Iba et al., and 20100286378 to Li et al., and PCT International Patent Application Nos. WO 2011/117353, WO 2012/069059, and WO 2008/151639 to Moller, each of which is hereby incorporated by reference in its entirety. In one embodiment, the inhibitor is a polypeptide or other small molecule that blocks transcription or maturation of the above miRNAs.

Accordingly, in one embodiment, the agent that enhances Thy1 expression comprises an expression vector, where the vector comprises a nucleic acid construct comprising a nucleic acid molecule encoding an miRNA inhibitor; a 5' DNA promoter sequence; and a 3' terminator sequence, wherein the nucleic acid molecule, the promoter, and the terminator are operatively coupled to permit transcription of the nucleic acid molecule.

Also encompassed are vectors or expression vectors comprising nucleic acid molecules as described above and host cells comprising such nucleic acid molecules. Nucleic acid molecules according to the present invention can be expressed in a host cell, and the encoded polynucleotides isolated, according to techniques that are known in the art.

Generally, the use of recombinant expression systems involves inserting the nucleic acid molecule encoding the amino acid sequence of the desired peptide into an expression system to which the molecule is heterologous (i.e., not normally present). One or more desired nucleic acid molecules encoding a peptide of the invention may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The preparation of the nucleic acid constructs can be carried out using standard cloning procedures well known in the art as described by JOSEPH SAMBROOK ET AL., MOLECULAR CLONING: A LABORATORY MANUAL (Cold Springs Harbor 1989). U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in a suitable host cell.

A variety of genetic signals and processing events that control many levels of gene expression (e.g., DNA transcription and messenger RNA ("mRNA") translation) can be incorporated into the nucleic acid construct to maximize peptide production. For the purposes of expressing a cloned nucleic acid sequence encoding a desired peptide, it is advantageous to use strong promoters to obtain a high level of transcription. Depending upon the host system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene. Common promoters suitable for directing expression in mammalian cells include, without limitation, SV40, MMTV, metallothionein-1, adenovirus Ela, CMV, immediate early, immunoglobulin heavy chain promoter and enhancer, and RSV-LTR. Tissue selective promoters can also be utilized, for example, the adiponectin promoter (Wang et al., "Identification and Characterization of a Promoter Cassette Conferring Adipocyte-specific Gene Expression," *Endocrinol.* 151(6):2933-9 (2010), which is hereby incorporated by reference in its entirety) or aP2 promoter (Kurlawalla-Martinez et al., "Insulin Hypersensitivity and Resistance to Streptozotocin-induced Diabetes in Mice Lacking PTEN in Adipose Tissue," *Mol Cell Biol.* 25(6):2498-2510 (2005), which is hereby incorporated by reference in its entirety).

There are other specific initiation signals required for efficient gene transcription and translation in prokaryotic cells that can be included in the nucleic acid construct to maximize peptide production. Depending on the vector system and host utilized, any number of suitable transcription and/or translation elements, including constitutive, inducible, and repressible promoters, as well as minimal 5' promoter elements, enhancers or leader sequences may be used. For a review on maximizing gene expression see Roberts and Lauer, "Maximizing Gene Expression On a Plasmid Using Recombination In Vitro," *Methods in Enzymology* 68:473-82 (1979), which is hereby incorporated by reference in its entirety.

A nucleic acid molecule encoding an isolated protein or polypeptide of the present invention, a promoter molecule of choice, including, without limitation, enhancers, and leader sequences; a suitable 3' regulatory region to allow transcription in the host, and any additional desired components, such as reporter or marker genes, are cloned into the vector of choice using standard cloning procedures in the art, such as described in JOSEPH SAMBROOK ET AL., MOLECULAR CLONING: A LABORATORY MANUAL (Cold Springs Harbor 1989); FREDERICK M. AUSUBEL, SHORT PROTOCOLS IN MOLECULAR BIOLOGY (Wiley 1999); and U.S. Pat. No. 4,237,224 to Cohen and Boyer, which are hereby incorporated by reference in their entirety.

Once the nucleic acid molecule encoding the protein or polypeptide has been cloned into an expression vector, it is ready to be incorporated into a host. Recombinant molecules can be introduced into cells, without limitation, via transfection (if the host is a eukaryote), transduction, conjugation, mobilization, or electroporation, lipofection, protoplast fusion, mobilization, or particle bombardment, using standard cloning procedures known in the art, as described by JOSEPH SAMBROOK ET AL., MOLECULAR CLONING: A LABORATORY MANUAL (Cold Springs Harbor 1989), which is hereby incorporated by reference in its entirety.

A variety of suitable host-vector systems may be utilized to express the recombinant protein or polypeptide. Primarily, the vector system must be compatible with the host used. Host-vector systems include, without limitation, the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria.

Purified peptides may be obtained by several methods readily known in the art, including ion exchange chromatography, hydrophobic interaction chromatography, affinity chromatography, gel filtration, and reverse phase chromatography. The peptide is preferably produced in purified form (preferably at least about 80% or 85% pure, more preferably at least about 90% or 95% pure) by conventional techniques. Depending on whether the recombinant host cell is made to secrete the peptide into growth medium, the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

As noted above, the present invention relates to, inter alia, the treatment of a condition involving excessive adipogenesis. "Treat," "treating" or "treatment" is used herein to mean to reduce (wholly or partially) the symptoms, duration or severity of a disease or condition, including curing the disease, or to prevent the disease or condition.

Conditions suitable for treatment in accordance with the present invention include diseases relating to excess adipogenesis. The condition may include thyroid eye disease, obesity, type 2 diabetes, insulin resistance, metabolic syndrome, cardiovascular disease, lipohypertrophy, lipidema, steatosis, benign or malignant lipoma, benign or malignant liposarcoma, and excess throat fat that leads to sleep apnea. The condition also includes being overweight.

As used herein, "obese" or "obesity" means a medical condition in which excess body fat has accumulated to the extent that it may have an adverse effect on health, leading to reduced life expectancy and/or increased health problems. Obesity increases the likelihood of various diseases, particularly heart disease, type 2 diabetes, breathing difficulties during sleep, certain types of cancer and osteoarthritis. According to the Centers for Disease Control and Prevention (CDC), a body mass index (BMI) of 30 or higher defines adult humans as obese, and a BMI of from 25.0 to 29.9 defines adult humans as overweight. BMI is calculated by dividing the subject's mass by the square of his or her height (e.g., (pounds×703)/inches$^2$). Methods of determining whether or not an individual is overweight or obese are known in the art. "Obesity" in cats and dogs is defined as a body weight that is greater than 20% above optimal body weight.

In one embodiment, the administering of the active agents in accordance with the present invention is effective to decrease body weight, reduce adipose tissue accumulation, decrease blood glucose levels, reduce adipocyte hypertrophy, reduce total fat deposits (as measured by volume or weight), reduce total number of adipocytes, reduce inflammatory mediators, such as IL-6 and/or IL-8, increase leptin, and/or reduce hemoglobin H1C in a tissue of the selected subject.

The subjects to be treated in accordance with the present invention can have varying degrees of severity of the condition. Consequently, it is expected that the degree of symptom control can constitute preventing further development of symptoms or a reduction in the severity of symptoms.

The terms "drug" and "active agent" are used interchangeably and are intended to have their broadest interpretation as any therapeutically active substance which is delivered to a living organism to produce a desired, usually beneficial, effect. For example, the active agent according to the present invention is a Thy1 protein or polypeptide fragment thereof, or an agent that enhances Thy1 expression, as described above. Administration of the active agents can be repeated as needed, e.g., up to several times daily during treatment of a condition and according to a periodic schedule (once weekly or up to several times a week, including once daily) to inhibit recurrence of the condition. Treatment regimen for the administration of the agents can also be determined readily by those with ordinary skill in the art. That is, the frequency of administration and size of the dose can be established by routine optimization, preferably while minimizing any side effects.

The above-identified agents are preferably administered in the form of pharmaceutical formulation that includes one or more of the active agents, alone or in combination with one or more additional active agents, together with a pharmaceutically acceptable carrier.

Exemplary modes of administration include, without limitation, orally, by inhalation, by intranasal or airway instillation, optically, intranasally, topically, transdermally, parenterally, subcutaneously, intravenous injection, intraarterial injection, injection to the retro-ocular space, intradermal injection, intramuscular injection, intrapleural instillation, intraperitoneally injection, intraventricularly, intralesionally, by application to mucous membranes, or implantation of a sustained release vehicle.

For instance, the administering may carried out by injecting the composition into the retro-ocular space or application of the composition comprising the agent onto a surface of the subject's eye. In another embodiment, the administering may carried out by topical application of the composition to regions of the body with excessive fat accumulation. In yet another embodiment, the administering may be carried out by subcutaneous delivery of the composition to regions of the body with excessive fat accumulation. In addition to these forms for localized or regional delivery of the active agents, systemic delivery of the compositions can also be achieved, e.g., orally, intravenously, intraarterially, or by inhalation.

The active agent is generally present in a pharmaceutical formulation or composition of the invention in a therapeutically effective amount, i.e., an amount effective to bring about a desired therapeutic result in the treatment of a condition. The amount that constitutes a therapeutically effective amount varies according to the particular active agent, the condition being treated, any drugs being coadministered with the selected active agent, desired duration of treatment, and other components of the pharmaceutical formulation. Accordingly it is not practical to enumerate particular preferred amounts but such can be readily determined by those skilled in the art with due consideration of these factors.

The compositions or formulations according to the present invention may include a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the pharmaceutical formulation or composition will contain from about 0.01 to 99 percent, 5 to 90 percent, and preferably from about 20 to 75 percent of active agents, together with the adjuvants, carriers and/or excipients.

One exemplary formulation is a solid composition containing one or more active agents according to the present invention and a mucoadhesive substance in the conjunctival sac, wherein the adhesion strength of the mucoadhesive substance is in the range of from 200 to 1000 g. The use of such mucoadhesive substance for posterior optical drug delivery is described in U.S. Patent Application Publ. No. 20090036552, which is hereby incorporated by reference in its entirety.

Another exemplary formulation is an injectable sustained-release formulation that includes one or more active agents according to the present invention and a nanosphere. The nanosphere contains a particle that comprises a particle-forming component capable of forming a vesicle, and an agent-carrying component capable of forming a complex with the therapeutic agent(s) via electrostatic charge-charge interaction or hydrophobic-hydrophobic interaction. The particle-forming component has at least one head group moiety selected from a hydrophobic head group moiety, a polar head group moiety and a combination thereof. The agent-carrying component is a chemical entity that contains one or more negatively or positively charged groups. The use of such a nanosphere composition is described in U.S. Patent Application Publ. No. 20080118500, which is hereby incorporated by reference in its entirety.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and *acacia*), and the like, each containing a predetermined amount of one or more active agents of the present invention as an active ingredient. One or more active agents of the present invention may also be administered as bolus, electuary or paste.

Tablets, capsules, and the like can also contain a binder such as gum tragacanth, *acacia*, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

Liquid dosage forms for oral administration of the active agents of the invention include pharmaceutically-acceptable emulsions, microemulsions, solutions, suspensions, syrups and elixirs.

Pharmaceutical formulations (compositions) for intraocular injection of one or more active agents of the invention into the eyeball include solutions, emulsions, suspensions, particles, capsules, microspheres, liposomes, matrices, etc. See, e.g., U.S. Pat. No. 6,060,463, U.S. Patent Application Publication No. 2005/0101582, and PCT application WO 2004/043480, which are hereby incorporated by reference in their entirety. For instance, a pharmaceutical formulation for intraocular injection may comprise one or more active agents of the invention in combination with one or more pharmaceutically-acceptable sterile isotonic aqueous or non-aqueous solutions, suspensions or emulsions, which may contain antioxidants, buffers, suspending agents, thickening agents or viscosity-enhancing agents (such as a hyaluronic acid polymer). Examples of suitable aqueous and nonaqueous carriers include water, saline (preferably 0.9%), dextrose in water (preferably 5%), buffers, dimethylsulfoxide, alcohols and polyols (such as glycerol, propylene glycol, polyethylene glycol, and the like). These compositions may also contain adjuvants such as wetting agents and emulsifying agents and dispersing agents. In addition, prolonged absorption of the injectable pharmaceutical form may be brought about by the inclusion of agents which delay absorption such as polymers and gelatin. Injectable depot forms can be made by incorporating the drug into microcapsules or microspheres made of biodegradable polymers such as polylactide-polyglycolide. Examples of other biodegradable polymers include poly(orthoesters), poly(glycolic) acid, poly (lactic) acid, polycaprolactone and poly(anhydrides). Depot injectable formulations are also prepared by entrapping the drug in liposomes (composed of the usual ingredients, such as dipalmitoyl phosphatidylcholine) or microemulsions which are compatible with eye tissue. Depending on the ratio of drug to polymer or lipid, the nature of the particular polymer or lipid components, the type of liposome employed, and whether the microcapsules or microspheres are coated or uncoated, the rate of drug release from microcapsules, microspheres and liposomes can be controlled.

The active agents of the invention can also be administered surgically as an ocular implant. For instance, a reservoir container having a diffusible wall of polyvinyl alcohol or polyvinyl acetate and containing one or more active agents of the invention can be implanted in or on the sclera. As another example, one or more active agents of the invention can be incorporated into a polymeric matrix made of a polymer, such as polycaprolactone, poly(glycolic) acid, poly(lactic) acid, poly(anhydride), or a lipid, such as sebacic acid, and may be implanted on the sclera or in the eye. This is usually accomplished with the animal receiving a topical or local anesthetic and using a small incision made behind the cornea. The matrix is then inserted through the incision and sutured to the sclera.

The one or more active agents of the invention can also be administered topically to the eye, and a preferred embodiment of the invention is a topical pharmaceutical composition suitable for application to the eye. Topical pharmaceutical compositions suitable for application to the eye include solutions, suspensions, dispersions, drops, gels, hydrogels and ointments. See, e.g., U.S. Pat. No. 5,407,926 and PCT applications WO 2004/058289, WO 01/30337 and WO 01/68053, the complete disclosures of all of which are incorporated herein by reference.

Topical formulations suitable for application to the eye comprise one or more one or more active agents of the invention in an aqueous or nonaqueous base. The topical formulations can also include absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents. Topical formulations suitable for application to the eye will preferably comprise an absorption or permeation enhancer to promote absorption or permeation of the one or more active agents of the invention into the eye and/or a thickening agent or viscosity enhancer that is capable of increasing the residence time of one or more active agents of the invention in the eye. See PCT applications WO 2004/058289, WO 01/30337 and WO 01/68053.

Exemplary absorption/permeation enhancers include methylsulfonylmethane, alone or in combination with dimethylsulfoxide, carboxylic acids and surfactants. Exemplary thickening agents and viscosity enhancers include dextrans, polyethylene glycols, polyvinylpyrrolidone, polysaccharide gels, Gelrite®, cellulosic polymers (such as hydroxypropyl methylcellulose), carboxyl-containing polymers (such as polymers or copolymers of acrylic acid), polyvinyl alcohol and hyaluronic acid or a salt thereof.

Liquid dosage forms (e.g., solutions, suspensions, dispersions and drops) suitable for treatment of the eye can be prepared, for example, by dissolving, dispersing, suspending, etc. one or more active agents of the invention in a vehicle, such as, for example, water, saline, aqueous dextrose, glycerol, ethanol and the like, to form a solution, dispersion or suspension. If desired, the pharmaceutical formulation may also contain minor amounts of non-toxic auxiliary substances, such as wetting or emulsifying agents, pH buffering agents and the like, for example sodium acetate, sorbitan monolaurate, triethanolamine sodium acetate, triethanolamine oleate, etc.

Aqueous solutions and suspensions suitable for treatment of the eye can include, in addition to one or more active agents of the invention, preservatives, surfactants, buffers, salts (preferably sodium chloride), tonicity agents and water. If suspensions are used, the particle sizes should be less than 10 µm to minimize eye irritation. If solutions or suspensions are used, the amount delivered to the eye should not exceed 50 µl to avoid excessive spillage from the eye.

Colloidal suspensions suitable for treatment of the eye are generally formed from microparticles (i.e., microspheres, nanospheres, microcapsules or nanocapsules, where microspheres and nanospheres are generally monolithic particles of a polymer matrix in which the formulation is trapped, adsorbed, or otherwise contained, while with microcapsules and nanocapsules the formulation is actually encapsulated). The upper limit for the size of these microparticles is about 5µ, to about 10µ.

Ophthalmic ointments suitable for treatment of the eye include one or more active agents of the invention in an appropriate base, such as mineral oil, liquid lanolin, white petrolatum, a combination of two or all three of the foregoing, or polyethylene-mineral oil gel. A preservative may optionally be included.

Ophthalmic gels suitable for treatment of the eye include one or more active agents of the invention suspended in a hydrophilic base, such as Carpobol-940 or a combination of ethanol, water and propylene glycol (e.g., in a ratio of 40:40:20). A gelling agent, such as hydroxyethylcellulose, hydroxypropylcellulose, hydroxypropylmethylcellulose, or ammoniated glycyrrhizinate, is used. A preservative and/or a tonicity agent may optionally be included.

Hydrogels suitable for treatment of the eye are formed by incorporation of a swellable, gel-forming polymer, such as those listed above as thickening agents or viscosity enhancers, except that a formulation referred to in the art as a "hydrogel" typically has a higher viscosity than a formulation referred to as a "thickened" solution or suspension. In contrast to such preformed hydrogels, a formulation may also be prepared so to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives and ABA block copolymers of ethylene oxide and propylene oxide (conventionally referred to as "poloxamers" and available under the Pluronic® tradename from BASF-Wayndotte).

Preferred dispersions are liposomal, in which case the formulation is enclosed within liposomes (microscopic vesicles composed of alternating aqueous compartments and lipid bilayers).

Eye drops can be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

The active agents of the invention can also be applied topically by means of drug-impregnated solid carrier that is inserted into the eye. Drug release is generally effected by dissolution or bioerosion of the polymer, osmosis, or combinations thereof. Several matrix-type delivery systems can be used. Such systems include hydrophilic soft contact lenses impregnated or soaked with the desired active agent of the invention, as well as biodegradable or soluble devices that need not be removed after placement in the eye. These soluble ocular inserts can be composed of any degradable substance that can be tolerated by the eye and that is compatible with the active agent of the invention that is to be administered. Such substances include, but are not limited to, poly(vinyl alcohol), polymers and copolymers of polyacrylamide, ethylacrylate and vinylpyrrolidone, as well as cross-linked polypeptides or polysaccharides, such as chitin.

Dosage forms for the other types of topical administration (i.e., not to the eye) or for transdermal administration of active agents of the invention include powders, sprays, emulsions, solutions, suspensions, foams, ointments, pastes, creams, lotions, gels, solutions, patches, drops and inhalants. The active agent may be mixed under sterile conditions with a pharmaceutically-acceptable carrier, and with any buffers, or propellants which may be required. The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Exemplary pharmaceutically acceptable carriers according to the present invention include, without limitation, tromethane ethanol, polyethylene glycol, glycerin, propylene glycol, acrylates, Carbopol, purified water, benzyl alcohol, cetyl alcohol, citric acid, monoglycerides, diglycerides, triglycerides, oleyl alcohol, sodium cetostearylsulphate, sodium hydroxide, stearyl alcohol, white petrolatum, mineral oil, propylene carbonate, white wax, paraffin, and any combination thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal formulations include, without limitation, a transdermal delivery system, typically in the form of a patch that contains a depot of the active agent (s) in a pharmaceutically acceptable transdermal carrier, or simply a solution phase carrier that is deposited onto the skin, where it is absorbed. A number of transdermal delivery systems are known in the art, such as U.S. Pat. No. 6,149,935 to Chiang et al., PCT Application Publ. No. WO2006091297 to Mitragotri et al., EP Patent Application EP1674068 to Reed et al., PCT Application Publ. No. WO2006044206 to Kanios et al., PCT Application Publ. No. WO2006015299 to Santini et al., each of which is hereby incorporated by reference in its entirety. Transdermal patches have the added advantage of providing controlled delivery of active agents of the invention to the body. Such dosage forms can be made by dissolving, dispersing or otherwise incorporating one or more active agents of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. A drug-impregnated solid carrier (e.g., a dressing) can also be used for topical administration.

Pharmaceutical formulations include those suitable for administration by inhalation or insufflation or for nasal administration. For administration to the upper (nasal) or lower respiratory tract by inhalation, the active agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more active agents of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, active agents of the invention may be administered by means of nose drops or a liquid spray, such as by means of a plastic bottle atomizer or metered-dose inhaler. Liquid sprays are conveniently delivered from pressurized packs. Typical of atomizers are the Mistometer (Wintrop) and Medihaler (Riker).

Nose drops may be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

The active agent(s) may also be administered parenterally. Solutions or suspensions of these active agents can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

Pharmaceutical compositions or formulations of the present invention suitable for parenteral administrations comprise one or more active agents of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection or implantation. The pharmaceutical formulation may be in the form of a polymeric matrix in which the active agents to be administered are captured. Release of the active agents can be controlled via selection of materials and the amount of drug loaded into the vehicle. Implantable drug delivery systems include, without limitation, microspheres, hydrogels, polymeric reservoirs, cholesterol matrices, polymeric systems, and non-polymeric systems. A number of suitable implantable delivery systems are known in the art, such as U.S. Pat. No. 6,464,687 to Ishikawa et al., U.S. Pat. No. 6,074,673 to Guillen, each of which is hereby incorporated by reference in its entirety.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

As noted above, liposomal or micelle preparations can also be used to deliver the active agents of the present invention. Liposomes are vesicles comprised of one or more concentrically ordered lipid bilayers which encapsulate an aqueous phase. They are normally not leaky, but can become leaky if a hole or pore occurs in the membrane, if the membrane is dissolved or degrades, or if the membrane temperature is increased to the phase transition temperature. Current methods of drug delivery via liposomes require that the liposome carrier ultimately become permeable and release the encapsulated drug at the target site. This can be accomplished, for example, in a passive manner wherein the liposome bilayer degrades over time through the action of various agents in the body. Every liposome composition will have a characteristic half-life in the circulation or at other sites in the body and, thus, by controlling the half-life of the liposome composition, the rate at which the bilayer degrades can be somewhat regulated.

In contrast to passive drug release, active drug release involves using an agent to induce a permeability change in the liposome vesicle. Liposome membranes can be constructed so that they become destabilized when the environment becomes acidic near the liposome membrane (see, e.g., *Proc. Natl. Acad. Sci. USA* 84:7851 (1987); *Biochemistry* 28:908 (1989), each of which is hereby incorporated by reference in its entirety). When liposomes are endocytosed by a target cell, for example, they can be routed to acidic endosomes which will destabilize the liposome and result in drug release.

Alternatively, the liposome membrane can be chemically modified such that an enzyme is placed as a coating on the membrane, which enzyme slowly destabilizes the liposome. Since control of drug release depends on the concentration of enzyme initially placed in the membrane, there is no real effective way to modulate or alter drug release to achieve "on demand" drug delivery. The same problem exists for pH-sensitive liposomes in that as soon as the liposome vesicle comes into contact with a target cell, it will be engulfed and a drop in pH will lead to drug release.

Different types of liposomes can be prepared according to Bangham et al., *J. Mol. Biol.* 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

Like liposomes, micelles have also been used in the art for drug delivery. A number of different micelle formulations have been described in the literature for use in delivery proteins or polypeptides, and others have been described which are suitable for delivery of nucleic acids. Any suitable micelle formulations can be adapted for delivery of the therapeutic protein or polypeptide or nucleic acids of the present invention. Exemplary micelles include without limitation those described, e.g., in U.S. Pat. No. 6,210,717 to Choi et al.; and U.S. Pat. No. 6,835,718 to Kosak, each of which is hereby incorporated by reference in its entirety.

When it is desirable to achieve heterologous expression of a protein that promotes or increases expression of Thy1 protein or a polypeptide fragment thereof, then DNA molecules encoding these products can be delivered into the cell. Basically, this includes providing a nucleic acid molecule encoding the desired product, and then introducing the nucleic acid molecule into the cell under conditions effective to express the desired product in the cell. Preferably, this is achieved by inserting the nucleic acid molecule into an expression vector before it is introduced into the cell.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, *Biotechniques* 6:616-627 (1988) and Rosenfeld et al., *Science* 252:431-434 (1991), WO 93/07283, WO 93/06223, and WO 93/07282, each of which is hereby incorporated by reference in its entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., *Science* 258:1485-1488 (1992); Walsh et al., *Proc. Nat'l Acad. Sci. USA* 89:7257-7261 (1992); Walsh et al., *J. Clin. Invest.* 94:1440-1448 (1994); Flotte et al., *J. Biol. Chem.* 268:3781-3790 (1993); Ponnazhagan et al., *J. Exp. Med.* 179:733-738 (1994); Miller et al., *Proc. Nat'l Acad. Sci. USA* 91:10183-10187 (1994); Einerhand et al., *Gene Ther.* 2:336-343 (1995); Luo et al., *Exp. Hematol.* 23:1261-1267 (1995); and Zhou et al., *Gene Ther.* 3:223-229 (1996), each of which is hereby incorporated by reference in its entirety. In vivo use of these vehicles is described in Flotte et al., *Proc. Nat'l Acad. Sci. USA* 90:10613-10617 (1993); and Kaplitt et al., *Nature Genet.* 8:148-153 (1994), each of which is hereby incorporated by reference in its entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler et al., which is hereby incorporated by reference in its entirety. Lentivirus vectors can also be utilized, including those described in U.S. Pat. No. 6,790,657 to Arya, and U.S. Patent Application Nos. 20040170962 to Kafri et al. and 20040147026 to Arya, each of which is hereby incorporated by reference in its entirety.

Regardless of the type of infective transformation system employed, it should be targeted for delivery of the nucleic acid to a specific cell type. For example, for delivery of the nucleic acid into a cluster of cells (e.g., adipose cells), a high titer of the infective transformation system can be introduced directly within the site of those cells so as to enhance the likelihood of cell infection. The infected cells will then express the desired product, e.g., a protein that enhances expression of Thy1 protein or a polypeptide fragment thereof. Alternatively, these infective transformation systems can be administered in combination with a liposomal or micelle preparation, as well as a depot injection.

Administration may also involve transferring the nucleic acid sequence that encodes the desired product to a suitable ex vivo host cell, plurality of cells, or tissue that is/are compatible for implantation into the body of a subject as part of an ex vivo therapy protocol and then implanting such host cells, plurality of cells, or tissue into the body of the subject. Suitable cells are described in more detail below. The cell(s) or tissue will then express the desired product, e.g., a protein that enhances expression of Thy1 protein or a polypeptide fragment thereof.

Administration may also involve local hydrodynamic delivery of the nucleic acid sequence that encodes the desired product into the subject. Although, non-hydrodynamic systemic delivery methods may also be used. For example, some delivery agents are selected from the following non-limiting group of cationic polymers, modified cationic polymers, peptide molecular transporters, lipids, liposomes and/or non-cationic polymers. As noted above, viral vector delivery systems may also be used.

The formulations according to the present invention may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The above-identified formulations may also include one or more additional active ingredients suitable for the treatment of the condition. The formulations may also be administered in combination with one or more current therapies, which will be known to those of ordinary skill in the art based on the particular condition(s) to be treated.

Another aspect of the present invention relates to a pharmaceutical formulation. The formulation includes a Thy1 protein or polypeptide fragment thereof, or an agent that enhances Thy1 expression and a pharmaceutically acceptable carrier. Suitable Thy1 proteins or polypeptide fragments thereof, as well as agents that enhance Thy1 expression are described above. Suitable pharmaceutically acceptable carriers and formulations are also described above.

Yet another aspect of the present invention relates to a method of inhibiting adipogenesis and/or decreasing adipocyte size. This method includes providing a Thy1 protein or polypeptide fragment thereof, or an agent that enhances Thy1 expression; and contacting an adipocyte or adipocyte precursor with the Thy1 protein or polypeptide fragment thereof, or agent that enhances Thy1 expression thereby inhibiting adipogenesis and/or decreasing adipocyte size. The method according to this aspect of the present invention may be carried out in vitro or in vivo. Thy1 proteins or polypeptide fragments thereof, as well as agents that enhance Thy1 expression are described above.

A further aspect of the present invention is directed to a method of screening a candidate compound for its ability to influence adipogenesis. This method includes contacting a cell capable of expressing Thy1 with a candidate compound; measuring the presence of or the amount of Thy1 expressed by the contacted cell, where a change in the level of Thy1 relative to the level of Thy1 in the cell in the absence of said candidate compound indicates that the candidate compound influences adipogenesis.

Increase or decrease in the level of Thy1 is measured with reference to the level of Thy1 expressed in a cell in the absence of a candidate compound. A decrease in the level of Thy1 relative to the level of Thy1 in the cell in the absence of the candidate compound indicates that the candidate compound promotes adipogenesis. An increase in the level of Thy1 relative to the level of Thy1 in the cell in the absence of the candidate compound indicates that the candidate compound inhibits adipogenesis.

Suitable cells useful in accordance with the present invention include precursor adipocytes and mature adipocytes. In one embodiment, the cell(s) are stem cells. Suitable stem cells include pluripotent and multipotent stem cells. For example, multipotent stromal cells (e.g., mesenchymal stem cells) are useful in accordance with the present invention. In one embodiment, the precursor adipocyte is cultured from adipose tissue. In another embodiment, the precursor adipocyte is cultured from, e.g., umbilical cord blood and/or bone marrow.

In one embodiment, the cell is one that has been transformed with a nucleic acid construct comprising a nucleic acid molecule encoding Thy1 or a fragment thereof and a reporter gene; a 5' DNA promoter sequence; and a 3' terminator sequence, wherein the nucleic acid molecule, the promoter, and the terminator are operatively coupled to permit transcription of the nucleic acid molecule.

Suitable reporter genes may be any reporter gene known to those of ordinary skill in the art. In one embodiment, the reporter gene encodes a protein capable of producing or causing production of a detectable signal. For instance, the reporter gene may be one that encodes a bioluminescent (e.g., luciferase, green fluorescent protein, etc.) or fluorescent reporter.

The reporter gene or Thy1 expression may also be detected by use of a capture binding member such as an antibody or fragment thereof selective for the reporter gene or Thy1 (or fragment thereof), an aptamer selective for the reporter gene or Thy1 (or fragment thereof), or a ligand selective for the reporter gene or Thy1 (or fragment thereof). The capture binding member is capable of producing or causing production of a detectable signal, for instance, upon reaction with the reporter gene or Thy1 (or fragment thereof). The measurable signal includes any signal suitable for measurement by radiometric, colorimetric, or fluorometric means, size-separation, or precipitation. Production of the measurable signal may be achieved by addition of a secondary antibody that is coupled to a detectable signal or moiety, such as for example, an enzyme (e.g., luciferase), fluorophore, or chromophore. Formation of the complex is indicative of the presence of target protein or fragment thereof in the sample, which may then be quantified by measurement of the detectable signal or moiety. The secondary binding member may also be conjugated to a detectable moiety, such as fluorophores, biotin, avidin, streptavidin, HRP, or combinations thereof.

Measuring the detectable signal may be carried out according to any suitable measuring technique known in the art. For instance, measuring may be carried out using flow cytometry, imaging flow cytometry, western blotting, qPCR, robotic methods employing certain reporters and fluorescence, and/or fluorescence microscopy.

In one embodiment according to this aspect of the present invention, a plurality of candidate compounds are screened. The candidate compound may be a small molecule, microRNA (miRNA), a microRNA (miRNA) inhibitor, protein or polypeptide.

The screening methods according to the present invention may be run in high-throughput or high-content mode and may be used in automated screening of libraries of compounds.

EXAMPLES

Materials and *Methods for Examples* 1-10

Cell Culture

Primary Orbital fibroblasts were acquired and cultured as previously described (Lehmann et al., "Novel Anti-adipogenic Activity Produced by Human Fibroblasts," *Am J Physiol Cell Physiol* 299(3):C672-81 (2010), which is hereby incorporated by reference in its entirety). 3T3-L1 pre-adipocytes were obtained from the American Type Culture Collection (Rockville, Md.) and cultured in DMEM supplemented with 10% calf serum and antibiotics. All media and supplements were purchased from Gibco (Carlsbad, Calif.).

Isolation of Adipocytes from TED Orbit, Eyelid and Abdominal Fat Tissue

TED orbital tissue was obtained from TED patients undergoing orbital decompression. The protocol for tissue procurement was approved by the Research Subjects Review Board and informed, written consent was obtained from all patients. Eyelid and abdominal fat was obtained from the department of Surgical Pathology and was classified as waste tissue with potential identifiers removed before processing. All fat tissue was washed in ice cold PBS, cut into 2-3 mm pieces and vascular and stromal sections removed. The remaining adipocytes were flash frozen in liquid nitrogen and homogenized by mortar and pestle in a buffer containing 2% SDS and 60 mM Tris, pH 6.8. A fraction of sample was processed for SDS-PAGE and subsequent western blot analysis while another fraction was saved for RNA analysis.

Adipogenic Differentiation

3T3-L1 cells or primary fibroblasts were cultured to confluence before addition of the adipogenic medium. Cells were treated with an adipogenic medium containing 0.5 mM 3-isobutyl-1-methylxanthine, 0.25 µM dexamethasone, and 1 µg/ml insulin (all three from Sigma Aldrich, St. Louis, Mo.), 2 µM rosiglitazone (Cayman) for two days. After two days medium was replaced with dexamethasone, insulin and rosiglitazone for another 5-8 days. Media was replaced every 2 days through the duration of the experiment. After differentiation cells were analyzed for lipid accumulation and adipogenesis by Oil-red-O (Sigma Aldrich, St. Louis, Mo.) staining and AdipoRed (Cayman) staining as described previously. Lehmann et al., "Novel Anti-adipogenic Activity Produced by Human Fibroblasts," *Am J Physiol Cell Physiol* 299(3):C672-81 (2010), which is hereby incorporated by reference in its entirety.

Knockdown of Gene Expression by siRNA $5-8\times10^4$ or $1\times10^5$ cells were seeded into 24 well or 6 well cell culture plates (Corning) and subsequently were transiently transfected with 50-200 nM of siRNA (Ambion) using Lipofectamine 2000 (Invitrogen) as the transfection reagent and following the manufacture's protocol. The cells were incubated with siRNA specific for Thy1 specific or a corresponding non-specific control siRNA for 3-4 days before the cells were subjected to adipogenic differentiation experiments as described above. At the start of the adipogenic differentiation experiment, the cells were again transiently transfected with 100 nM Thy1-specific or control siRNA.

Transient transfection by Electroporation $2\times10^6$ cells were collected and resuspended in 100 ul of Ingenio electroporation solution (Mirus Bio, Madison, Wis.) containing appropriate DNA or siRNA complexes and electroporated with program U-023 on an Amaxa Nucleofector (Lonza, Cologne, GER) following the instructions from the manufacturer.

Luciferase Reporter Assays

Cells were collected and electroporated as described above with a PPARγ response element (PPRE) reporter luciferase construct containing three copies of a PPRE (PPRE×3-firefly luciferase) (Kim et al., "ADD1/SREBP1 Activates PPARgamma Through the Production of Endogenous Ligand," *Proc Natl Acad Sci USA* 95(8): 4333-7 (1998) and Forman et al., "15-Deoxy-delta 12, 14-prostaglandin J2 is a Ligand for the Adipocyte Determination Factor PPARgamma," *Cell* 83(5):803-12 (1995), each of which is hereby incorporated by reference in its entirety) and SV40-renilla luciferase (Promega, Madison, Wis.). Nucleofected cells were plated and allowed to grow for 6-8 h. Either DMSO (vehicle) or 100 nM rosiglitazone was then added to the cultures for an additional 14-18 h. Following incubation, cells were washed two times in 1×PBS and lysed directly in plates using the Dual-Glo luciferase assay buffer (Promega). Firefly and renilla luciferase readings were measured on a Varioskan Flash luminescent plate reader (Thermo Fisher) following manufacturer's instructions. Luciferase readings were normalized to the control vehicle treated samples for statistical analysis.

Lentiviral Transduction

Primary human fibroblasts were plated in 6 well plates (Falcon/Becton) in 10% FBS media and infected with pLOC-Thy1 (Open Biosystems), pLOC-control lentivirus at a multiplicity of infection of 10. Positively transduced cells were selected by culturing in the presence of 5 ng/ml blasticidin (Invitrogen) for two weeks. Expression of Thy1 was confirmed by western blot and flow cytometry.

Quantitative Real Time PCR (qPCR)

Total RNA was isolated using the RNeasy kit (Qiagen) following the manufacturer's protocol, treated with DNase (Qiagen) and assessed for purity using spectroscopy. For mRNA analysis 100-250 ng of total RNA was used with iSCRIPT Reverse transcriptase (Biorad) to generate cDNA. Following conversion to cDNA, an aliquot of each sample was used in Real Time PCR reactions using SYBR green reagent. The Real Time PCR reactions were carried out using a CFX Connect Real Time PCR instrument (Biorad). The primers used in this study are listed in Table 1, below.

TABLE 1

Primer Sets

| Gene | Primer Name | Sequence |
|---|---|---|
| TBP | TBP 794+ | CGA AAC GCC GAA TAT AAT CCC (SEQ ID NO: 18) |
| | TBP 966- | CCC AAC TTC TGT ACA ACT CTA GC (SEQ ID NO: 19) |
| FABP4 | hFABP4 + | ACA GGA AAG TCA AGA GCA CC (SEQ ID NO: 20) |
| | FABP4 - | AAC TTC AGT CCA GGT CAA CG (SEQ ID NO: 21) |
| Thy1 | THY1 fwd | ATC TCC TCC CAG AAC GTC (SEQ ID NO: 22) |
| | THY1 rev | ATC TCT GCA CTG GAA CTT G (SEQ ID NO: 23) |
| 18S rRNA | 18S rRNA+ | TGAGAAACGGCTACCACATC (SEQ ID NO: 24) |
| | 18S rRNA- | ACTACGAGCTTTTTAACTGC (SEQ ID NO: 25) |
| Beta actin | hActB 16 + | GCACAGAGCCTCGCCTT (SEQ ID NO: 26) |
| | hActB 127 - | CCTTGCACATGCCGGAG (SEQ ID NO: 27) |
| GAPDH | GAPDH+ | ATG GAA ATC CCA TCA CCA TCT T (SEQ ID NO: 28) |
| | GAPDH- | CGG CCC ACT TGA TTT TGG (SEQ ID NO: 29) |
| Thy1 3'UTR | THY1 3'UTR Fwd XhoI | TAC TCG AGT GAC TGG TGG GGC CCA TGG AGG (SEQ ID NO: 30) |
| | THY1 3'UTR Rev NotI | TAG CGG CCG CTG GGC AAA TGT GTC TCG TTA GGG (SEQ ID NO: 31) |

Western Blotting

Protein was isolated from 1-2×10$^6$ cells and lysed in 60 mM Tris, pH 6.8, 2% SDS containing 1× protease inhibitor cocktail (Sigma, St. Louis, Mo.). The lysates were passed through a 26 gauge needle 5-6 times to shear DNA. Protein concentrations were determined by the BioRad detergent compatible protein assay (Biorad). 1-10 μg of total protein/lane were subjected to SDS-PAGE. Protein gels were transferred to PVDF membrane (Millipore) and probed with antibodies as specified. Two different Thy1 antibodies were used in the study, one antibody from Cell Signaling Technologies (Cambridge, Mass.) recognizes both human and rodent forms of Thy1, while the second antibody from Sigma recognizes only the human form of Thy1.

Flow Cytometry

Cells were collected by trypsinization and washed two times in 1×PBS before blocking with 5% normal mouse serum in 0.1% azide, 1% BSA and 1×PBS. Blocked cells were then incubated with either anti-mouse Thy1.2-PE conjugated antibody (BD Biosciences) for detection of rodent Thy1 or anti-human Thy1-PE conjugated antibody (BD Biosciences) for detection of human Thy1. Isotype controls and positively stained cells were run on a FACS Canto II flow cytometer (BD Biosciences). Analysis was performed using FlowJo software (TreeStar).

Statistical Analysis

Student's T test was used for statistical analysis and p values of *, p<0.01; **, p<0.001; are considered significant.

Example 1—Thy1 Inhibits Adipogenesis

Stem cells are distinguished from other cells because they have an almost limitless ability to regenerate and have the potential to form multiple different types of cells required for normal tissue function. Mesenchymal stem cells (MSCs), also called multipotent stromal cells, present in adipose, bone marrow, dental pulp or umbilical cord tissues can form adipocytes, osteoblasts, myofibroblasts or other effector cells depending on the presence of various extracellular signals and molecular events. Adipocytes are the major storage cell for lipid-based energy. Adipogenesis requires activation of the ligand-activated transcription factor, peroxisome proliferator activated receptor gamma (PPARγ or PPARgamma). PPARγ is the master regulator of adipogenesis, inducing expression of key adipogenic genes such as glucose transporter type 4 (GLUT4) and fatty acid binding protein 4 (FABP4). Increased rates of adipogenesis or increased adipocyte size results in obesity. The following experiments show that Thy1 expression is key in determining if MSCs can form adipocytes.

To test that Thy1 is controlling adipogenesis, the NIH 3T3-L1 fibroblast cell line, which is widely used in the literature as a model of adipogenesis (Chen et al., "Krox20 Stimulates Adipogenesis Via C/Ebpbeta-Dependent and -Independent Mechanisms," Cell Metab, 1(2):93-106 (2005); Grontved et al., "Med14 Tethers Mediator to the N-Terminal Domain of Peroxisome Proliferator-Activated Receptor Gamma and Is Required for Full Transcriptional Activity and Adipogenesis," Mol Cell Biol 30(9):2155-69 (2010); Jung et al., "Peroxisome Proliferator-Activated Receptor Gamma/Signal Transducers and Activators of Transcription 5a Pathway Plays a Key Factor in Adipogenesis of Human Bone Marrow-Derived Stromal Cells and 3t3-L1 Preadipocytes," Stem Cells Dev 21(3):465-75 (2011); Pantoja et al., "Glucocorticoid Signaling Defines a Novel Commitment State During Adipogenesis in Vitro," Mol Biol Cell 19(10): 4032-41 (2008); Ross et al., "Dual Roles for the Notch Target Gene Hes-1 in the Differentiation of 3t3-L1 Preadipocytes," Mol Cell Biol 24(8):3505-13 (2004); Sarruf et al., "Cyclin D3 Promotes Adipogenesis through Activation of Peroxisome Proliferator-Activated Receptor Gamma," Mol Cell Biol 25(22):9985-95 (2005); Xue et al., "Distinct Stages in Adipogenesis Revealed by Retinoid Inhibition of Differentiation after Induction of PPARgamma," Mol Cell Biol 16(4):1567-75 (1996); and Ying et al., "Impaired Adipogenesis Caused by a Mutated Thyroid Hormone Alpha1 Receptor," Mol Cell Biol 27(6):2359-71 (2007), each of which is hereby incorporated by reference in its entirety), was utilized.

Figures 3A, 3B, 3C, 3D, 3E, 3F, 3G:
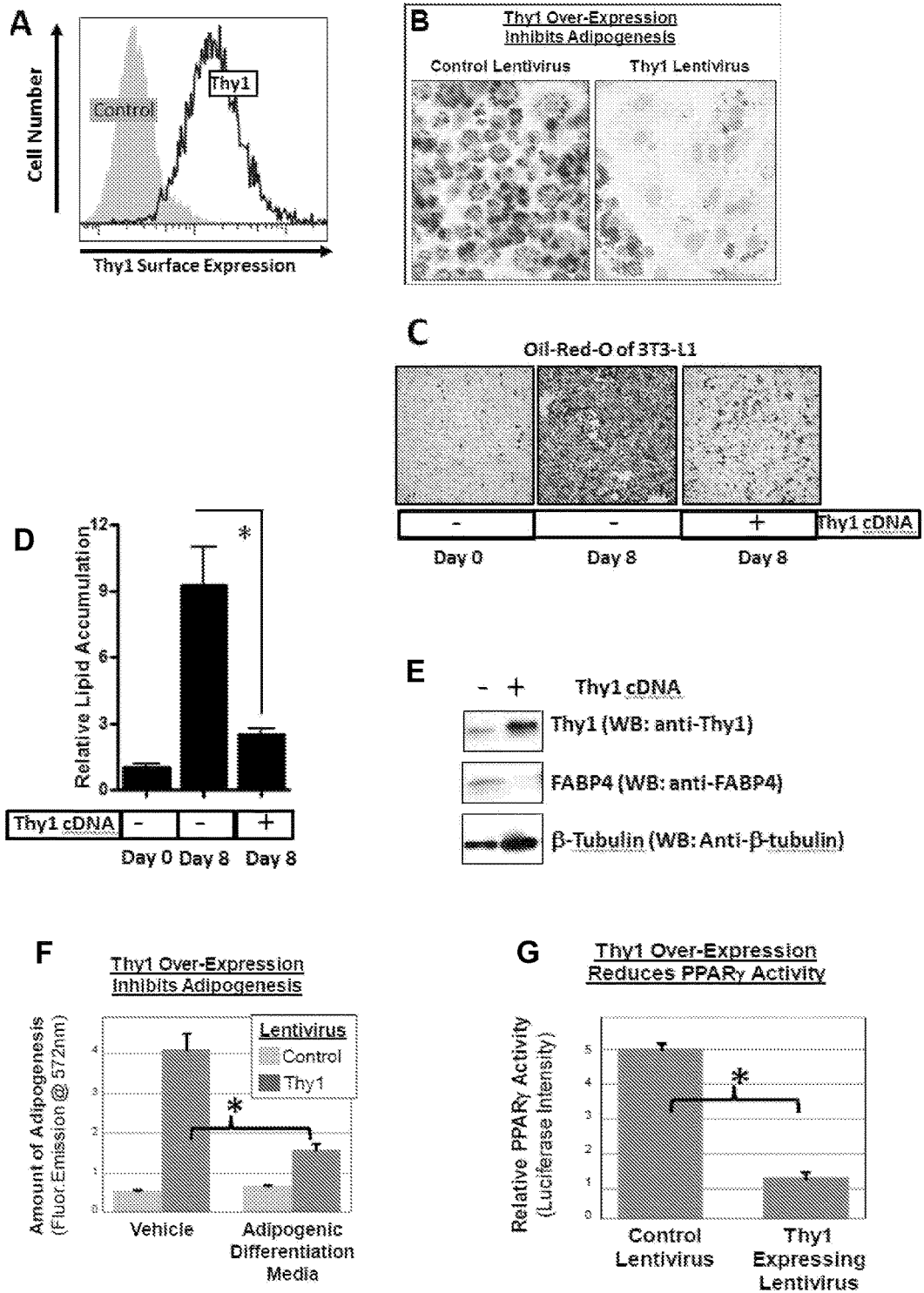
FIGS. 3A-3G show experimental results demonstrating that Thy1 inhibits adipogenesis.

As a robust test of the potency of human Thy1 to block adipogenesis, these 3T3-L1 cells were transfected with human Thy1 and most of the cells nicely expressed Thy1 (see FIGS. 3A-3G). Thy1 cDNA or a control plasmid was transfected into 3T3-L1 fibroblasts followed by flow cytometric analysis. In particular, flow cytometry analysis was conducted to analyze the expression of Thy1 in the lentivirus (LV)-treated and control cells. Flow cytometric analysis showed high expression of Thy1 in Thy1 LV-treated but not control cells (FIG. 3A). Adipogenesis was measured using Oil-red-O and AdipoRed staining Oil-red-O staining of 3T3-L1 cells that were induced to differentiate into adipocytes illustrated a remarkable inhibition of adipogenesis following introduction of Thy1 cDNA (FIG. 3B, right) as compared to a control construct (FIG. 3B, left). As shown in FIG. 3B, Oil-red-O staining showed abundant lipid droplet formation in control cells, but not in Thy1+ cells. FIG. 3C shows additional results of Oil-red-O staining of 3T3-L1 cells. Remarkable inhibition of adipogenesis was shown following introduction of Thy1 cDNA. FIG. 3D is a bar graph of results showing that lipid content was diminished by 80% in 3T3-L1 Thy1 cells compared to control (*=p<0.01, Student's T test). FIG. 3E shows results of western blot analysis of Thy1, FABP4, and β-tubulin on adipogenic day 5. As shown, FABP4 (an adipogenic marker) expression was also inhibited by Thy1 expression. Adipogenesis was also measured via fluorescence using AdipoRed staining, which showed that Thy1 over-expression significantly inhibits adipogenesis (FIG. 3F).

Further, ectopic expression of Thy1 inhibits PPARγ as shown by reporter assays and adipogenic assays (see FIG. 3G). PPARγ activity is measured via a PPRE. As shown in FIG. 3G, Thy1 inhibited PPARγ activity. Most interesting was that the majority of the cells completely failed to differentiate to adipocytes when cultured with a standard pro-adipogenic cocktail containing a synthetic PPARγ ligand.

These results provide evidence that Thy1 expression blunts adipogenesis.

Example 2—Thy1 Levels are Reduced by Obesogens

Figures 4A, 4B, 4C:
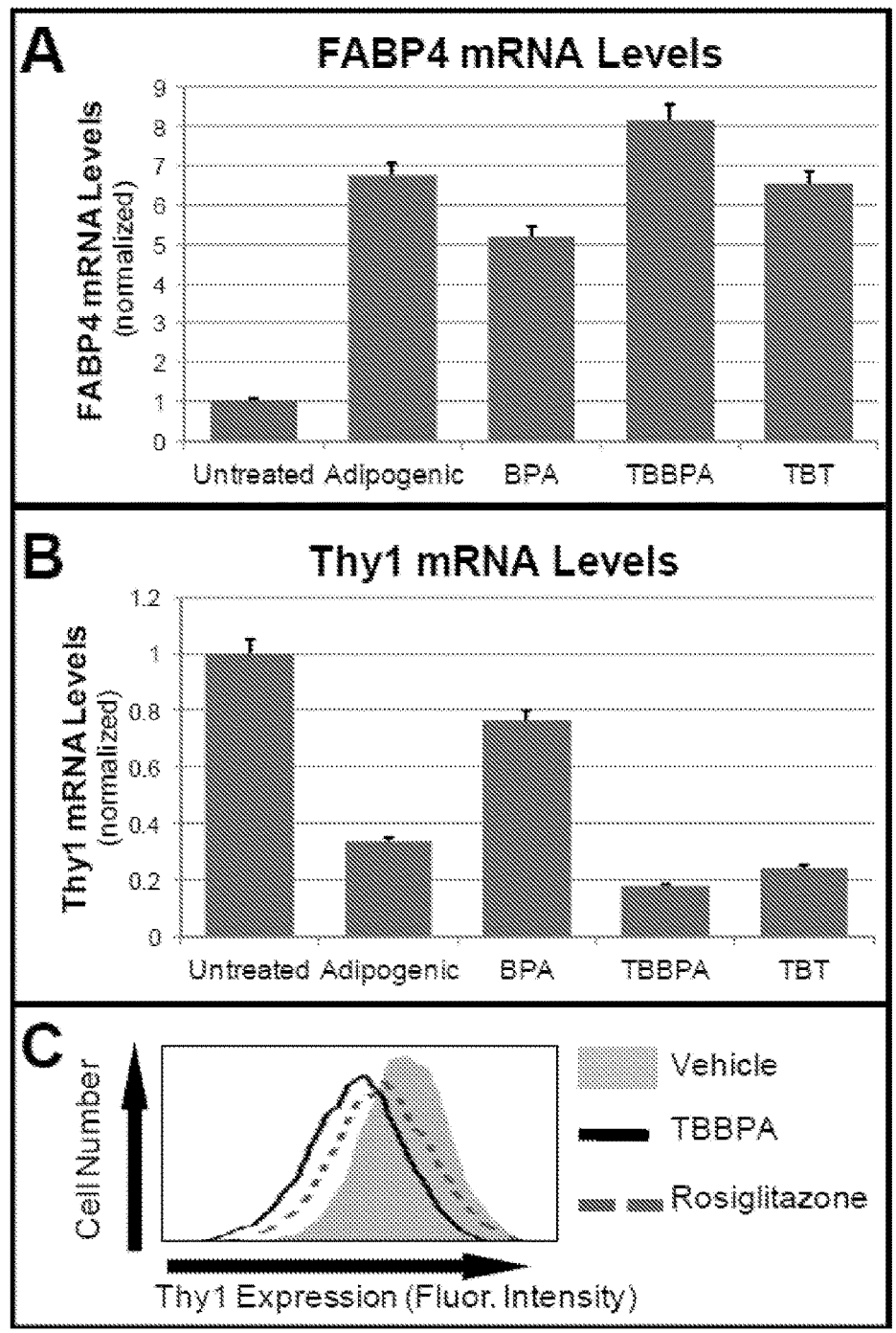
FIGS. 4A-4C show experimental results demonstrating that Thy1 levels are reduced by obesogens. hMSCs were induced to adipocytes with a control cocktail (adipogenic) or cocktail containing putative obesogens. To assess adipogenesis, FABP4 mRNA levels were quantified by qPCR and the results shown in FIG. 4A.

The following experiment involving human and mouse mesenchymal stem cells (hMSCs) demonstrates that Thy1 expression is dramatically reduced by TBBPA and TBT (see FIGS. 4A-4C).

In particular, hMSCs were induced to adipocytes with a rosiglitazone cocktail (adipogenic) or cocktail containing the putative obesogens BPA (1 μM), TBBPA (5 μM), or TBT (100 nM). Riu et al., "Peroxisome Proliferator-Activated Receptor Gamma is a Target for Halogenated Analogs of Bisphenol A," *Environ Health Perspect* 119(9):1227-32 (2011); Kirchner et al., "Prenatal Exposure to the Environmental Obesogen Tributyltin Predisposes Multipotent Stem Cells to Become Adipocytes," *Mol Endocrinol* 24(3):526-39 (2010); and Grun et al., "Endocrine-Disrupting Organotin Compounds are Potent Inducers of Adipogenesis in Vertebrates," *Mol Endocrinol* 20(9):2141-55 (2006), each of which is hereby incorporated by reference in its entirety. The obesogen doses selected are based on literature and represent concentrations proposed to be found in human tissues. Roos et al., "Circulating Levels of Persistent Organic Pollutants in Relation to Visceral and Subcutaneous Adipose Tissue by Abdominal MRI," *Obesity (Silver Spring)* (2012) and Antizar-Ladislao, B, "Environmental Levels, Toxicity and Human Exposure to Tributyltin (TBT)-Contaminated Marine Environment. A Review," *Environ Int* 34(2):292-308 (2008), each of which is hereby incorporated by reference in its entirety. As noted above, the cells were cultured in adipogenic medium containing rosiglitazone, a PPARγ ligand that promotes adipogenesis and obesity, and the noted putative obesogens.

qPCR analysis of the mRNA levels of Thy1 and the adipogenic marker FABP4 was conducted. As shown in FIG. 4A, all cocktails containing obesogens induced FABP4. The same samples as in FIG. 4A were used to measure Thy1 mRNA levels by qPCR. As shown in FIG. 4B, obesogens and control cocktail decreased Thy1 mRNA levels. Thy1 and FABP4 levels were normalized to TBP mRNA levels (control gene).

hMSCs were also treated with vehicle (DMSO), 20 uM TBBPA, or 10 uM rosiglitazone for 72 hrs, harvested and stained with a fluorescent anti-Thy1 antibody for analysis of Thy1 by flow cytometry. As shown in FIG. 4C, the surface expression of Thy1 is decreased by treatment with either TBBPA (solid black line) or rosiglitazone (dotted line) compared to vehicle treated cells (gray shade).

These results demonstrate that Thy1 expression was dramatically reduced by the tested obesogens.

Example 3—Thy1 is a Target of miR-103

Figures 5A, 5B, 5C, 6A, 6B, 6C:
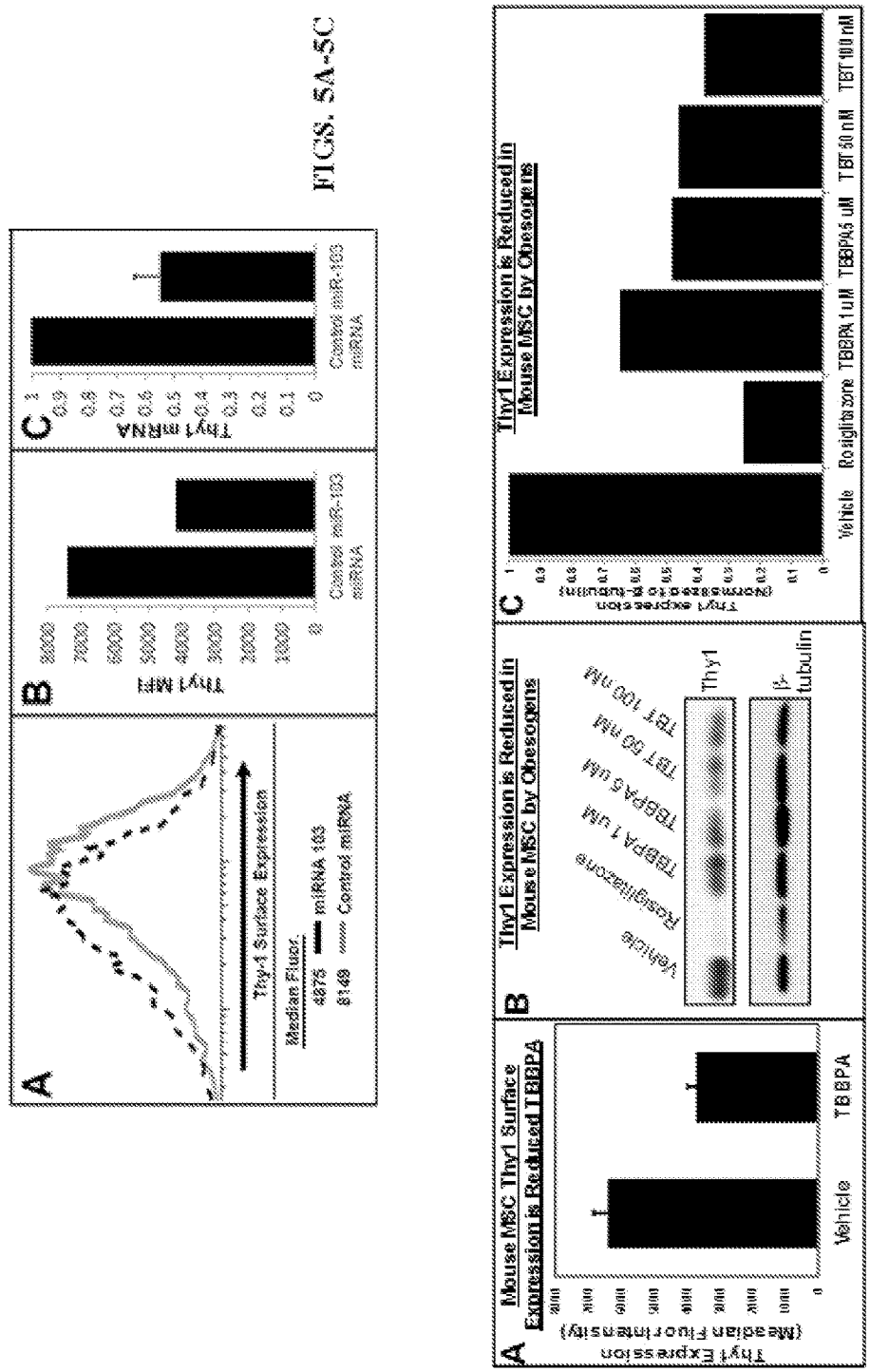
FIGS. 5A-5C are graphs showing experimental results demonstrating that Thy1 is a target of miR-103. A control miRNA or miR-103 was introduced into hMSCs and cells were cultured for 48 hrs, harvested, and stained with a fluorescent anti-Thy1 antibody for analysis of Thy1 by flow cytometry. The graph of results in FIG. 5A shows that the surface expression of Thy1 is decreased by miR-103 (black line) compared to control miRNA (gray line).
FIGS. 6A-6C show experimental results demonstrating that mouse MSCs reduce expression of Thy1 upon obesogen treatment. Mouse MSCs were cultured with obesogens for 96 hrs, harvested, and analyzed for Thy1 expression by flow cytometry or western blotting.

MicroRNAs (miRNAs) are endogenous, small RNAs that serve to regulate up to 90% of all human genes by suppressing target mRNA translation or increasing target mRNA degradation. Bartel, D. P., "MicroRNAS: Target Recognition and Regulatory Functions," *Cell* 136(2):215-33 (2009), which is hereby incorporated by reference in its entirety. New studies link expression of certain miRNAs with diseases such as rheumatoid arthritis, obesity, and cancer. Furer et al., "The Role of MicroRNA in Rheumatoid Arthritis and Other Autoimmune Diseases," *Clin Immunol* 136(1):1-15 (2010) and Xie et al., "MicroRNAS Induced During Adipogenesis That Accelerate Fat Cell Development Are Downregulated in Obesity," *Diabetes* 58(5):1050-7 (2009), each of which is hereby incorporated by reference in its entirety. One such miRNA is miR-103, which is upregulated in obesity. Trajkovski et al., "MicroRNAs 103 and 107 Regulate Insulin Sensitivity," *Nature* 474(7353):649-53 (2011), which is hereby incorporated by reference in its entirety. The data presented here shows that Thy1 is regulated by miR-103 (FIGS. 5A-5C). Thus, one mechanism whereby obesogens may dampen Thy1 expression is by inducing miR-103. Epidemiological studies have provided evidence that early and prenatal exposure to environmental factors including BPA and DDE influence the adult risk of developing diseases such as cancer and obesity. Boekelheide et al., "Predicting Later-Life Outcomes of Early-Life Exposures," *Environ Health Perspect* 120(10):1353-61 (2012), which is hereby incorporated by reference in its entirety. One general mechanism whereby early exposures could affect physiology later in life is through the alteration of epigenetic marks. Epigenetic marks such as CpG methylation have profound effects on transcriptional output of gene expression. Interestingly, the Thy1 genomic locus contains three CpG islands (identified through the cpgislands webpage at the University of Southern California website). Crow, J. M., "Obesity: Insensitive Issue," *Nature* 486:S12-13 (2012), which is hereby incorporated by reference in its entirety. Furthermore, a recent report demonstrates that the Thy1 locus is differentially methylated in ulcerative colitis. Hasler et al., "A Functional Methylome Map of Ulcerative Colitis," *Genome Res* 22(11):2137-7 (2012), which is hereby incorporated by reference in its entirety.

Generally, miRNAs serve to regulate gene expression by suppressing target mRNA translation and/or decreasing target mRNA stability. Guo et al., "Mammalian MicroRNAs Predominantly Act to Decrease Target mRNA Levels," *Nature* 466:835-840 (2010), which is hereby incorporated by reference in its entirety. Several algorithms such as TargetScan (Lewis et al., "Conserved Seed Pairing, Often Flanked by Adenosines, Indicates That Thousands of Human Genes are MicroRNA Targets," *Cell* 120:15-20 (2005), which is hereby incorporated by reference in its entirety), Pictar, and RNAhybrid can be used to predict which miRNAs may target the Thy1 mRNA 3'UTR. Several of candidate miRNAs identified with these algorithms include miR-103, miR-107, miR-125a, miR-125b, and miR-150, which are expressed by hMSCs (data not shown) and, based on the work described herein with miR-103, it is expected that these other miRNAs will behave similarly.

The following data reveal that ectopic expression of miR-103 decreases both Thy1 surface expression and Thy1 mRNA levels in MSCs (see FIGS. 5A-5C). In particular, FIGS. 5A-5C are graphs showing results that demonstrate Thy1 is a target of miR-103. A control miRNA or miR-103 was introduced into hMSCs and cells were cultured for 48 hrs, harvested, and stained with a fluorescent anti-Thy1 antibody for analysis of Thy1 by flow cytometry. The graph of results in FIG. 5A shows that the surface expression of Thy1 is decreased by miR-103 (black line) compared to control miRNA (gray line). FIG. 5B is a bar graph showing the mean fluorescent intensity (MFI) of Thy1 surface expression from FIG. 5A. The same samples as in FIG. 5A were used to measure Thy1 mRNA levels by qPCR. Thy1 mRNA levels were normalized to TATA-binding protein (TBP) mRNA levels (control gene). The results shown in FIG. 5C also demonstrate that Thy1 expression is reduced by miR-103.

Together these results evidence that miR-103 is induced during adipogenesis and it is expected from this evidence that obesogens will also induce miR103 and repress Thy1 expression.

Example 4—Thy1 is a Target of Obesogens

The following data show that mouse MSCs reduce expression of Thy1 upon obesogen treatment (see FIGS. 6A-6C). Mouse MSCs were cultured with obesogens for 96 hrs, harvested, and analyzed for Thy1 expression by flow cytometry or western blotting. The results of flow cytometric analysis are shown in FIG. 6A. In particular, Mean Fluorescent Intensity (MFI) shows a dramatic reduction in Thy1 surface expression in TBBPA (5 µM) exposed samples (*p<0.05, error bars represent S.D.). FIG. 6B shows the results of western blotting, demonstrating a reduction in Thy1 after treatment with the obesogens TBBPA and TBT (concentrations in figure). FIG. 6C shows quantitation of Thy1 levels from FIG. 6B (Thy1 levels were normalized to β-tubulin levels).

Example 5—Thy1 Determines the Fate of TED Orbital Fibroblasts

Figure 7A:
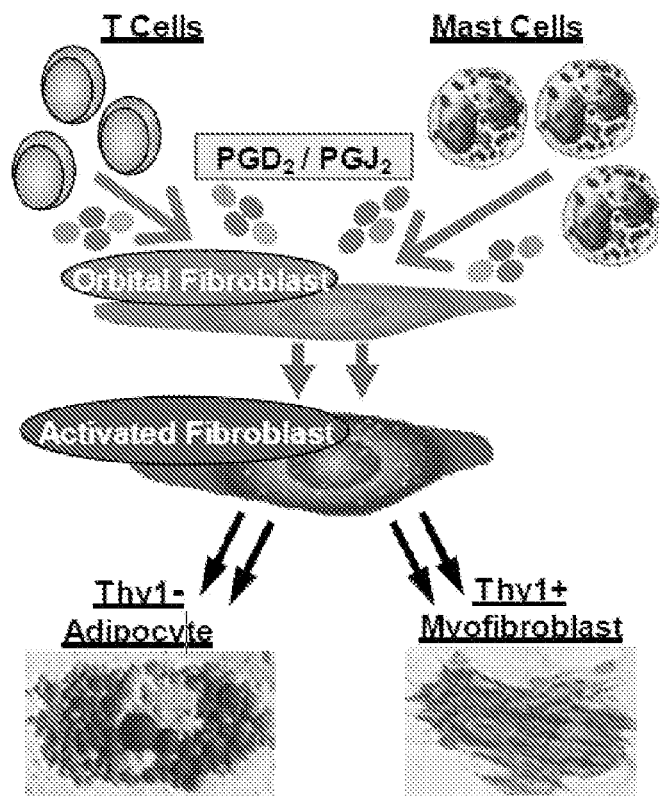
FIGS. 7A and 7B are schematic diagrams.

Development of TED is thought to occur when orbital tissue is infiltrated by immune cells that include activated T cells, B cells, and mast cells. Immune cells, whether through direct physical association and/or by release of cytokines (IL-1, TGF-β, etc.) and lipid mediators (PGD2, 15d-PGJ2, etc.), interact with sentinel fibroblasts present in orbital tissue leading to: (1) enhanced adipogenesis (fat accumulation) and (2) increased matrix deposition (collagen and hyaluronan) produced by adipocytes and myofibroblasts (see FIG. 7A). Guo et al., "Mast Cell-Derived Prostaglandin D2 Controls Hyaluronan Synthesis in Human Orbital Fibroblasts Via Dp1 Activation: Implications for Thyroid Eye Disease," *J Biol Chem* 285(21):15794-804 (2010) and Han & Smith, "T Helper Type 1 and Type 2 Cytokines Exert Divergent Influence on the Induction of Prostaglandin E2 and Hyaluronan Synthesis by Interleukin-1beta in Orbital Fibroblasts: Implications for the Pathogenesis of Thyroid-Associated Ophthalmopathy," *Endocrinology* 147(1):13-9 (2006), each of which is hereby incorporated by reference in its entirety. Fibroblasts, once thought to be merely structural cells, are now recognized to be key players in inflammation, disease progression and immune function. Baglole et al., "More Than Structural Cells, Fibroblasts Create and Orchestrate the Tumor Microenvironment," *Immunol Invest* 35(3-4):297-325 (2006); Redfern & McDermott, "Toll-Like Receptors in Ocular Surface Disease," *Experimental Eye Research* 90(6):679-87 (2010); Redfern et al., "Toll-Like Receptor Activation Modulates Antimicrobial Peptide Expression by Ocular Surface Cells," *Experimental Eye Research* 92(3):209-20 (2011); and Smith et al., "Unique Attributes of Orbital Fibroblasts and Global Alterations in Igf-1 Receptor Signaling Could Explain Thyroid-Associated Ophthalmopathy," *Thyroid* 18(9):983-8 (2008), each of which is hereby incorporated by reference in its entirety.

Figure 7B:
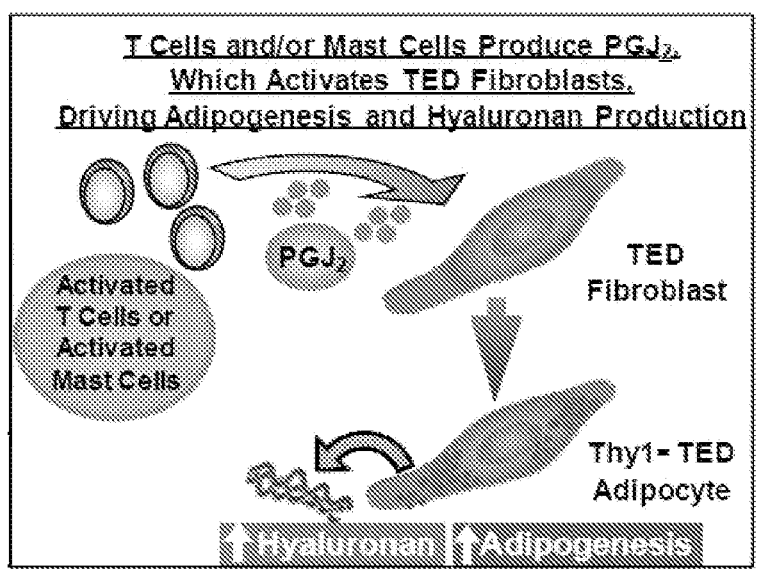

The inventors discovered that activated T cells from TED patients express the pro-inflammatory enzyme cyclooxygenase-2 (Cox-2) and produce prostaglandin (PG) lipid mediators (see FIG. 7B). Feldon et al., "Activated Human T Lymphocytes Express Cyclooxygenase-2 and Produce Proadipogenic Prostaglandins That Drive Human Orbital Fibroblast Differentiation to Adipocytes," *Am JPathol* 169(4): 1183-93 (2006), which is hereby incorporated by reference in its entirety. PGs have a wide range of effects (i.e. proliferation, differentiation) and can influence numerous cell types such as classical immune cells, endothelial cells and fibroblasts. Feldon et al., "Activated Human T Lymphocytes Express Cyclooxygenase-2 and Produce Proadipogenic Prostaglandins That Drive Human Orbital Fibroblast Differentiation to Adipocytes," *Am J Pathol* 169(4): 1183-93 (2006), which is hereby incorporated by reference in its entirety. This prior work shows that activated T cells drive orbital fibroblast adipogenesis, and that only a subset of orbital fibroblasts can convert into adipocytes. Feldon et al., "Activated Human T Lymphocytes Express Cyclooxygenase-2 and Produce Proadipogenic Prostaglandins That Drive Human Orbital Fibroblast Differentiation to Adipocytes," *Am J Pathol* 169(4):1183-93 (2006), which is hereby incorporated by reference in its entirety. The inventors have pioneered the classification of fibroblast subsets based on expression of Thy1 (also referred to as CD90). Phipps et al., "Characterization of Two Major Populations of Lung Fibroblasts: Distinguishing Morphology and Discordant Display of Thy1 and Class Ii Mhc," *Am J Respir Cell Mol Biol* 1(1):65-74 (1989), which is hereby incorporated by reference in its entirety.

Orbital fat from patients with TED is a unique type of adipose tissue. Kaminski et al., "Susceptibility of Ocular Tissues to Autoimmune Diseases," *Ann NY Acad Sci* 998: 362-74 (2003); Kumar & Bahn, "Relative Overexpression of Macrophage-Derived Cytokines in Orbital Adipose Tissue from Patients with Graves' Ophthalmopathy," *J Clin Endocrinol Metab* 88(9):4246-50 (2003); and Lehmann et al., "Immune Mechanisms in Thyroid Eye Disease," *Thyroid* 18(9):959-65 (2008), each of which is hereby incorporated by reference in its entirety. There are considerably higher levels of T cell and mast cell infiltration in TED orbital fat compared to other fat depots. Feldon et al., "Activated Human T Lymphocytes Express Cyclooxygenase-2 and Produce Proadipogenic Prostaglandins That Drive Human Orbital Fibroblast Differentiation to Adipocytes," *Am J Pathol* 169(4):1183-93 (2006) and Bujalska et al., "Characterisation of 11beta-Hydroxysteroid Dehydrogenase 1 in Human Orbital Adipose Tissue: A Comparison with Subcutaneous and Omental Fat," *J Endocrinol* 192(2):279-88 (2007), each of which is hereby incorporated by reference in its entirety. This is likely caused by aberrant production of inflammatory chemokines by TED adipocytes in the orbit. Kuriyan et al., "The Eye and Thyroid Disease," *Curr Opin Ophthalmol* 19(6):499-506 (2008); Ludgate & Baker, "Unlocking the Immunological Mechanisms of Orbital Inflammation in Thyroid Eye Disease," *Clin Exp Immunol* 127(2):193-8 (2002); and Prabhakar et al., "Current Perspective on the Pathogenesis of Graves' Disease and Ophthalmopathy," *Endocr Rev* 24(6):802-35 (2003), each of which is hereby incorporated by reference in its entirety. The inventors have observed that TED Thy1⁻ orbital adipocytes produce more inflammatory cytokines and chemokines than non-orbital adipocytes when provoked by inflammatory mediators.

In contrast to orbital fibroblasts, Thy1 is present on the majority if not all of fibroblasts from other anatomical areas such as the cornea. Pei et al., "Thy-1 Distinguishes Human Corneal Fibroblasts and Myofibroblasts from Keratocytes," *Exp Eye Res* 79(5):705-12 (2004); Koumas et al., "Fibroblast Subsets in the Human Orbit: Thy-1+ and Thy-1-Subpopulations Exhibit Distinct Phenotypes," *Eur J Immunol* 32(2):477-85 (2002); Koumas et al., "Fibroblast Heterogeneity: Existence of Functionally Distinct Thy1(+) and Thy1(−) Human Female Reproductive Tract Fibroblasts," *Am J Pathol* 159(3):925-35 (2001); and Smith et al., "Orbital Fibroblast Heterogeneity May Determine the Clinical Presentation of Thyroid-Associated Ophthalmopathy," *J Clin Endocrinol Metab* 87(1):385-92 (2002), each of which is hereby incorporated by reference in its entirety. The balance between Thy1⁻ and Thy1+ fibroblasts in the orbit is essential for homeostasis and response to inflammation. Lehmann et al., "Immune Mechanisms in Thyroid Eye Disease," *Thyroid* 18(9):959-65 (2008); Hwang et al., "Orbital Fibroblasts from Patients with Thyroid-Associated Ophthalmopathy Overexpress Cd40: Cd154 Hyperinduces 11-6, 11-8, and Mcp-1," *Invest Ophthalmol Vis Sci* 50(5): 2262-8 (2009); and Raychaudhuri et al., "Pge2 Induces 11-6 in Orbital Fibroblasts through Ep2 Receptors and Increased Gene Promoter Activity: Implications to Thyroid-Associated Ophthalmopathy," *PLoS One* 5(12):e15296 (2010), each of which is hereby incorporated by reference in its entirety. The inventors have shown that loss of this balance underlies the development and progression of TED. Koumas et al., "Thy-1 Expression in Human Fibroblast Subsets Defines Myofibroblastic or Lipofibroblastic Phenotypes," *Am J Pathol* 163(4):1291-300 (2003); Koumas et al., "Fibroblast Subsets in the Human Orbit: Thy-1+ and Thy-1-Subpopulations Exhibit Distinct Phenotypes," *Eur J Immunol* 32(2):477-85 (2002); Smith et al., "Orbital Fibroblast Heterogeneity May Determine the Clinical Presentation of Thyroid-Associated Ophthalmopathy," *J Clin Endocrinol Metab* 87(1):385-92 (2002); and Lehmann et al., "Novel Anti-Adipogenic Activity Produced by Human Fibroblasts," *Am J Physiol Cell Physiol* 299(3):C672-C681 (2010), each of which is hereby incorporated by reference in its entirety. The lack of Thy1 expression predisposes orbital fibroblasts to form TED adipocytes when provoked with PPARγ ligands. Koumas et al., "Thy-1 Expression in Human Fibroblast Subsets Defines Myofibroblastic or Lipofibroblastic Phenotypes," *Am J Pathol* 163(4):1291-300 (2003) and Lehmann et al., "Novel Anti-Adipogenic Activity Produced by Human Fibroblasts," *Am J Physiol Cell Physiol* 299(3): C672-C681 (2010), each of which is hereby incorporated by reference in its entirety. In contrast, Thy1+ orbital fibroblasts do not form adipocytes, but instead can develop into fibrogenic myofibroblasts when provoked by TGF-β.

Figures 8A, 8B:
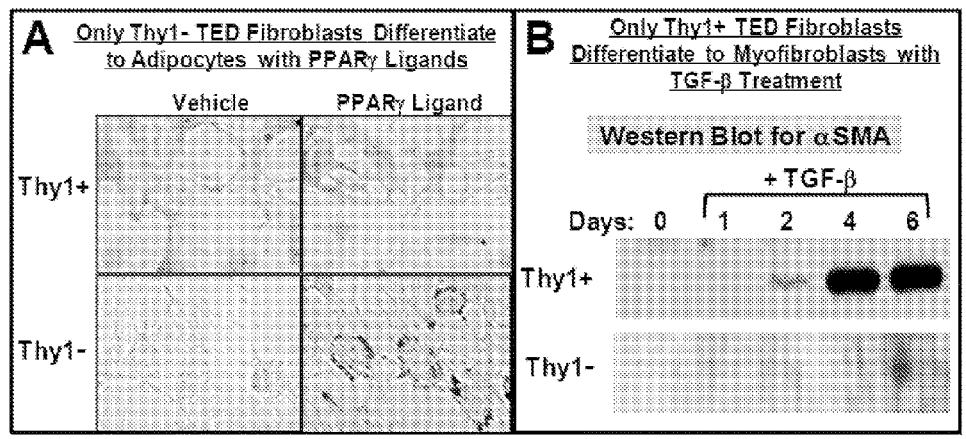
FIGS. 8A and 8B show experimental results demonstrating that Thy1 determines the fate of TED orbital fibroblasts. When Thy1 subsets of TED fibroblasts are treated with a PPARγ ligand, only the Thy1⁻ subset of cells differentiate to adipocytes, indicated by Oil-red-O staining of lipid droplets shown in FIG. 8A. Conversely, only Thy1+TED fibroblasts differentiate to myofibroblasts following TGF-β treatment as shown by western blotting for αSMA in FIG. 8B.
Figures 9A, 9B, 9C:
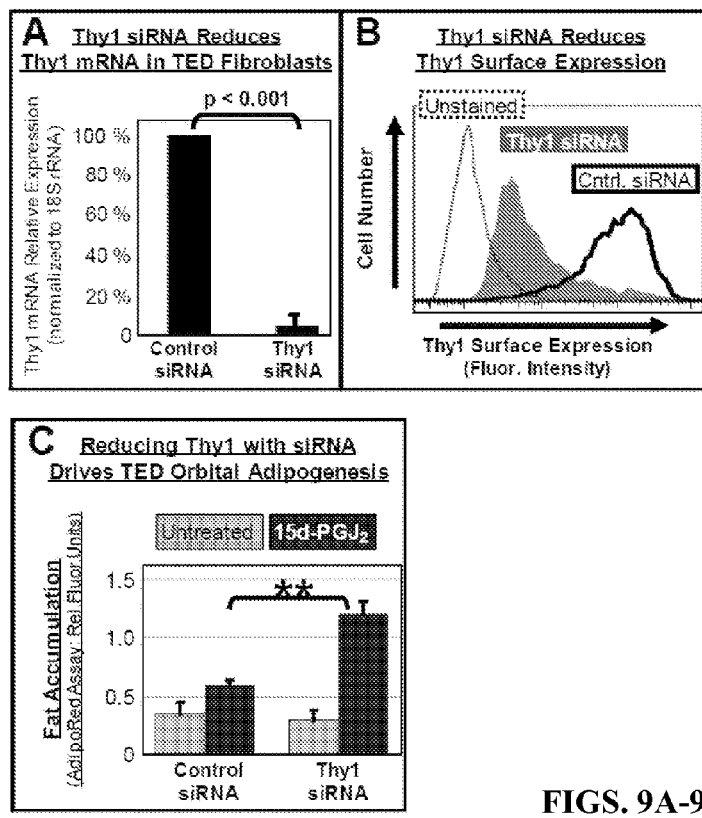
FIGS. 9A-9C show experimental results demonstrating that reduction of Thy1 expression enhances adipogenesis of TED orbital fibroblasts.

FIGS. 8A and 8B show an example of this association of Thy1 expression and cell fate. In an initial test of this, it was discovered that knock-down of Thy1 expression in FACS-purified Thy1+ fibroblasts using Thy1 siRNA enhances lipid accumulation (see FIGS. 9A-9C). FIG. 9 shows that Thy1 mRNA can be dramatically reduced with Thy1 siRNA, that Thy1 surface expression can be greatly reduced, and that Thy1 depleted orbital fibroblasts accumulate more lipid when exposed to a PPARγ ligand. The inventors have shown that Thy1+ fibroblasts secrete a soluble factor that impairs PPARγ-dependent TED adipogenesis. Lehmann et al., "Novel Anti-Adipogenic Activity Produced by Human Fibroblasts," *Am J Physiol Cell Physiol* 299(3):C672-C681 (2010), which is hereby incorporated by reference in its entirety. These observations support that Thy1 (which can be cleaved by phospholipases and shed (Bradley et al., "Roles and Regulation of Thy-1, a Context-Dependent Modulator of Cell Phenotype," *Biofactors* 35(3):258-65 (2009); Kemshead et al., "Human Thy-1: Expression on the Cell Surface of Neuronal and Glial Cells," *Brain Res* 236(2):451-61 (1982); Lehmann et al., "Novel Anti-Adipogenic Activity Produced by Human Fibroblasts," *Am J Physiol Cell Physiol* 299(3):C672-C681 (2010); Cohen et al., "Thy1 up-Regulates Fasl Expression in Lung Myofibroblasts Via Src Family Kinases," *Am J Respir Cell Mol Biol* 40(2):231-8 (2009); Phipps et al., "Differential Expression of Interleukin 1 Alpha by Thy-1+ and Thy-1-Lung Fibroblast Subpopulations: Enhancement of Interleukin 1 Alpha Production by Tumor Necrosis Factor-Alpha," *Eur J Immunol* 20(8):1723-7 (1990); Shan et al., "Thy-1 Attenuates Tnf-Alpha-Activated Gene Expression in Mouse Embryonic Fibroblasts Via Src Family Kinase," *PLoS One* 5 (7):e11662 (2010); and Chen et al., "Krox20 Stimulates Adipogenesis Via C/Ebpbeta-Dependent and -Independent Mechanisms," *Cell Metab,* 1(2):93-106 (2005), each of which is hereby incorporated by reference in its entirety)) is more than a surface marker and, in fact, prevents adipogenesis.

Figures 10A, 10B, 10C:
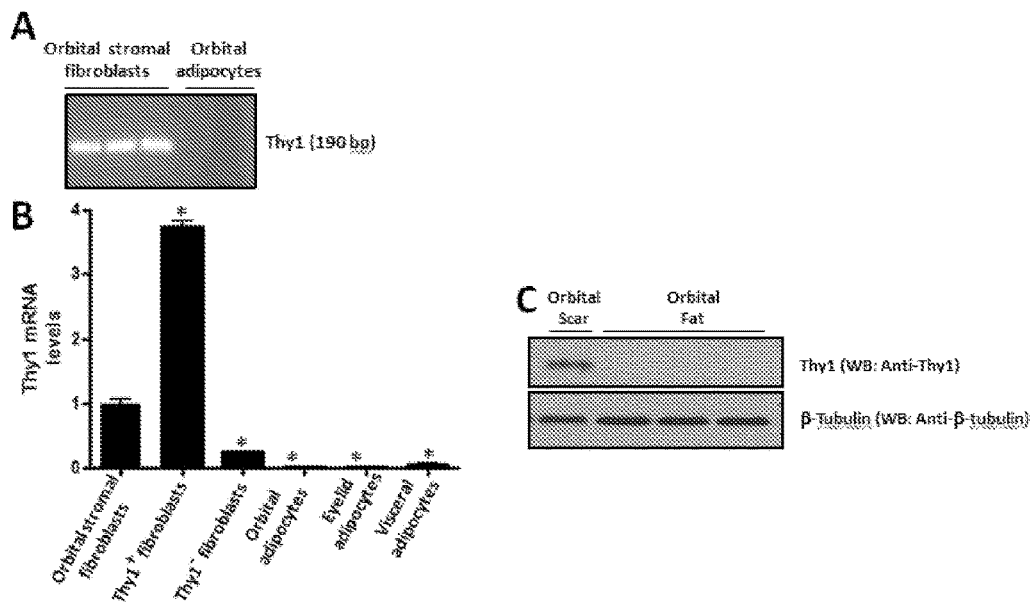
FIGS. 10A-10C show experimental results demonstrating that Thy1 is not expressed in human adipocytes from TED orbit, normal eyelid, or normal visceral fat tissue. Thy1 mRNA was analyzed by standard RT-PCR and visualized by ethidium bromide staining.

Example 6—Thy1 is not Expressed in Human Adipocytes from Orbit, Eyelid, or Visceral Fat Tissue Thy1 mRNA was analyzed by standard RT-PCR and visualized by ethidium bromide staining. As shown in FIG. 10A, orbital stromal fibroblasts express Thy1, while orbital adipocytes do not. FIG. 10B shows results of Thy1 mRNA analysis by real-time PCR, demonstrating that adipocyte Thy1 mRNA levels from orbit, eyelid, and visceral fat were less than 5% of stromal fibroblast samples. FIG. 10C shows results of analysis of orbital adipocyte and orbital scar tissue samples by western blot. As shown in FIG. 10C, Thy1 protein is not detectable in human orbit fat. (*=p<0.01) These data demonstrate that Thy1 is not expressed in human adipocytes from orbit, eyelid or visceral fat tissue.

Example 7—Thy1 Expression is Lost During Adipogenesis of 3T3-L1 Pre-Adipocytes

Figures 11A, 11B, 11C:
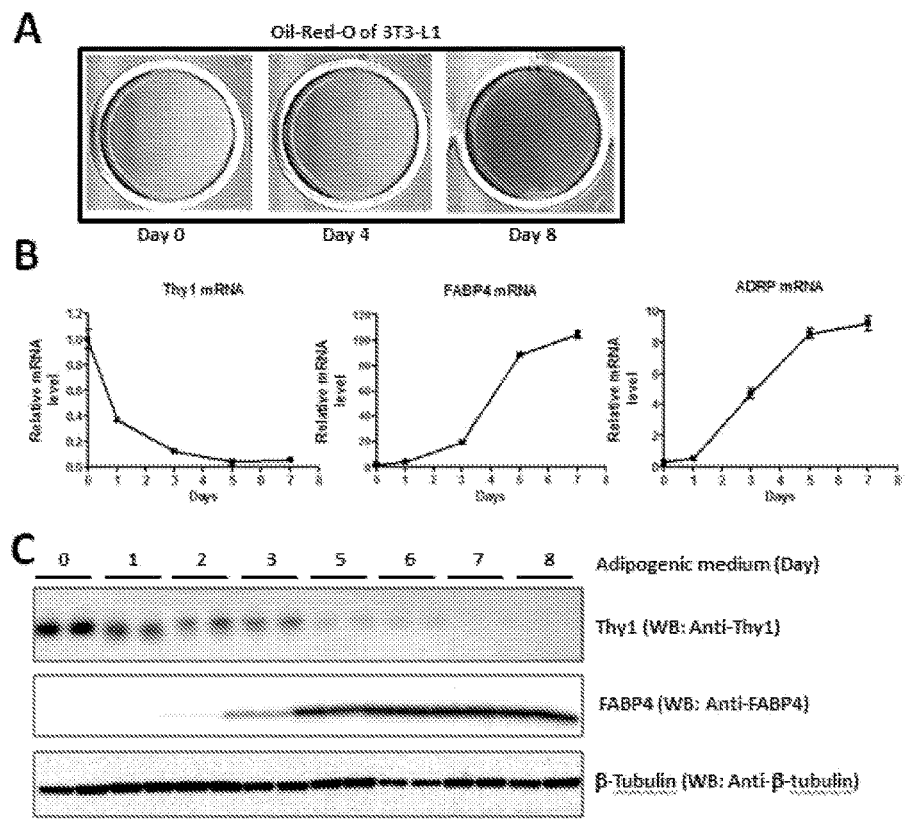
FIGS. 11A-11C show results demonstrating that Thy1 expression is lost during adipogenesis of 3T3-L1 pre-adipocytes. 3T3-L1 pre-adipocytes were induced to differentiate into adipocytes.

3T3-L1 pre-adipocytes were induced to differentiate into adipocytes. FIG. 11A shows results of Oil-red-O staining. These results show lipid accumulation of 3T3-L1 throughout experiment. FIG. 11B shows results of Thy1, fatty acid binding protein 4 (FABP4), and adipose-differentiation related protein (ADRP) mRNA analysis by real-time PCR. As shown, Thy1 mRNA levels decreased rapidly upon administration of adipogenic medium and were below 10% of control levels by Day 5. FIG. 11C shows results of western blot analysis of Thy1, FABP4, and b-tubulin (loading control). As shown, Thy1 levels were undetectable by Day 8. These data demonstrated that Thy1 expression is lost during adipogenesis of 3T3-L1 preadipocytes.

Example 8—Reduced Thy1 Expression Increases Adipogenesis in Human Pre-Adipocyte Fibroblasts Thy1 specific or control siRNA was introduced into human pre-adipocyte fibroblasts using Lipofectamine 2000.

Figures 12A, 12B, 12C, 12D, 12E, 12F:
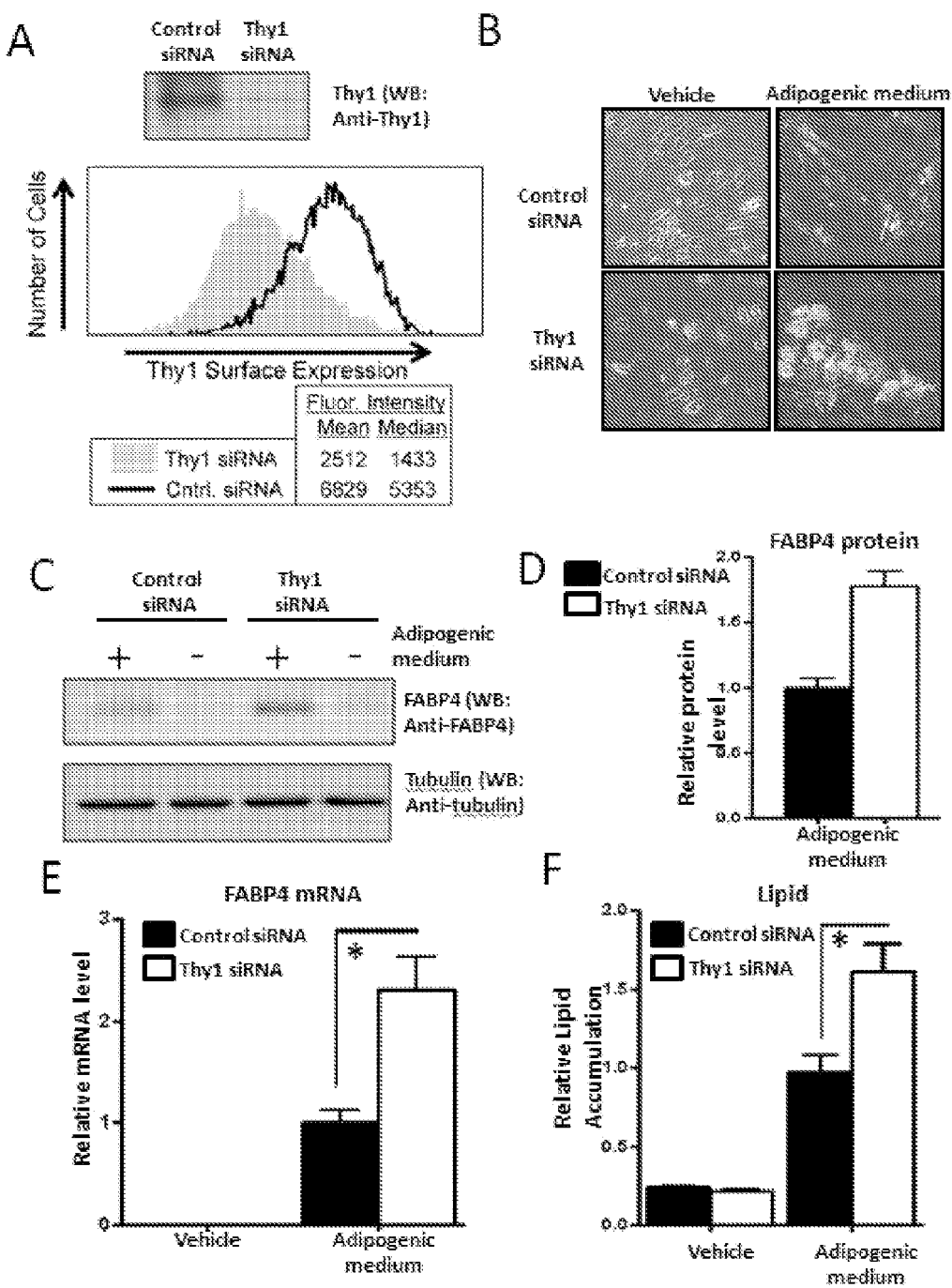
FIGS. 12A-12F show experimental results after Thy1 specific or control siRNA was introduced into human pre-adipocyte fibroblasts using Lipofectamine 2000. Fibroblasts were then treated with an adipogenic medium and adipogenesis was measured by visual inspection of lipid droplets, FABP4 expression and lipid accumulation. Total Thy1 protein expression and Thy1 surface expression were analyzed by western blot and flow cytometry, respectively.

Fibroblasts were then treated with an adipogenic medium and adipogenesis was measured by visual inspection of lipid droplets, FABP4 expression and lipid accumulation. Total Thy1 protein expression and Thy1 surface expression were analyzed by western blot and flow cytometry, respectively. FIG. 12A shows the results of western blot analysis, which demonstrates that Thy1 expression was reduced by Thy1 siRNA to less than 20% of control treated cells. Cell images were captured to show the presence of lipid droplets in fibroblasts treated with adipogenic medium, and are shown in FIG. 12B. Visual inspection revealed significantly more adipocytes in Thy1 siRNA treated cells compared to control. FIGS. 12C and 12D shown the results of western blot analysis of FABP4 and β-tubulin (loading control) levels. FABP4 expression was increased by 80% in cells treated with adipogenic medium and Thy1 siRNA compared to control. FABP4 mRNA and 18S rRNA (normalization control) levels were measured by RT-qPCR and the results shown in FIG. 12E. As shown, FABP4 mRNA levels were increased by 2.4 fold in cells treated with the adipogenic medium and Thy1 siRNA compared to the corresponding control. Lipid accumulation from cells treated as above were measured using the AdipoRed assay and the results shown in FIG. 12F. As shown, lipid accumulation was increased by 60% in cells treated with the adipogenic medium and Thy1 siRNA compared to control. Experiments were performed in at least three different human fibroblast strains and results are from a representative strain repeated in triplicate ($*=p<0.01$, Student's T test).

Example 9—Depletion of Soluble Thy1 from Culture Medium Increases Adipogenesis and FABP4 Expression in TED Adipocytes Conditioned media from Thy1+ cells contains shed (soluble) Thy1, and neutralizing this soluble Thy1 fraction leads to enhanced adipogenesis and enhanced mRNA expression of the PPARγ target, fatty acid binding protein 4 (FABP4). FIGS. 13A-13C show results demonstrating that depletion of soluble Thy1 from culture medium increases adipogenesis and FABP4 expression in TED adipocytes. FIG. 13A shows the results of Western blot analysis demonstrating soluble Thy1 present in Thy1+ orbital fibroblast conditioned medium can be depleted by incubation with a specific anti-Thy1 antibody but not an isotype control antibody. TED cell extract serves as a positive control. FIG. 13B is a bar graph of results of AdipoRed analysis of TED adipocytes cultured in Thy1-depleted conditioned medium showing enhanced adipogenesis. FIG. 13C is a bar graph of results showing that FABP4 mRNA expression is also remarkably increased when Thy1 is depleted from conditioned media. ($*p<0.01$ by Student's t-test.) This data provides evidence that Thy1 on the surface of orbital fibroblasts prevents TED adipogenesis.

Example 10—Thy1 Inhibits PPARγ Activity

Previous work demonstrates clear functional differences in orbital fibroblast subsets depending on their expression of Thy1. Koumas et al., "Thy-1 Expression in Human Fibroblast Subsets Defines Myofibroblastic or Lipofibroblastic Phenotypes," *Am J Pathol* 163(4):1291-300 (2003); Koumas et al., "Fibroblast Subsets in the Human Orbit: Thy-1+ and Thy-1-Subpopulations Exhibit Distinct Phenotypes," *Eur J Immunol* 32(2):477-85 (2002); Smith et al., "Orbital Fibroblast Heterogeneity May Determine the Clinical Presentation of Thyroid-Associated Ophthalmopathy," *J Clin Endocrinol Metab* 87(1):385-92 (2002); and Lehmann et al., "Novel Anti-Adipogenic Activity Produced by Human Fibroblasts," *Am J Physiol Cell Physiol* 299(3):C672-C681 (2010), each of which is hereby incorporated by reference in its entirety. However, until now, no molecular function has yet been identified for Thy1. In order for orbital fibroblasts to commit to adipogenesis, key signaling events and transcription factors must be regulated. One crucial transcription factor for adipogenesis is PPARγ. Brun et al., "Differential Activation of Adipogenesis by Multiple PPAR Isoforms. *Genes Dev* 10(8):974-84 (1996); Kim & Spiegelman, "Add1/Srebp1 Promotes Adipocyte Differentiation and Gene Expression Linked to Fatty Acid Metabolism," *Genes Dev* 10(9):1096-107 (1996); Spiegelman et al., "Regulation of Adipogenesis and Energy Balance by PPARgamma and PGC-1," *Int J Obes Relat Metab Disord* 24 Suppl 4:S8-10 (2000); Tontonoz et al., "Regulation of Adipocyte Gene Expression and Differentiation by Peroxisome Proliferator Activated Receptor Gamma," *Curr Opin Genet Dev* 5(5): 571-6 (1995); and Tontonoz & Spiegelman, "Fat and Beyond: The Diverse Biology of PPARgamma," *Annu Rev Biochem* 77:289-312 (2008), each of which is hereby incorporated by reference in its entirety. Activation of PPARγ by PPARγ ligands promotes differentiation into the adipocyte lineage.

Experiments were conducted that demonstrated Thy1 expression inhibits activity of the master adipogenic regulator, PPARγ. The activity of the key adipogenic transcription factor, PPARγ, was measured in various cells type using a PPARγ response element (PPREx3)-luciferase reporter. In the cell types tested, Thy1 expression reduced PPARγ activity. Thy1 cDNA or a control plasmid along with the PPREx 3-luc and control SV40-renilla reporter plasmids were introduced into 3T3-L1 cells via electroporation. Expression of Thy1 was confirmed by western blot and flow cytometry. Introduction of Thy1 reduces PPARγ activity by approximately 60% compared to control 3T3-L1 cells, as shown in FIG. 14A. HEK293FT cells were treated as in FIG. 14A with the addition a plasmid encoding PPARγ (pcDNA3.1-PPARγ). HEK293FT cells were then treated with vehicle (DMSO) or 100 nM of a synthetic PPARγ ligand, rosiglitazone (rosi). In both treatments, Thy1 expression reduces PPARγ activity ($*=p<0.01$, Student's T test), as shown in FIG. 14B. Human pre-adipocyte fibroblasts were treated as in FIG. 14A and then treated with DMSO or 100 nM rosi. Thy1 expression reduces the activity of PPARγ, as shown in FIG. 14C. Results are from experiments repeated in triplicate and represented as normalized average luciferase activity+standard error ($*=p<0.01$ and $**=p<0.001$, Student's T test).

To test how Thy1 affects PPARγ, it was first considered whether Thy1 would down-regulate the expression of PPARγ protein. However, two different strains of human TED orbital fibroblasts, sorted into Thy1+ or Thy1− subsets, expressed similar levels of PPARγ (FIG. 15A). Furthermore, expression of Thy1 in 3T3-L1 preadipocyte fibroblasts did not alter PPARγ protein levels (FIG. 15B). Thus, other ways that Thy1 could influence the function of PPARγ were considered, as described below.

How Thy1 expression can regulate post-transcriptional gene expression through microRNAs (miRNA) was then studied. Namely, Thy1 expression controls a miRNA pathway that regulates TED adipogenesis and inflammation. MiRNAs are small, non-coding endogenous RNAs that bind to target mRNAs and usually repress their translation and/or increase target mRNA decay. MiRNAs often target many distinct mRNAs and thus are incredibly powerful in their ability to regulate cell activity, differentiation and disease. Bartel, D. P., "Micrornas: Target Recognition and Regulatory Functions," *Cell* 136(2):215-33 (2009) and Carthew Sontheimer, "Origins and Mechanisms of Mirnas and Sirnas," *Cell* 136(4):642-55 (2009), each of which is hereby incorporated by reference in its entirety. However, in normal or TED human primary orbital fibroblasts there is virtually no information about their expression or activity. Herein it is shown that orbital Thy1⁻ fibroblasts have much higher levels of miRNA-130a compared to Thy1+ orbital fibroblasts and TED orbital fat is also high in miRNA-130a.

Thus, this evidence supports the belief that Thy1 expression controls the level of miRNA-130a and that this is another mechanism how Thy1 controls TED orbital fibroblast differentiation. These provocative findings highlight how Thy1 expression controls adipogenesis. It has been shown that orbital fibroblasts, especially the Thy1⁻ subset, produce high levels of pro-inflammatory mediators such as IL-8 (see FIG. 16). Koumas et al., "Fibroblast Subsets in the Human Orbit: Thy-1+ and Thy-1- Subpopulations Exhibit Distinct Phenotypes," *Eur J Immunol* 32(2):477-85 (2002); Koumas et al., "Fibroblast Heterogeneity: Existence of Functionally Distinct Thy1(+) and Thy1(-) Human Female Reproductive Tract Fibroblasts," *Am J Pathol* 159(3):925-35 (2001); and Hwang et al., "Orbital Fibroblasts from Patients with Thyroid-Associated Ophthalmopathy Overexpress Cd40: Cd154 Hyperinduces 11-6, 11-8, and Mcp-1," *Invest Ophthalmol Vis Sci* 50(5):2262-8 (2009), each of which is hereby incorporated by reference in its entirety. It is unknown whether expression of Thy1 controls inflammatory mediator production. Interestingly, since Thy1 appears to control miRNA-130a expression levels, alterations in inflammatory pathways gene(s) through post-transcriptional regulation by high miRNA-130a levels may promote the high pro-inflammatory mediator production observed in TED orbital fibroblasts. As described in more detail below, it is shown that expression of miRNA-130a in orbital fibroblasts dramatically increases production of the inflammatory cytokines IL-6 and IL-8.

PPARγ Transcriptional Activity is Decreased in Cells Expressing Thy1 cDNA

To directly measure the ability of PPARγ to activate gene expression, a PPAR response element (PPRE)/firefly luciferase reporter plasmid was introduced into fibroblast cultures (see FIG. 17A). In particular, Thy1 cDNA was introduced into cells containing a PPRE-luciferase reporter and a control Renilla reporter. Cells were treated with vehicle or a synthetic PPARγ ligand, pioglitazone (15d-PGJ2 gave similar results). PPRE-luciferase activity was normalized to Renilla activity. As shown in FIG. 17B, in both treatments, Thy1 expression reduced PPARγ activity.

Erk1/2 Activity is Enhanced in Cells Expressing Thy1

PPARγ phosphorylation at serine 82 (S82) inhibits ligand binding and severely reduces its ability to promote adipogenesis. Choi et al., "Anti-Diabetic Drugs Inhibit Obesity-Linked Phosphorylation of PPARgamma by Cdk5," *Nature* 466(7305):451-6 (2010); Aouadi et al., "Inhibition of P38mapk Increases Adipogenesis from Embryonic to Adult Stages," *Diabetes* 55(2):281-9 (2006); Burns & Vanden Heuvel, "Modulation of PPAR Activity Via Phosphorylation," *Biochim Biophys Acta* 1771(8):952-60 (2007); Engelman et al., "Specific Inhibitors of P38 Mitogen-Activated Protein Kinase Block 3T3-L1 Adipogenesis," *J Biol Chem* 273(48):32111-20 (1998); Hu et al., "Inhibition of Adipogenesis Through Map Kinase-Mediated Phosphorylation of PPARgamma," *Science* 274(5295):2100-3 (1996); and Prusty et al., "Activation of MEK/ERK Signaling Promotes Adipogenesis by Enhancing Peroxisome Proliferator-Activated Receptor Gamma (PPARgamma) and C/EBPalpha Gene Expression During the Differentiation of 3T3-L1 Preadipocytes," *J Biol Chem* 277(48):46226-32 (2002), each of which is hereby incorporated by reference in its entirety. Furthermore, the kinase that phosphorylates PPARγ at S82 is the MAP kinase, Erk. To investigate if Thy1 regulates the Erk pathway, Thy1 was expressed in 3T3-L1 cells and the activity of Erk1/2 (which corresponds to phospho-Erk) was monitored by western blotting (see FIGS. 18A and 18B). Thy1 expression increased Erk1/2 phosphorylation greater than 3-fold compared to control 3T3-L1 cells.

MiRNA-130α is Highly Expressed by Thy1⁻ Fibroblasts Compared to Thy1+ Fibroblasts and is Essential for Adipogenesis of TED Orbital Fibroblasts As noted above, miRNAs are endogenous, small RNAs that serve to regulate up to 90% of all human genes by suppressing target mRNA translation or increasing target mRNA degradation. New studies link expression of certain miRNAs with diseases such as rheumatoid arthritis, obesity and cancer. A screen to analyze expression of 88 common miRNAs was conducted to discover if miRNA expression was distinct in Thy1⁻ vs. Thy1+TED orbital fibroblasts. Remarkably, miRNA-130a was increased more than 3-fold in Thy1-cells (FIG. 19A). Further, it was found that miRNA-130a is elevated in TED orbital fat compared to other fat depots (FIG. 19B). A bioinformatic screen revealed that miRNA-130a may post-transcriptionally regulate multiple mRNAs encoding factors involved in suppressing inflammation such as GAX and HOXOA5. Chen et al., "Meox2 Regulates Nuclear Factor-Kappab Activity in Vascular Endothelial Cells through Interactions with P65 and Ikappabbeta," *Cardiovascular Research* 87(4):723-31 (2010); Mandeville et al., "Impact of the Loss of Hoxa5 Function on Lung Alveogenesis," *American Journal of Pathology* 169 (4):1312-27 (2006); and Urbich et al., "Role of Micrornas in Vascular Diseases, Inflammation, and Angiogenesis," *Cardiovasc Res* 79(4):581-8 (2008), each of which is hereby incorporated by reference in its entirety.

In orbital adipocytes, transfection with miRNA-130a dramatically increased lipid accumulation (FIGS. 20A-20B). Thy1⁻ orbital fibroblasts have higher adipogenic potential as well as an increased production of inflammatory mediators compared to Thy1+ cells. This data supports the belief that miRNA-130a is up-regulated in TED Thy1-orbital fibroblasts and adipocytes compared to normal cells.

TED Adipocytes Produce More IL-8 and MCP-1 than Abdominal Fat Adipocytes and Introduction of a miRNA-130a Mimic Greatly Increases IL-6 and IL-8 Production in Orbital Fibroblasts Aberrant regulation of miRNAs is now viewed as a fundamental hallmark in cancer and in some inflammatory diseases. However, whether these miRNAs are functionally significant, especially in TED, remains an unanswered question. It was demonstrated that miRNA-130a expression in TED orbital fibroblasts not only increases lipid accumulation (see FIGS. 20A and 20B), but also increases expression of pro-inflammatory mediators (such as IL-6 and IL-8) that promote TED pathology. It was next determined whether over-expression or inhibition of miRNA-130a would increase or decrease inflammatory mediator production, respectively. FIGS. 21A-21C shows that TED adipocytes produce more IL-8 and MCP-1 than abdominal fat adipocytes. Moreover, when Thy1 expression is reduced, production of IL-6 and IL-8 is increased. Studies in one strain of orbital fibroblasts show that introduction of a miRNA-130a mimic (i.e., a synthesized analog of microRNA-130a that functions as miRNA-130a) greatly increases IL-6 and IL-8 production (FIG. 22), further supporting the belief that expression or inhibition of miRNA-130a increases or decreases inflammatory mediator production, respectively.

Thy1 Regulates the Activity of PPARγ Through Fyn in Human Pre-Adipocyte Fibroblasts The PPRE×3-luc and control SV40-renilla reporter plasmids were introduced into human pre-adipocyte fibroblasts along with a control plasmid (pXL6) or plasmids that express either wild-type Fyn (pRK5-Fyn) or a kinase dead, dominant negative Fyn (pRK5-Fyn K299M). As shown in FIG. 23A, ectopic expression of Fyn results in a 4.5 fold increase in PPARγ transcriptional activity. Expression of dominant negative Fyn results in a greater than 70% reduction in PPARγ transcriptional activity. In FIG. 23B, in addition to reporter constructs the following expression plasmids were introduced: pXL6-empty (columns 1 and 2), pXL6-hThy1 (column 3), pRK5-Fyn (column 4), and a constitutively active Fyn mutant reporter plasmid, pRK5-Fyn Y531F (column 5). As shown in FIG. 23B, Thy1 expression reduced PPARγ activity by 50% (column 2 vs 3) while introduction of wild-type Fyn restored approximately 40% of control PPARγ activity (column 2 vs 4). Introduction of Fyn-Y531F increased PPARγ activity to over 100% of control (column 2 vs 5). Experiments were performed in at least two different strains and results are from a representative strain repeated in triplicate. FIG. 23C shows results demonstrating that Thy1 expression inhibits Fyn mediated phosphorylation of STAT5. In particular, western blotting shows that Thy1 expression reduces phospho-STAT5 levels, demonstrating an inhibition of Fyn activity. These data demonstrate that Thy1 regulates the activity of PPARγ through Fyn in human pre-adipocyte fibroblasts.

Thy1 Regulates Adipogenesis by Inhibiting the Activity of Fyn

Human primary pre-adipocyte fibroblasts were induced to differentiate into adipocytes with or without SU6656, a selective Fyn inhibitor. FIG. 24A shows the results of western blot analysis demonstrating that SU6656 decreases FABP4 protein expression to 30% of control. FIG. 24B shows results demonstrating that SU6656 decreased lipid accumulation to 55% of control. FIGS. 24C-24E show results of an experiment in which Thy1 specific or control siRNA were introduced into fibroblasts followed by adipocyte induction with or without SU6656. FABP4 mRNA expression (FIG. 24D) and lipid accumulation (FIG. 24E) were increased in cells treated with Thy1 siRNA. SU6656 treatment ablated the adipogenic effect of Thy1 siRNA. These data demonstrate that Thy1 regulates adipogenesis by inhibiting the activity of Fyn.

Example 11—Soluble Thy1 Delivered In Vivo to Prevent Diet Induced Obesity in a Pre-Clinical Mouse Model Milligram quantities of soluble Thy1 will be injected into mice receiving a high fat (60% kcals from fat) diet. Table 2 below summarizes injection site, dose of Thy1 and dose frequency.

TABLE 2

Experimental Design

| N (mouse #) | Injection Site | Thy1 dose (per mouse weight) | Dose Frequency |
|---|---|---|---|
| 5 | Intravenous | 0.2 mg/kg | 1/week |
| 5 | Intravenous | 0.2 mg/kg | 2/week |
| 5 | Intravenous | 0.4 mg/kg | 1/week |
| 5 | Intravenous | 0.4 mg/kg | 2/week |
| 10 | Intravenous | Saline only | 1 or 2/week |
| 5 | Subcutaneous | 0.2 mg/kg | 1/week |
| 5 | Subcutaneous | 0.2 mg/kg | 2/week |
| 5 | Subcutaneous | 0.4 mg/kg | 1/week |
| 5 | Subcutaneous | 0.4 mg/kg | 2/week |
| 10 | Subcutaneous | Saline only | 1 or 2/week |

Mice fed a high fat diet and treated as in Table 2 will be weighed weekly for the duration of the experiment (minimum of 8 weeks). Following the study, mice will be sacked for fat depot quantification, histologic analysis and fat tissue will be analyzed by western blot for the adipogenic markers FABP4, C/EBPα, Fyn, and phospho-Fyn. Serum samples will also be acquired for analysis of Thy1, adiponectin and glucose levels. Our previous work demonstrates that control mice will increase in weight by over 40% after 8 weeks on a high fat diet. It is expected that mice receiving Thy1 will gain significantly less weight and have significantly less fat accumulation.

Although preferred embodiments are depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inhibiting adipogenesis and/or decreasing adipocyte size in a subject having obesity, the method comprising:
   selecting a subject having obesity and
   administering to the selected subject a composition comprising an isolated and substantially pure Thy1 protein or polypeptide fragment thereof comprising the amino acid sequence of (i) amino acids 20-130 of SEQ ID NO: 1 or (ii) amino acids 20-130 of SEQ ID NO: 1 having one or more additions, substitutions, or deletions at amino acids corresponding to amino acids 42, 79, and/or 119 of SEQ ID NO: 1, wherein the Thy1 protein or polypeptide fragment inhibits PPAR-gamma activity and/or promotes ERK signaling in multipotent stromal cells to inhibit adipogenesis and/or decrease adipocyte size in the selected subject.

2. The method according to claim 1, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, by inhalation or by application to mucous membranes.

3. The method according to claim 1, wherein said administering is carried out by topical application of the composition to regions of the body with excessive fat accumulation.

4. The method according to claim 1, wherein said administering is carried out by subcutaneous delivery of the composition to regions of the body with excessive fat accumulation.

5. The method according to claim 1, wherein said administering is effective to decrease body weight, reduce adipose tissue accumulation, decrease blood glucose levels, reduce adipocyte hypertrophy, reduce total fat deposits, reduce total number of adipocytes, reduce inflammatory mediators, reduce IL-6, increase leptin, and/or reduce hemoglobin H1C in a tissue of the selected subject.

6. A method of inhibiting adipogenesis and/or decreasing adipocyte size, the method comprising:
   providing an isolated and substantially pure Thy1 protein or polypeptide fragment thereof comprising the amino acid sequence of (i) amino acids 20-130 of SEQ ID NO: 1 or (ii) amino acids 20-130 of SEQ ID NO: 1 having one or more additions, substitutions, or deletions at amino acids corresponding to amino acids 42, 79, and/or 119 of SEQ ID NO: 1, wherein the Thy1 protein or polypeptide fragment inhibits PPAR-gamma activity and/or promotes ERK signaling in multipotent stromal cells; and
   contacting an adipocyte or adipocyte precursor with the isolated and substantially pure Thy1 protein or polypeptide fragment thereof to inhibit adipogenesis and/or decrease adipocyte size.

7. A method of inhibiting adipogenesis and/or decreasing adipocyte size in a subject having thyroid eye disease, the method comprising:
   selecting a subject having thyroid eye disease and
   administering to the selected subject a composition comprising an isolated and substantially pure Thy1 protein or polypeptide fragment thereof comprising the amino acid sequence of (i) amino acids 20-130 of SEQ ID NO: 1 or (ii) amino acids 20-130 of SEQ ID NO: 1 having one or more additions, substitutions, or deletions at amino acids corresponding to amino acids 42, 79, and/or 119 of SEQ ID NO: 1, wherein the Thy1 protein or polypeptide fragment inhibits PPAR-gamma activity and/or promotes ERK signaling in multipotent stromal cells to inhibit adipogenesis and/or decrease adipocyte size in the selected subject.

8. The method according to claim 7, wherein said administering is carried out orally, parenterally, subcutaneously, intravenously, intramuscularly, intraperitoneally, by intranasal instillation, by implantation, by intracavitary or intravesical instillation, intraocularly, intraarterially, intralesionally, transdermally, by inhalation or by application to mucous membranes.

9. The method according to claim 7, wherein said administering is carried out by injecting the composition into the retro-ocular space or application of the composition comprising the agent onto a surface of the subject's eye.

10. The method according to claim 7, wherein the composition is a solution, suspension, or solid capable of delivery onto the eye surface.

* * * * *

SEQUENCE LISTING

<160> NUMBER OF SEQ ID NOS: 32

<210> SEQ ID NO 1
<211> LENGTH: 161
<212> TYPE: PRT
<213> ORGANISM: Homo sapiens
<220> FEATURE:
<221> NAME/KEY: MISC_FEATURE
<222> LOCATION: (85)..(85)
<223> OTHER INFORMATION: Xaa at position 85 is Asn or His

<400> SEQUENCE: 1

Met Asn Leu Ala Ile Ser Ile Ala Leu Leu Leu Thr Val Leu Gln Val
1               5                   10                  15

```
Ser Arg Gly Gln Lys Val Thr Ser Leu Thr Ala Cys Leu Val Asp Gln
            20                  25                  30

Ser Leu Arg Leu Asp Cys Arg His Glu Asn Thr Ser Ser Ser Pro Ile
        35                  40                  45

Gln Tyr Glu Phe Ser Leu Thr Arg Glu Thr Lys Lys His Val Leu Phe
    50                  55                  60

Gly Thr Val Gly Val Pro Glu His Thr Tyr Arg Ser Arg Thr Asn Phe
65                  70                  75                  80

Thr Ser Lys Tyr Xaa Met Lys Val Leu Tyr Leu Ser Ala Phe Thr Ser
            85                  90                  95

Lys Asp Glu Gly Thr Tyr Thr Cys Ala Leu His His Ser Gly His Ser
            100                 105                 110

Pro Pro Ile Ser Ser Gln Asn Val Thr Val Leu Arg Asp Lys Leu Val
            115                 120                 125

Lys Cys Glu Gly Ile Ser Leu Leu Ala Gln Asn Thr Ser Trp Leu Leu
130                 135                 140

Leu Leu Leu Leu Ser Leu Ser Leu Leu Gln Ala Thr Asp Phe Met Ser
145                 150                 155                 160

Leu

<210> SEQ ID NO 2
<211> LENGTH: 130
<212> TYPE: PRT
<213> ORGANISM: Dog

<400> SEQUENCE: 2

Met Asn Pro Ala Ile Gly Phe Ala Leu Leu Leu Thr Val Leu Gln Val
1               5                   10                  15

Ala Arg Gly Gln Lys Val Thr Ser Leu Thr Ala Cys Leu Val Asp Gln
            20                  25                  30

Ser Leu Arg Leu Asp Cys Arg His Glu Asn Ala Thr Thr Leu Pro Ile
        35                  40                  45

Gln Tyr Glu Phe Ser Met Thr Arg Glu Lys Lys Gln His Val Ile Tyr
    50                  55                  60

Gly Thr Val Gly Val Pro Glu His Ser Tyr Arg Ser Arg Thr Asn Phe
65                  70                  75                  80

Thr Ser Lys Tyr Asn Ile Lys Val Leu Tyr Leu Ser Gly Phe Thr Thr
            85                  90                  95

Lys Asp Glu Gly Thr Tyr Thr Cys Glu Leu Arg Leu Ser Gly Gln Pro
            100                 105                 110

Pro Ile Thr Ser Ser Lys Asn Val Thr Val Leu Arg Asp Lys Leu Val
            115                 120                 125

Lys Cys
130

<210> SEQ ID NO 3
<211> LENGTH: 130
<212> TYPE: PRT
<213> ORGANISM: Cat

<400> SEQUENCE: 3

Met Asn Pro Thr Ile Gly Ile Ala Val Leu Leu Thr Val Leu Gln Val
1               5                   10                  15

Ala Arg Gly Gln Lys Val Thr Ser Leu Thr Ala Cys Leu Val Asp Gln
            20                  25                  30

Ser Leu Arg Leu Asp Cys Arg His Glu Asn Ser Thr Thr Ser Pro Ile
```

```
                    35                  40                  45
Gln Tyr Glu Phe Ser Ile Thr Arg Glu Lys Lys His Val Ile Phe
 50                  55                  60

Gly Thr Met Gly Val Pro Glu His Ser Tyr Arg Ser Arg Thr Asn Phe
 65                  70                  75                  80

Thr Ser Lys Tyr Asn Ile Lys Val Leu Tyr Leu Ser Gly Phe Thr Thr
                 85                  90                  95

Lys Asp Glu Gly Met Tyr Thr Cys Glu Leu Gln Leu Ser Gly Gln Ser
                100                 105                 110

Thr Thr Ser Ser Ser Lys Asn Val Ser Val Leu Arg Asp Lys Leu Val
                115                 120                 125

Lys Cys
    130

<210> SEQ ID NO 4
<211> LENGTH: 130
<212> TYPE: PRT
<213> ORGANISM: Pig

<400> SEQUENCE: 4

Met Asn Pro Thr Ile Gly Ile Ala Leu Leu Leu Thr Val Leu Gln Val
  1               5                  10                  15

Ala Arg Gly Gln Lys Val Thr Ser Leu Thr Ala Cys Leu Val Asp Gln
                 20                  25                  30

Ser Leu Arg Leu Asp Cys Arg His Glu Asn Thr Thr Asn Leu Pro Ile
                 35                  40                  45

Gln Tyr Glu Phe Ser Leu Thr Arg Glu Lys Lys His Val Leu Leu
 50                  55                  60

Gly Thr Val Gly Val Pro Glu His Ser Tyr Arg Ser Arg Thr Asn Phe
 65                  70                  75                  80

Ser Ser Lys Tyr Asp Ile Lys Val Leu Tyr Leu Ser Gly Phe Thr Thr
                 85                  90                  95

Lys Asp Glu Gly Ile Tyr Ala Cys Glu Leu His Leu Ser Gly Gln Thr
                100                 105                 110

Pro Ser Ile Ser Ser Lys Asn Ile Ser Val Phe Arg Asp Lys Leu Val
                115                 120                 125

Lys Cys
    130

<210> SEQ ID NO 5
<211> LENGTH: 131
<212> TYPE: PRT
<213> ORGANISM: Mouse

<400> SEQUENCE: 5

Met Asn Pro Ala Ile Ser Val Ala Leu Leu Leu Ser Val Leu Gln Val
  1               5                  10                  15

Ser Arg Gly Gln Lys Val Thr Ser Leu Thr Ala Cys Leu Val Asn Gln
                 20                  25                  30

Asn Leu Arg Leu Asp Cys Arg His Glu Asn Asn Thr Lys Asp Asn Ser
                 35                  40                  45

Ile Gln His Glu Phe Ser Leu Thr Arg Glu Lys Arg Lys His Val Leu
 50                  55                  60

Ser Gly Thr Leu Gly Ile Pro Glu His Thr Tyr Arg Ser Arg Val Thr
 65                  70                  75                  80

Leu Ser Asn Gln Pro Tyr Ile Lys Val Leu Thr Leu Ala Asn Phe Thr
```

```
                         85                   90                   95
Thr Lys Asp Glu Gly Asp Tyr Phe Cys Glu Leu Gln Val Ser Gly Ala
                    100                 105                 110

Asn Pro Met Ser Ser Asn Lys Ser Ile Ser Val Tyr Arg Asp Lys Leu
                115                 120                 125

Val Lys Cys
    130

<210> SEQ ID NO 6
<211> LENGTH: 130
<212> TYPE: PRT
<213> ORGANISM: Rat

<400> SEQUENCE: 6

Met Asn Pro Val Ile Ser Ile Thr Leu Leu Leu Ser Val Leu Gln Met
1               5                  10                  15

Ser Arg Gly Gln Arg Val Ile Ser Leu Thr Ala Cys Leu Val Asn Gln
                20                  25                  30

Asn Leu Arg Leu Asp Cys Arg His Glu Asn Asn Thr Asn Leu Pro Ile
            35                  40                  45

Gln His Glu Phe Ser Leu Thr Arg Glu Lys Lys His Val Leu Ser
    50                  55                  60

Gly Thr Leu Gly Val Pro Glu His Thr Tyr Arg Ser Arg Val Asn Leu
65                  70                  75                  80

Phe Ser Asp Arg Phe Ile Lys Val Leu Thr Leu Ala Asn Phe Thr Thr
                85                  90                  95

Lys Asp Glu Gly Asp Tyr Met Cys Glu Leu Arg Val Ser Gly Gln Asn
                    100                 105                 110

Pro Thr Ser Ser Asn Lys Thr Ile Asn Val Ile Arg Asp Lys Leu Val
                115                 120                 125

Lys Cys
    130

<210> SEQ ID NO 7
<211> LENGTH: 130
<212> TYPE: PRT
<213> ORGANISM: Chicken

<400> SEQUENCE: 7

Met Asn Pro Thr Val Ser Ile Ala Val Ile Leu Thr Val Leu Gln Ala
1               5                  10                  15

Ala His Cys Gln Met Ile Arg Asp Leu Ser Ala Cys Leu Leu Gly Gln
                20                  25                  30

Ser Leu Arg Val Asp Cys Arg Tyr Glu Asn Lys Thr Ser Asp Pro Leu
            35                  40                  45

Thr Tyr Glu Phe Ser Leu Thr Lys Asp Asn Arg Lys His Ile Ile Gln
    50                  55                  60

Ser Thr Ile Ser Val Ser Glu Asn Val Tyr Arg Asn Arg Ala Asn Val
65                  70                  75                  80

Thr Met His Lys Asn Leu Val Cys Leu Tyr Leu His Ser Phe Thr Thr
                85                  90                  95

Ser Asp Glu Gly Val Tyr Met Cys Glu Leu Lys Ala Thr Asn Asp Tyr
                    100                 105                 110

Thr Gly Asn Gln Ile Lys Asn Ile Thr Val Ile Lys Asp Lys Leu Glu
                115                 120                 125

Lys Cys
```

```
                   130

<210> SEQ ID NO 8
<211> LENGTH: 126
<212> TYPE: PRT
<213> ORGANISM: Zebrafish

<400> SEQUENCE: 8

Met Phe Tyr Thr Ala Phe Ala Thr Leu Phe Leu Gly Val Val Thr
1               5                   10                  15

Ala Gln Thr Ser Leu Arg Ile Thr Ser Cys Leu Thr Lys Asp Gln Asn
                20                  25                  30

Leu Gln Met Ser Cys Thr Phe Thr Pro Ala Pro Asp Thr Lys Leu Ser
            35                  40                  45

Lys Thr Cys Tyr Tyr Met Thr Asp Asn Lys Leu Ile Gly Ser Thr Asn
        50                  55                  60

Ser Ser Ser Thr Pro Asp Ser Thr Phe Arg Asn Arg Ala Asn Val Thr
65                  70                  75                  80

Ile Thr Asp Asn Lys Cys Asp Leu Tyr Leu Lys Gly Leu Pro Asp Ser
                85                  90                  95

Lys Pro Ala Asn Tyr Thr Cys Phe Ile Arg Gln Thr Ala Ser Pro Val
            100                 105                 110

Ser Ile Ile Gln Thr Val Asp Lys Ser Lys Leu Gln Thr Cys
        115                 120                 125

<210> SEQ ID NO 9
<211> LENGTH: 134
<212> TYPE: PRT
<213> ORGANISM: Xenopus

<400> SEQUENCE: 9

Met Asn Tyr Phe Leu Leu Val Thr Phe Ile Leu Ser Val Leu Gln Ala
1               5                   10                  15

Thr Asp Cys Gln Arg Ile Thr Ser Leu Thr Ala Cys Leu Met Arg Pro
                20                  25                  30

Gly Pro Lys Leu Arg Ile Asp Cys Arg Tyr Leu Asn Thr Thr Asn Asn
            35                  40                  45

Pro Met Arg Tyr Glu Phe Lys Val Asn Arg Gly Gly Glu Pro Gln Ile
        50                  55                  60

Ile Leu Ser Thr Ile Asn Val Asn Phe Phe Ser Asp Lys Tyr His Asn
65                  70                  75                  80

Arg Ala Ser Pro Ser Ile Thr Arg Gly Leu Val Gln Leu His Leu Glu
                85                  90                  95

Arg Phe Asn Ala Ser Asp Ala Gly Leu Tyr Thr Cys Asn Leu Phe Ile
            100                 105                 110

Pro Asn Asp Leu Thr Ile Asn Gln Thr Ala Ser Ile Gly Val Gln Lys
        115                 120                 125

Asp Lys Leu Glu Thr Cys
        130

<210> SEQ ID NO 10
<211> LENGTH: 114
<212> TYPE: PRT
<213> ORGANISM: Artificial
<220> FEATURE:
<223> OTHER INFORMATION: Consensus sequence Thy1

<400> SEQUENCE: 10
```

```
Met Asn Pro Ile Ser Ile Ala Leu Leu Leu Thr Val Leu Gln Val Ala
1               5                   10                  15

Arg Gly Gln Lys Val Thr Ser Leu Thr Ala Cys Leu Val Gln Ser Leu
            20                  25                  30

Arg Leu Asp Cys Arg His Glu Asn Thr Pro Ile Gln Tyr Glu Phe Ser
        35                  40                  45

Leu Thr Arg Glu Lys Lys Lys His Val Ile Gly Thr Val Gly Val Pro
    50                  55                  60

Glu His Thr Tyr Arg Ser Arg Asn Thr Ser Asn Ile Lys Val Leu Tyr
65                  70                  75                  80

Leu Ser Gly Phe Thr Thr Lys Asp Glu Gly Tyr Thr Cys Glu Leu Leu
                85                  90                  95

Ser Gly Pro Ser Ser Lys Asn Ile Thr Val Leu Arg Asp Lys Leu Val
            100                 105                 110

Lys Cys

<210> SEQ ID NO 11
<211> LENGTH: 19
<212> TYPE: PRT
<213> ORGANISM: Artificial
<220> FEATURE:
<223> OTHER INFORMATION: Thy1 polypeptide fragment
<220> FEATURE:
<221> NAME/KEY: MISC_FEATURE
<222> LOCATION: (1)..(1)
<223> OTHER INFORMATION: Xaa at position 1 is Ac or acetylation

<400> SEQUENCE: 11

Xaa Gln Lys Val Thr Ser Leu Thr Ala Cys Leu Val Asp Gln Ser Leu
1               5                   10                  15

Arg Leu Asp

<210> SEQ ID NO 12
<211> LENGTH: 21
<212> TYPE: PRT
<213> ORGANISM: Artificial
<220> FEATURE:
<223> OTHER INFORMATION: Thy1 polypeptide fragment
<220> FEATURE:
<221> NAME/KEY: MISC_FEATURE
<222> LOCATION: (6)..(6)
<223> OTHER INFORMATION: Xaa at position 6 is N glycosylation site

<400> SEQUENCE: 12

Cys Arg His Glu Asn Xaa Thr Ser Ser Pro Ile Gln Tyr Glu Phe
1               5                   10                  15

Ser Leu Thr Arg Glu
            20

<210> SEQ ID NO 13
<211> LENGTH: 26
<212> TYPE: PRT
<213> ORGANISM: Artificial
<220> FEATURE:
<223> OTHER INFORMATION: Thy1 polypeptide fragment
<220> FEATURE:
<221> NAME/KEY: MISC_FEATURE
<222> LOCATION: (23)..(23)
<223> OTHER INFORMATION: Xaa at position 23 is N glycosylation site

<400> SEQUENCE: 13

Thr Lys Lys His Val Leu Phe Gly Thr Val Gly Val Pro Glu His Thr
1               5                   10                  15
```

Tyr Arg Ser Arg Thr Asn Xaa Phe Thr Ser
            20                  25

<210> SEQ ID NO 14
<211> LENGTH: 21
<212> TYPE: PRT
<213> ORGANISM: Artificial
<220> FEATURE:
<223> OTHER INFORMATION: Thy1 polypeptide fragment

<400> SEQUENCE: 14

Lys Tyr Asn Met Lys Val Leu Tyr Leu Ser Ala Phe Thr Ser Lys Asp
1               5                   10                  15

Glu Gly Thr Tyr Thr
            20

<210> SEQ ID NO 15
<211> LENGTH: 28
<212> TYPE: PRT
<213> ORGANISM: Artificial
<220> FEATURE:
<223> OTHER INFORMATION: Thy1 polypeptide fragment
<220> FEATURE:
<221> NAME/KEY: MISC_FEATURE
<222> LOCATION: (17)..(17)
<223> OTHER INFORMATION: Xaa at position 17 is N glycosylation site

<400> SEQUENCE: 15

Cys Ala Leu His His Ser Gly His Ser Pro Pro Ile Ser Ser Gln Asn
1               5                   10                  15

Xaa Val Thr Val Leu Arg Asp Lys Leu Val Lys Cys
            20                  25

<210> SEQ ID NO 16
<211> LENGTH: 2806
<212> TYPE: DNA
<213> ORGANISM: Homo sapiens

<400> SEQUENCE: 16

```
ggatccagga ctgagatccc agaaccatga acctggccat cagcatcgct ctcctgctaa    60
caggtacccg gcatggggca ggactggggc tccaggcgcc ctggcttcct tccctccaga   120
gaagcagctt ctccctcaca gtctcagaaa agcgcaggtg acaaagagag gctcttttt    180 catcctgaag tcagccgatc caccgcgctg atattctgac ggcctgaggt ggttttggaa   240
aacacagttt gctgagccct ccttcacact attgaactag atccccaac tgagaaccca    300 ggaaccagca tcaactccct aagatctcct gtccttgaaa cacattgata ggatccaagg   360
ctcaagcaga gtggggaggg aggctggggt ctgcaaagga gaagtgggat ccctggggtg   420
gggaaaggca ctcagagagc agaccccggt cccctcccta gccaggccca tctctccact   480
tcaggtgggt gggaggcccc tgtgccgcag gcccctccag tttgaaggag gcactgctgg   540
tgccagtctt gcaggtctcc cgagggcaga aggtgaccag cctaacggcc tgcctagtgg   600
accagagcct tcgtctggac tgccgccatg agaataccag cagttcaccc atccagtacg   660
agttcagcct gacccgtgag acaaagaagc acgtgctctt tggcactgtg ggggtgcctg   720
agcacacata ccgctcccga accaacttca ccagcaaata ccacatgaag gtcctctact   780
tatccgcctt cactagcaag gacgagggca cctacacgtg tgcactccac cactctggcc   840
attccccacc catctcctcc cagaacgtca cagtgctcag aggtgagaca gcccctaac    900 aaggtcaagt gagctgggag agccaggctc ggggacagca ggcagttccc ttggctggac   960
```

```
tagagaggag aatagcccca taacgctctc accctctccc aactgctgcc tggtcaactg      1020
gggaaccatt gccttcggtg tgaatggggt gaagagctca gggccagaca ggcagagcag      1080
tgtggttcca ccagaactgt gggcaaggcc tttggcccct aatcttcctt ctcccagcgg      1140
gaaacaggga tgacaccacc tccctcagcc agtttcttg tcatgatgtt tagtaaggtt       1200
ttcataagat gatatgtgtg caagagatca gtaatctgca aatgggaaag atggctggtt     1260
ctgtgagacc aggctgttcc tggtcccagc taagacattg cagtacccac ctcccaaagg     1320
gagtacaccc ttgctttggg cctgtgcctg cctgagtcct gatccgtctt ccttcctacc    1380
ctgcccccgg cccccttctc tttctgcaga caaactggtc aagtgtgagg gcatcagcct    1440
gctggctcag aacacctcgt ggctgctgct gctcctgctg tccctctccc tcctccaggc    1500
cacggatttc atgtccctgt gactggtggg gcccatggag gagacaggaa gcctcaagtt    1560
ccagtgcaga gatcctactt ctctgagtca gctgaccccc tcccccaat ccctcaaacc     1620 ttgaggagaa gtggggaccc caccctcat caggagttcc agtgctgcat gcgattatct     1680
acccacgtcc acgcggccac ctcacctct ccgcacacct ctggctgtct tttgtactt      1740 tttgttccag agctgcttct gtctggttta tttaggtttt atccttcctt ttctttgaga   1800
gttcgtgaag agggaagcca ggattgggga cctgatggag agtgagagca tgtgagggt    1860 agtgggatgg tggggtacca gccactggag gggtcatcct tgcccatcgg gaccagaaac    1920
ctgggagaga cttggatgag gagtggttgg gctgtgctgg gctagcacg acatggtct    1980 gtcctgacag cactcctcgg caggcatggc tggtgcctga agaccccaga tgtgagggca    2040
ccaccaagaa tttgtggcct accttgtgag gagagaact gaggatctcc agcattctca    2100
gccacaacca aaaaaaata aaagggcag ccctccttac cactgtggaa gtccctcaga     2160
ggccttgggg catgacccag tgaagatgca ggtttgacca ggaaagcagc gctagtggag    2220
ggttggagaa ggaggtaaag gatgagggtt catcatccct ccctgcctaa ggaagctaaa   2280
agcatggccc tgctgcccct ccctgcctcc acccacagtg gagagggcta caaaggagga    2340
caagaccctc tcaggctgtc ccaagctccc aagagcttcc agagctctga cccacagcct   2400
ccaagtcagg tggggtggag tcccagagct gcacagggtt tggcccaagt ttctaaggga    2460
ggcacttcct cccctcgccc atcagtgcca gcccctgctg gctggtgcct gagcccctca    2520
gacagccccc tgccccgcag gcctgccttc tcagggactt ctgcggggcc tgaggcaagc    2580
catggagtga gacccaggag ccggacactt ctcaggaaat ggcttttccc aacccccagc    2640
ccccacccgg tggttcttcc tgttctgtga ctgtgtatag tgccaccaca gcttatggca    2700
tctcattgag gacaaagaaa actgcacaat aaaaccaagc ctctggaatc tgtcctcgtg    2760
tccacctggc cttcgctcct ccagcagtgc ctgcctgccc ccgctt                  2806
```

<210> SEQ ID NO 17
<211> LENGTH: 486
<212> TYPE: DNA
<213> ORGANISM: Homo sapiens

<400> SEQUENCE: 17

```
atgaacctgg ccatcagcat cgctctcctg ctaacagtct tgcaggtctc ccgagggcag      60
aaggtgacca gcctaacggc ctgcctagtg gaccagagcc ttcgtctgga ctgccgccat     120
gagaatacca gcagttcacc catccagtac gagttcagcc tgacccgtga gacaaagaag     180
cacgtgctct ttggcactgt gggggtgcct gagcacacat accgctcccg aaccaacttc     240
accagcaaat acaacatgaa ggtcctctac ttatccgcct tcactagcaa ggacgagggc    300
```

```
acctacacgt gtgcactcca ccactctggc cattcccac  ccatctcctc ccagaacgtc    360
acagtgctca gagacaaact ggtcaagtgt gagggcatca gcctgctggc tcagaacacc    420
tcgtggctgc tgctgctcct gctctccctc tccctcctcc aggccacgga tttcatgtcc    480
ctgtga                                                                486
```

<210> SEQ ID NO 18
<211> LENGTH: 21
<212> TYPE: DNA
<213> ORGANISM: Artificial
<220> FEATURE:
<223> OTHER INFORMATION: Primer

<400> SEQUENCE: 18
cgaaacgccg aatataatcc c                                               21

<210> SEQ ID NO 19
<211> LENGTH: 23
<212> TYPE: DNA
<213> ORGANISM: Artificial
<220> FEATURE:
<223> OTHER INFORMATION: Primer

<400> SEQUENCE: 19
cccaacttct gtacaactct agc                                             23

<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
acaggaaagt caagagcacc                                                 20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
aacttcagtc caggtcaacg                                                 20

<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
atctcctccc agaacgtc                                                   18

<210> SEQ ID NO 23
<211> LENGTH: 19
<212> TYPE: DNA
<213> ORGANISM: Artificial
<220> FEATURE:
<223> OTHER INFORMATION: Primer

<400> SEQUENCE: 23
atctctgcac tggaacttg                                                19

<210> SEQ ID NO 24
<211> LENGTH: 20
<212> TYPE: DNA
<213> ORGANISM: Artificial
<220> FEATURE:
<223> OTHER INFORMATION: Primer

<400> SEQUENCE: 24
tgagaaacgg ctaccacatc                                               20

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
actacgagct ttttaactgc                                               20

<210> SEQ ID NO 26
<211> LENGTH: 17
<212> TYPE: DNA
<213> ORGANISM: Artificial
<220> FEATURE:
<223> OTHER INFORMATION: Primer

<400> SEQUENCE: 26
gcacagagcc tcgcctt                                                  17

<210> SEQ ID NO 27
<211> LENGTH: 17
<212> TYPE: DNA
<213> ORGANISM: Artificial
<220> FEATURE:
<223> OTHER INFORMATION: Primer

<400> SEQUENCE: 27
ccttgcacat gccggag                                                  17

<210> SEQ ID NO 28
<211> LENGTH: 22
<212> TYPE: DNA
<213> ORGANISM: Artificial
<220> FEATURE:
<223> OTHER INFORMATION: Primer

<400> SEQUENCE: 28
atggaaatcc catcaccatc tt                                            22

<210> SEQ ID NO 29
<211> LENGTH: 18
<212> TYPE: DNA
<213> ORGANISM: Artificial
<220> FEATURE:
<223> OTHER INFORMATION: Primer

<400> SEQUENCE: 29
cggcccactt gattttgg                                                 18

<210> SEQ ID NO 30
<211> LENGTH: 30
<212> TYPE: DNA
<213> ORGANISM: Artificial

-continued

```
<220> FEATURE:
<223> OTHER INFORMATION: Primer

<400> SEQUENCE: 30
tactcgagtg actggtgggg cccatggagg                                      30

<210> SEQ ID NO 31
<211> LENGTH: 33
<212> TYPE: DNA
<213> ORGANISM: Artificial
<220> FEATURE:
<223> OTHER INFORMATION: Primer

<400> SEQUENCE: 31
tagcggccgc tgggcaaatg tgtctcgtta ggg                                  33

<210> SEQ ID NO 32
<211> LENGTH: 135
<212> TYPE: PRT
<213> ORGANISM: Artificial
<220> FEATURE:
<223> OTHER INFORMATION: Consensus sequence Thy1
<220> FEATURE:
<221> NAME/KEY: MISC_FEATURE
<222> LOCATION: (4)..(4)
<223> OTHER INFORMATION: Xaa at position 4 is either Ala, Thr, Val, or
      Phe
<220> FEATURE:
<221> NAME/KEY: MISC_FEATURE
<222> LOCATION: (31)..(31)
<223> OTHER INFORMATION: Xaa at position 31 is either Asp, Asn, Gly,
      Lys, or Arg
<220> FEATURE:
<221> NAME/KEY: MISC_FEATURE
<222> LOCATION: (34)..(34)
<223> OTHER INFORMATION: Xaa at position 34 is either Asn, Pro, or a gap
<220> FEATURE:
<221> NAME/KEY: MISC_FEATURE
<222> LOCATION: (35)..(35)
<223> OTHER INFORMATION: Xaa at position 35 is either Lys or a gap
<220> FEATURE:
<221> NAME/KEY: MISC_FEATURE
<222> LOCATION: (45)..(45)
<223> OTHER INFORMATION: Xaa at position 45 is either Thr, Ala, Ser,
      Asn, or Lys
<220> FEATURE:
<221> NAME/KEY: MISC_FEATURE
<222> LOCATION: (47)..(47)
<223> OTHER INFORMATION: Xaa at position 47 is either Ser, Thr, Asn,
      Lys, or Asp
<220> FEATURE:
<221> NAME/KEY: MISC_FEATURE
<222> LOCATION: (48)..(48)
<223> OTHER INFORMATION: Xaa at position 48 is either Asp, Lys, or a gap
<220> FEATURE:
<221> NAME/KEY: MISC_FEATURE
<222> LOCATION: (49)..(49)
<223> OTHER INFORMATION: Xaa at position 49 is either Ser, Leu, Asn,
      Asp, or Lys
<220> FEATURE:
<221> NAME/KEY: MISC_FEATURE
<222> LOCATION: (67)..(67)
<223> OTHER INFORMATION: Xaa at position 67 is either Phe, Tyr, Leu,
      Ser, Gln, or Gly
<220> FEATURE:
<221> NAME/KEY: MISC_FEATURE
<222> LOCATION: (74)..(74)
<223> OTHER INFORMATION: Xaa at position 74 is either Thr, Phe, or a gap
<220> FEATURE:
<221> NAME/KEY: MISC_FEATURE
<222> LOCATION: (75)..(75)
<223> OTHER INFORMATION: Xaa at position 75 is either Pro, Phe, or a gap
<220> FEATURE:
<221> NAME/KEY: MISC_FEATURE
<222> LOCATION: (83)..(83)
```

-continued

```
<223> OTHER INFORMATION: Xaa at position 83 is either Thr, Val, or Ala
<220> FEATURE:
<221> NAME/KEY: MISC_FEATURE
<222> LOCATION: (85)..(85)
<223> OTHER INFORMATION: Xaa at position 85 is either Phe, Leu, Val, or
      Pro
<220> FEATURE:
<221> NAME/KEY: MISC_FEATURE
<222> LOCATION: (88)..(88)
<223> OTHER INFORMATION: Xaa at position 88 is either Lys, Gln, Asp,
      His, or Thr
<220> FEATURE:
<221> NAME/KEY: MISC_FEATURE
<222> LOCATION: (89)..(89)
<223> OTHER INFORMATION: Xaa at position 89 is either Tyr, Pro, Arg,
      Lys, or Asp
<220> FEATURE:
<221> NAME/KEY: MISC_FEATURE
<222> LOCATION: (106)..(106)
<223> OTHER INFORMATION: Xaa at position 106 is either Thr, Met, Ile,
      Asp, Val, Asn, or Leu
<220> FEATURE:
<221> NAME/KEY: MISC_FEATURE
<222> LOCATION: (112)..(112)
<223> OTHER INFORMATION: Xaa at position 112 is either His, Arg, Gln,
      Lys, or Phe
<220> FEATURE:
<221> NAME/KEY: MISC_FEATURE
<222> LOCATION: (116)..(116)
<223> OTHER INFORMATION: Xaa at position 116 is either His, Gln, Ala,
      Asp, or Ser
<220> FEATURE:
<221> NAME/KEY: MISC_FEATURE
<222> LOCATION: (117)..(117)
<223> OTHER INFORMATION: Xaa at position 117 is either Ser, Pro, Thr,
      Asn, Tyr, or Leu
<220> FEATURE:
<221> NAME/KEY: MISC_FEATURE
<222> LOCATION: (119)..(119)
<223> OTHER INFORMATION: Xaa at position 119 is either Pro, Ile, Thr,
      Ser, Met, Gly, or a gap
<220> FEATURE:
<221> NAME/KEY: MISC_FEATURE
<222> LOCATION: (120)..(120)
<223> OTHER INFORMATION: Xaa at position 120 is either Ile, Thr, Ser,
      Asn, or a gap

<400> SEQUENCE: 32

Met Asn Pro Xaa Ile Ser Ile Ala Leu Leu Leu Thr Val Leu Gln Val
1               5                   10                  15

Ala Arg Gly Gln Lys Val Thr Ser Leu Thr Ala Cys Leu Val Xaa Gln
            20                  25                  30

Ser Xaa Xaa Leu Arg Leu Asp Cys Arg His Glu Asn Xaa Thr Xaa Xaa
        35                  40                  45

Xaa Pro Ile Gln Tyr Glu Phe Ser Leu Thr Arg Glu Lys Lys Lys His
    50                  55                  60

Val Ile Xaa Gly Thr Val Gly Val Pro Xaa Xaa Arg His Thr Tyr Arg
65                  70                  75                  80

Ser Arg Xaa Asn Xaa Thr Ser Xaa Xaa Asn Ile Lys Val Leu Tyr Leu
            85                  90                  95

Ser Gly Phe Thr Thr Lys Asp Glu Gly Xaa Tyr Thr Cys Glu Leu Xaa
            100                 105                 110

Leu Ser Gly Xaa Xaa Pro Xaa Xaa Ser Ser Lys Asn Ile Thr Val Leu
        115                 120                 125

Arg Asp Lys Leu Val Lys Cys
130                 135
```